(12) United States Patent
Baumann et al.

(10) Patent No.: US 8,664,235 B2
(45) Date of Patent: Mar. 4, 2014

(54) 6-HALOGENO-[1,2,4]TRIAZOLO[1,5-A] PYRIMIDINES FOR COMBATING ANIMAL PESTS

(75) Inventors: Ernst Baumann, Dudenhofen (DE); Thomas Grote, Wachenheim (DE); Frank Schieweck, Heßheim (DE); Wolfgang von Deyn, Neustadt (DE); Norbert Götz, Worms (DE); Michael Hofmann, Ludwigshafen (DE); Markus Kordes, Frankenthal (DE); Michael Puhl, Lampertheim (DE); Michael Rack, Heidelberg (DE); Thomas Schmidt, Neustadt (DE); Toni Bucci, Fuquay Varina, NC (US); Henry Van Tuyl Cotter, Raleigh, NC (US); Deborah L. Culbertson, Fuquay Varina, NC (US); Hassan Oloumi-Sadeghi, Raleigh, NC (US)

(73) Assignee: Merial Limited, Duluth, GA (US)

( * ) Notice: Subject to any disclaimer, the term of this patent is extended or adjusted under 35 U.S.C. 154(b) by 2144 days.

(21) Appl. No.: 10/570,854

(22) PCT Filed: Sep. 10, 2004

(86) PCT No.: PCT/EP2004/010132
§ 371 (c)(1),
(2), (4) Date: Mar. 7, 2006

(87) PCT Pub. No.: WO2005/025315
PCT Pub. Date: Mar. 24, 2005

(65) Prior Publication Data
US 2006/0264446 A1    Nov. 23, 2006

Related U.S. Application Data

(60) Provisional application No. 60/502,281, filed on Sep. 12, 2003.

(51) Int. Cl.
   *A01N 43/54*         (2006.01)
   *A61K 31/505*      (2006.01)
   *A01N 25/32*        (2006.01)

(52) U.S. Cl.
   USPC .......................................... 514/269; 424/406

(58) Field of Classification Search
   USPC ........................................... 514/269; 424/406
   See application file for complete search history.

(56) References Cited

U.S. PATENT DOCUMENTS

| 4,144,330 A | 3/1979 | Gsell et al. |
| 2004/0097522 A1 | 5/2004 | Gebauer et al. |

FOREIGN PATENT DOCUMENTS

| DE | 55 956 | 5/1967 |
| DE | 99 794 | 8/1973 |
| EP | 0 550 113 | 7/1993 |
| FR | 1567021 | 5/1969 |
| GB | 1 148 629 | 4/1969 |
| WO | WO 02/50077 | 6/2002 |
| WO | WO 03/039259 | 5/2003 |

*Primary Examiner* — Benjamin Packard
(74) *Attorney, Agent, or Firm* — Judy Jarecki-Black; John Ezcurra; Merial Limited

(57) ABSTRACT

The present invention relates to a method of combating animal pests which comprises contacting the animal pests, their habit, breeding ground, food supply, plant, seed, soil, area, material or environment in which the animal pests are growing or may grow, or the materials, plants, seeds, soils, surfaces or spaces to be protected from animal attack or infestation with a pesticidally effective amount of at least one 6-halogeno [1,2,4]triazolo[1,5-a]-pyrimidine of the general formula (I), wherein X, $R^1$, $R^2$, $R^3$ and $R^4$ are as defined in claim 1 and/or the agriculturally useful salts thereof.

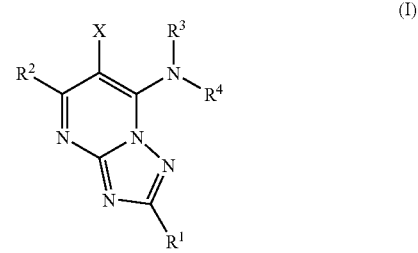

(I)

11 Claims, No Drawings

6-HALOGENO-[1,2,4]TRIAZOLO[1,5-A] PYRIMIDINES FOR COMBATING ANIMAL PESTS

This application is a National Stage application of International Application No. PCT/EP2004/010132, filed Sep. 10, 2004, which claims the benefit of U.S. Provisional Application No. 60/502,281, filed Sep. 12, 2003, the entire contents of which is hereby incorporated herein by reference in its entirety.

The present invention relates to 6-halogeno-[1,2,4]triazolo [1,5-a]pyrimidines for combating animal pests.

Animal pests destroy growing and harvested crops and attack wooden dwelling and commercial structures, causing large economic loss to the food supply and to property. While a large number of pesticidal agents are known, due to the ability of target pests to develop resistance to said agents, there is an ongoing need for new agents for combating animal pests. In particular, animal pests such as insects, acaridae and/or arachnids are difficult to be effectively controlled.

It is therefore an object of the present invention to provide compounds having a good pesticidal activity, especially against difficult to control insects, arachnids and acaridae.

DD 55 956, DD 99 794 and FR 1567021 describe [1,2,4]-triazolo[1,5-a]pyrimidines of the general formula (A) having a pharmaceutical activity,

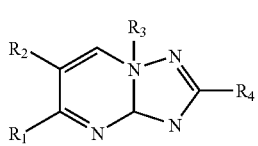

(A)

wherein $R_1$, $R_4$ may be hydrogen, lower alkyl, alkoxyalkyl, halogen, aryl or arylalkyl, $R_2$ may be hydrogen, halogen, lower alkyl, lower alkenyl, arylalkyl or aryl and $R_3$ may be an optionally substituted amino group, wherein the substituents are selected—inter alia—from alkyl, cycloalkyl, alkenyl, hydroxylalkyl, alkylaminoalkyl, alkoxyalkyl, aryl, arylalkyl, heteroaryl or heteroaralkyl.

WO 03/039259 describes substituted s-1,2,4-triazolo[1,5-a]pyrimidine compounds having fungicidal activity.

So far no 6-halogeno-[1,2,4]triazolo[1,5-a]pyrimidines have been described, which are useful for combating animal pests, especially for combating insects, arachnids and/or acaridae.

It has been found that 6-halogeno-[1,2,4]triazolo[1,5-a] pyrimidines of the general formula (I)

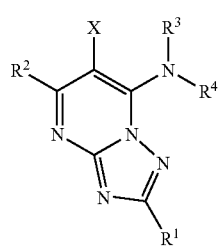

(I)

wherein

X is halogen;

$R^1$ is hydrogen, halogen, OH, CN, $C_1$-$C_{10}$-alkyl, $C_1$-$C_{10}$-haloalkyl, $C_1$-$C_{10}$-alkoxy, $C_1$-$C_6$-alkoxy-$C_1$-$C_6$-alkyl, $C_1$-$C_4$-alkoxy-$C_1$-$C_4$-alkoxy, $C_1$-$C_4$-alkoxy-$C_1$-$C_4$-alkoxy-$C_1$-$C_4$-alkoxy, $C_1$-$C_{10}$-alkylthio, $C_1$-$C_{10}$-alkylsulfinyl, $C_1$-$C_{10}$-alkylsulfonyl, $C_1$-$C_{10}$-alkylamino, di($C_1$-$C_{10}$-alkyl)amino, $C_2$-$C_{10}$-alkenyl, phenyl, phenoxy, benzyloxy, $C_2$-$C_{10}$-alkenyloxy, $C_2$-$C_{10}$-alkynyloxy or $C_2$-$C_{10}$-alkynyl, wherein $C_1$-$C_{10}$-alkylthio, $C_1$-$C_{10}$-alkylsulfinyl and $C_1$-$C_{10}$-alkylsulfonyl may be unsubstituted or partially or completely substituted with halogen and/or may carry a group selected from $C_1$-$C_4$-alkoxy, $C_1$-$C_4$-alkoxycarbonyl or COOH, in particular hydrogen, halogen, $C_1$-$C_{10}$-alkyl, $C_1$-$C_{10}$-haloalkyl, $C_1$-$C_{10}$-alkoxy, $C_1$-$C_6$-alkoxy-$C_1$-$C_6$-alkyl, $C_1$-$C_{10}$-alkylthio, $C_1$-$C_{10}$-alkylsulfinyl, $C_1$-$C_{10}$-alkylsulfonyl, $C_1$-$C_{10}$-alkylamino, di($C_1$-$C_{10}$-alkyl)amino, $C_2$-$C_{10}$-alkenyl or $C_2$-$C_{10}$-alkynyl;

$R^2$ is $C_1$-$C_{10}$-alkyl, $C_1$-$C_{10}$-haloalkyl, $C_1$-$C_6$-alkoxy-$C_1$-$C_6$-alkyl, $C_3$-$C_{10}$-cycloalkyl, $C_2$-$C_{10}$-alkenyl or $C_2$-$C_{10}$-alkynyl;

$R^3$ is hydrogen, $C_1$-$C_{10}$-alkyl, $C_1$-$C_{10}$-haloalkyl, $C_1$-$C_6$-alkoxy-$C_1$-$C_6$-alkyl, $C_1$-$C_{10}$-alkylcarbonyl, $C_1$-$C_{10}$-alkoxycarbonyl or arylcarbonyl;

$R^4$ is $C_3$-$C_{10}$-cycloalkyl, phenyl, naphthyl, 3- to 7-membered heterocyclyl or a radical of the formula -A-$R^{4a}$, it being possible for $C_3$-$C_{10}$-cycloalkyl, phenyl, naphthyl and 3- to 7-membered heterocyclyl to be unsubstituted or to carry 1, 2 or 3 radicals which are selected, independently from each other, from the group consisting of halogen, cyano, nitro, hydroxy, $C_1$-$C_{10}$-alkyl, $C_1$-$C_{10}$-alkoxy, $C_1$-$C_{10}$-haloalkyl, $C_1$-$C_{10}$-haloalkoxy, amino, $C_1$-$C_{10}$-alkylamino, di($C_1$-$C_{10}$-alkyl)amino, $C_1$-$C_{10}$-alkylthio, $C_1$-$C_{10}$-alkylsulfinyl, $C_1$-$C_{10}$-alkylsulfonyl, $C_3$-$C_8$-cycloalkyl, $C_3$-$C_8$-cycloalkyl-$C_1$-$C_4$-alkyl, phenyl, phenyl-$C_1$-$C_4$-alkoxy and phenyloxy, wherein the five last-mentioned radicals for their part may be unsubstituted or may carry one, two or three substituents which are selected, independently from each other, from the group consisting of $C_1$-$C_4$-alkyl, $C_1$-$C_4$-alkoxy and halogen, and wherein heterocyclyl contains 1, 2 or 3 heteroatoms selected, independently from each other, from the group consisting of oxygen, sulfur, nitrogen and a group $NR^5$, it being also possible for $C_3$-$C_{10}$-cycloalkyl, phenyl and 3- to 7-membered heterocyclyl to be fused to a 5- to 7-membered saturated, unsaturated or aromatic carbocyclic ring or to a 5- to 7-membered heterocyclic ring and said fused ring may be unsubstituted or may itself carry one, two, three, four, five or six substituents which are selected, independently from each other from the group consisting of halogen and $C_1$-$C_4$-alkyl; wherein A is a $C_1$-$C_6$-alkylene chain which may comprise one heteroatom selected from the group consisting of oxygen and sulfur;

$R^{4a}$ is $C_3$-$C_{10}$-cycloalkyl, phenyl, naphthyl or 3- to 7-membered heterocyclyl, it being possible for $C_3$-$C_{10}$-cycloalkyl, phenyl, naphthyl and 3- to 7-membered heterocyclyl to be unsubstituted or to carry 1, 2 or 3 radicals which are selected, independently from each other, from the group consisting of halogen, cyano, nitro, hydroxy, $C_1$-$C_{10}$-alkyl, $C_1$-$C_{10}$-alkoxy, $C_1$-$C_{10}$-haloalkyl, $C_1$-$C_{10}$-haloalkoxy, amino, $C_1$-$C_{10}$-alkylamino, di($C_1$-$C_{10}$-alkyl)amino, $C_1$-$C_{10}$-alkylthio, $C_1$-$C_{10}$-alkylsulfinyl, $C_1$-$C_{10}$-alkylsulfonyl, $C_3$-$C_8$-cycloalkyl, $C_3$-$C_8$-cycloalkyl-$C_1$-$C_4$-alkyl, phenyl, phenyl-$C_1$-$C_4$-alkoxy and phenyloxy, wherein the five last-mentioned radicals for their part may be unsubstituted or may carry one, two or three substituents which are selected, independently from each other, from the group consisting of $C_1$-$C_4$-alkyl, $C_1$-$C_4$-alkoxy and halogen, and wherein heterocyclyl contains 1, 2 or 3 heteroatoms selected, independently from each other, from the group consisting of oxygen, sulfur, nitrogen and a group $NR^5$, it being also possible for $C_3$-$C_{10}$-cycloalkyl, phenyl and 3- to 7-membered heterocyclyl to be fused to a 5- to 7-membered saturated, unsaturated or aromatic carbocyclic ring or to a 5- to 7-membered heterocyclic ring and said fused ring may be unsubstituted or may itself carry one, two, three, four, five or six substituents which are selected, independently from each other from the group consisting of halogen and $C_1$-$C_4$-alkyl; and $R^5$ is hydrogen, $C_1$-$C_6$-alkyl, $C_3$-$C_6$-alkenyl or $C_3$-$C_6$-alkynyl;

and the agriculturally acceptable salts thereof have a high pesticidal activity, especially against difficult to control insects, arachnids and/or acaridae.

Therefore, the present invention relates to the use of the compounds of formula I and of the salts thereof for combating animal pests and also to a method of combating animal pests which comprises contacting the animal pests, their habit, breeding ground, food supply, plant, seed, soil, area, material or environment in which the animal pests are growing or may grow, or the materials, plants, seeds, soils, surfaces or spaces to be protected from animal attack or infestation with a pesticidally effective amount of at least one 6-halogeno-[1,2,4]-triazolo[1,5-a]-pyrimidine of the general formula I and/or at least one agriculturally acceptable salt thereof.

The 6-halogeno-[1,2,4]-triazolo[1,5-a]-pyrimidine of the general formula I as defined herein and the agriculturally acceptable salts thereof are particularly useful for combating animal pests which are harmful to crops. Therefore the present invention also relates to the use of the compounds of the general formula I for protecting crops from attack or infestation by animal pests. Thus, the present invention provides a method for protecting crops from attack or infestation by animal pests which comprises contacting a crop with a pesticidally effective amount of a 6-halogeno-[1,2,4]-triazolo[1,5-a]-pyrimidine of the general formula I and/or at least one salt thereof.

The invention also relates to 6-halogeno-[1,2,4]triazolo[1,5-a]pyrimidine compounds of the general formula I

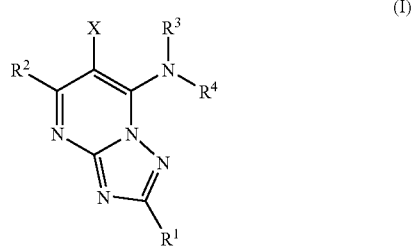

(I)

wherein X, $R^1$, $R^2$, $R^3$ and $R^4$ are as defined above provided that A in the radical A-$R^{4a}$ is a $C_2$-$C_6$-alkylene chain which is attached to the nitrogen atom via a secondary or tertiary carbon atom of the alkylene chain and said $C_2$-$C_6$-alkylene chain may comprise one heteroatom selected from the group consisting of oxygen and sulfur; and to the agriculturally useful salts thereof.

Furthermore, the invention relates to agricultural compositions, preferably in the form of directly sprayable solutions, emulsions, pastes oil dispersions, powders, materials for scattering, dusts or in the form of granules, which comprise at least one 6-halogeno-[1,2,4]triazolo[1,5-a]pyrimidine of the general formula I as defined above, admixed with one or more agronomically acceptable inert, solid or liquid carrier(s) and, if desired, at least one surfactant.

In the substituents, the compounds of the general formula I may have for a given constitution different spatial arrangement of the atoms, e.g. they may carry one or more centers of chirality, in which case they are present as mixtures of stereoisomers, such as enantiomers or diastereomers. The present invention provides both the pure stereoisomers, e.g. the pure enantiomes or diastereomers, and mixtures thereof.

Salts of the compounds of the formula I which are suitable for the use according to the invention are especially agriculturally acceptable salts. They can be formed in a customary method, e.g. by reacting the compound with an acid of the anion in question.

Suitable agriculturally useful salts are especially the salts of those cations or the acid addition salts of those acids whose cations and anions, respectively, do not have any adverse effect on the action of the compounds according to the present invention, which are useful for combating harmful insects or arachnids. Thus, suitable cations are in particular the ions of the alkali metals, preferably lithium, sodium and potassium, of the alkaline earth metals, preferably calcium, magnesium and barium, and of the transition metals, preferably manganese, copper, zinc and iron, and also the ammonium ion which may, if desired, carry one to four $C_1$-$C_4$-alkyl substituents and/or one phenyl or benzyl substituent, preferably diisopropylammonium, tetramethylammonium, tetrabutylammonium, trimethylbenzylammonium, furthermore phosphonium ions, sulfonium ions, preferably tri($C_1$-$C_4$-alkyl) sulfonium, and sulfoxonium ions, preferably tri($C_1$-$C_4$-alkyl) sulfoxonium.

Anions of useful acid addition salts are primarily chloride, bromide, fluoride, hydrogen sulfate, sulfate, dihydrogen phosphate, hydrogen phosphate, phosphate, nitrate, hydrogen carbonate, carbonate, hexafluorosilicate, hexafluorophosphate, benzoate, and the anions of $C_1$-$C_4$-alkanoic acids, preferably formate, acetate, propionate and butyrate. They can be formed by reacting the compounds of the formulae Ia and Ib with an acid of the corresponding anion, preferably of hydrochloric acid, hydrobromic acid, sulfuric acid, phosphoric acid or nitric acid.

The organic moieties mentioned in the above definitions of the variables are—like the term halogen—collective terms for individual listings of the individual group members. The prefix $C_n$-$C_m$ indicates in each case the possible number of carbon atoms in the group.

The term halogen denotes in each case fluorine, bromine, chlorine or iodine, in particular fluorine or chlorine.

Examples of other meanings are:

The term "$C_1$-$C_{10}$-alkyl" as used herein and the alkyl moieties of alkylamino and dialkylamino refer to a saturated straight-chain or branched hydrocarbon group having 1 to 10 carbon atoms, preferably 1 to 6 carbon atoms, especially 1 to 4 carbon groups, for example methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl and their isomers. $C_1$-$C_4$-alkyl means for example methyl, ethyl, propyl, 1-methylethyl, butyl, 1-methylpropyl, 2-methylpropyl or 1,1-dimethylethyl.

The term "$C_1$-$C_6$-alkylene chain which may comprise one heteroatom selected from the group consisting of oxygen and sulfur" as used herein refers, for example, to methanediyl, ethane-1,1-diyl, ethane-1,2-diyl, propane-1,1-diyl, propane-1,2-diyl, propane-1,3-diyl, propane-2,2-diyl, butane-1,1-diyl, butane-1,2-diyl, butane-1,3-diyl, butane-1,4-diyl, 2-methylpropane-1,3-diyl, 2-methylpropane-1,2-diyl, 2-methylpropane-1,1-diyl, 1-methylpropane-1,2-diyl, 1-methylpropane-2,2-diyl, 1-methylpropane-1,1-diyl, pentane-1,1-diyl, pentane-1,2-diyl, pentane-1,3-diyl, pentane-1,5-diyl, pentane-2,3-diyl, pentane-2,2-diyl, 1-methylbutane-1,1-diyl, 1-methylbutane-1,2-diyl, 1-methylbutane-1,3-diyl, 1-methylbutane-1,4-diyl, 2-methylbutane-1,1-diyl, 2-methylbutane-1,2-diyl, 2-methylbutane-1,3-diyl, 2-methylbutane-1,4-diyl, 2,2-dimethylpropane-1,1-diyl, 2,2-dimethylpropane-1,3-diyl, 1,1-dimethylpropane-1,3-diyl, 1,1-dimethylpropane-1,2-diyl, 2,3-dimethylpropane-1,3-diyl, 2,3-dimethylpropane-1,2-diyl, 1,3-dimethylpropane-1,3-diyl, hexane-1,1-diyl, hexane-1,2-diyl, hexane-1,3-diyl, hexane-1,4-diyl, hexane-1,5-diyl, hexane-1,6-diyl, hexane-2,5-diyl, 2-methylpentane-1,1-diyl, 1-methylpentane-1,2-diyl, 1-methylpentane-1,3-diyl, 1-methylpentane-1,4-diyl, 1-methylpentane-1,5-diyl, 2-methylpentane-1,1-diyl, 2-methylpentane-1,2-diyl, 2-methylpentane-1,3-diyl, 2-methylpentane-1,4-diyl, 2-methylpentane-1,5-diyl, 3-methylpentane-1,1-diyl, 3-methylpentane-1,2-diyl, 3-methylpentane-1,3-diyl, 3-methylpentane-1,4-diyl, 3-methylpentane-1,5-diyl, 1,1-dimethylbutane-1,2-diyl, 1,1-dimethylbutane-1,3-diyl, 1,1-dimethylbutane-1,4-diyl, 1,2-dimethylbutane-1,1-diyl, 1,2-dimethylbutane-1,2-diyl, 1,2-dimethylbutane-1,3-diyl, 1,2-dimethylbutane-1,4-diyl, 1,3-dimethylbutane-1,1-diyl, 1,3-dimethylbutane-1,2-diyl, 1,3-dimethylbutane-1,3-diyl, 1,3-dimethylbutane-1,4-diyl, 1-ethylbutane-1,1-diyl, 1-ethylbutane-1,2-diyl, 1-ethylbutane-1,3-diyl, 1-ethylbutane-1,4-diyl, 2-ethylbutane-1,1-diyl, 2-ethylbutane-1,2-diyl, 2-ethylbutane-1,3-diyl, 2-ethylbutane-1,4-diyl, 2-ethylbutane-2,3-diyl, 2,2-dimethylbutane-1,1-diyl, 2,2-dimethylbutane-1,3-diyl, 2,2-dimethylbutane-1,4-diyl, 1-isopropylpropane-1,1-diyl, 1-isopropylpropane-1,2-diyl, 1-isopropylpropane-1,3-diyl, 2-isopropylpropane-1,1-diyl, 2-isopropylpropane-1,2-diyl, 2-isopropylpropane-1,3-diyl, 1,2,3-trimethylpropane-1,1-diyl, 1,2,3-trimethylpropane-1,2-diyl or 1,2,3-trimethylpropane-1,3-diyl, preferably ethane-1,1-diyl or propane-1,1-diyl.

When the $C_1$-$C_6$-alkylene group comprises a heteroatom, the heteroatom can be arranged in the alkylene chain at any position or at the end of the chain so that it connects the alkylene chain to the radical $R^{4a}$. Preferably, the heteroatom is not arranged at the end of the alkylene chain. The heteroatom is preferably oxygen.

The term "$C_1$-$C_{10}$-haloalkyl" as used herein refers to a straight-chain or branched saturated alkyl group having 1 to 10 carbon atoms (as mentioned above), where some or all of the hydrogen atoms in these groups may be replaced by halogen atoms as mentioned above, for example $C_1$-$C_4$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and the like.

The term "$C_1$-$C_2$-fluoroalkyl" as used herein refers to a $C_1$-$C_2$-alkyl which carries 1, 2, 3, 4 or 5 fluorine atoms, for example difluoromethyl, trifluoromethyl, 1-fluoroethyl, 2-fluoroethyl, 2,2-difluoroethyl, 2,2,2-trifluoroethyl, 1,1,2,2-tetrafluoroethyl or pentafluoroethyl.

The term, "$C_1$-$C_{10}$-alkoxy" as used herein refers to a straight-chain or branched saturated alkyl group having 1 to 10 carbon atoms (as mentioned above) which is attached via an oxygen atom. Examples include $C_1$-$C_6$-alkoxy such as methoxy, ethoxy, $OCH_2$—$C_2H_5$, $OCH(CH_3)_2$, n-butoxy, $OCH(CH_3)$—$C_2H_5$, $OCH_2$—$CH(CH_3)_2$, $OC(CH_3)_3$, n-pentoxy, 1-methylbutoxy, 2-methylbutoxy, 3-methylbutoxy, 1,1-dimethylpropoxy, 1,2-dimethylpropoxy, 2,2-dimethyl-propoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy, 1-ethyl-2-methylpropoxy and the like.

The term "$C_1$-$C_{10}$-haloalkoxy" as used herein refers to a $C_1$-$C_{10}$-alkoxy group as mentioned above which is partially or fully substituted by fluorine, chlorine, bromine and/or iodine, i.e., for example, $C_1$-$C_6$-haloalkoxy such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy, nonafluorobutoxy, 5-fluoro-1-pentoxy, 5-chloro-1-pentoxy, 5-bromo-1-pentoxy, 5-iodo-1-pentoxy, 5,5,5-trichloro-1-pentoxy, undecafluoropentoxy, 6-fluoro-1-hexoxy, 6-chloro-1-hexoxy, 6-bromo-1-hexoxy, 6-iodo-1-hexoxy, 6,6,6-trichloro-1-hexoxy or dodecafluorohexoxy, in particular chloromethoxy, fluoromethoxy, difluoromethoxy, trifluoromethoxy, 2-fluoroethoxy, 2-chloroethoxy or 2,2,2-trifluoroethoxy.

The term "$C_1$-$C_6$-alkoxy-$C_1$-$C_6$-alkyl" as used herein refers to $C_1$-$C_6$-alkyl which is substituted by $C_1$-$C_6$-alkoxy as mentioned above, i.e., for example, $CH_2$—$OCH_3$, $CH_2$—$OC_2H_5$, n-propoxymethyl, $CH_2$—$OCH(CH_3)_2$, n-butoxymethyl, (1-methylpropoxy)methyl, (2-methylpropoxy)methyl, $CH_2$—$OC(CH_3)_3$, 2-(methoxy)ethyl, 2-(ethoxy)ethyl, 2-(n-propoxy)ethyl, 2-(1-methylethoxy)ethyl, 2-(n-butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(n-propoxy)propyl, 2-(1-methylethoxy)propyl, 2-(n-butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(n-propoxy)propyl, 3-(1-methylethoxy)propyl, 3-(n-butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(n-propoxy)butyl, 2-(1-methylethoxy)butyl, 2-(n-butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(n-propoxy)butyl, 3-(1-methylethoxy)butyl, 3-(n-butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(n-propoxy)butyl, 4-(1- methylethoxy)butyl, 4-(n-butoxy)butyl, 4-(1-methylpropoxy)butyl, 4-(2-methylpropoxy)butyl, 4-(1,1-dimethylethoxy)butyl and the like.

The term "$C_1$-$C_6$-alkoxy-$C_1$-$C_6$-alkoxy" as used herein refers to $C_1$-$C_6$-alkoxy which is substituted by $C_1$-$C_6$-alkoxy as mentioned above, i.e., for example, OCH—OCH$_3$, OCH$_2$—OC$_2$H$_5$, n-propoxymethoxy, OCH$_1$—OCH(CH$_3$)$_2$, n-butoxymethoxy, (1-methylpropoxy)methoxy, (2-methylpropoxy)methoxy, OCH$_2$—OC(CH$_3$)$_3$, 2-(methoxy)ethoxy, 2-(ethoxy)ethoxy, 2-(n-propoxy)ethoxy, 2-(1-methylethoxy) ethoxy, 2-(n-butoxy)ethoxy, 2-(1-methylpropoxy)ethoxy, 2-(2-methylpropoxy)ethoxy, 2-(1,1-dimethylethoxy)ethoxy, 2-(methoxy)propoxy, 2-(ethoxy)propoxy, 2-(n-propoxy)propoxy, 2-(1-methylethoxy)propoxy, 2-(n-butoxy)propoxy, 2-(1-methylpropoxy)propoxy, 2-(2-methylpropoxy)propoxy, 2-(1,1-dimethylethoxy)propoxy, 3-(methoxy)propoxy, 3-(ethoxy)propoxy, 3-(n-propoxy)propoxy, 3-(1-methylethoxy)propoxy, 3-(n-butoxy)propoxy, 3-(1-methylpropoxy) propoxy, 3-(2-methylpropoxy)propoxy, 3-(1,1-dimethylethoxy)propoxy, 2-(methoxy)butoxy, 2-(ethoxy)butoxy, 2-(n-propoxy)butoxy, 2-(1-methylethoxy)butoxy, 2-(n-butoxy)butoxy, 2-(1-methylpropoxy)butoxy, 2-(2-methylpropoxy)butoxy, 2-(1,1-dimethylethoxy)butoxy, 3-(methoxy) butoxy, 3-(ethoxy)butoxy, 3-(n-propoxy)butoxy, 3-(1-methylethoxy)butoxy, 3-(n-butoxy)butoxy, 3-(1-methylpropoxy)butoxy, 3-(2-methylpropoxy)butoxy, 3-(1,1-dimethylethoxy)butoxy, 4-(methoxy)butoxy, 4-(ethoxy)butoxy, 4-(n-propoxy)butoxy, 4-(1-methylethoxy)butoxy, 4-(n-butoxy)butoxy, 4-(1-methylpropoxy)butoxy, 4-(2-methylpropoxy)butoxy, 4-(1,1-dimethylethoxy)butoxy and the like.

The term "$C_1$-$C_4$-alkoxy-$C_1$-$C_4$-alkoxy-$C_1$-$C_4$-alkoxy" as used herein refers to $C_1$-$C_4$-alkoxy which is substituted by $C_1$-$C_4$-alkoxy-$C_1$-$C_4$-alkoxy as mentioned above, i.e., for example, 2-(2-methoxyethyloxy)ethyloxy, 2-(2-ethoxyethyloxy)ethyloxy;

The term "$C_1$-$C_{10}$-alkylcarbonyl" as used herein refers to a straight-chain or branched saturated alkyl group having 1 to 10 carbon atoms (as mentioned above) bonded via the carbon atom of the carbonyl group at any bond in the alkyl group. Examples include $C_1$-$C_6$-alkylcarbonyl such CO—CH$_3$, CO—C$_2$H$_5$, n-propylcarbonyl, 1-methylethylcarbonyl, n-butylcarbonyl, 1-methylpropylcarbonyl, 2-methylpropylcarbonyl, 1,1-dimethylethylcarbonyl, n-pentylcarbonyl, 1-methylbutylcarbonyl, 2-methylbutylcarbonyl, 3-methylbutylcarbonyl, 1,1-dimethylpropylcarbonyl, 1,2-dimethylpropylcarbonyl, 2,2-dimethylpropylcarbonyl, 1-ethylpropylcarbonyl, n-hexylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-trimethylpropylcarbonyl, 1,2,2-trimethylpropylcarbonyl, 1-ethyl-1-methylpropylcarbonyl or 1-ethyl-2-methylpropylcarbonyl and the like.

The term "$C_1$-$C_{10}$-alkoxycarbonyl" as used herein refers to a straight-chain or branched alkoxy group (as mentioned above) having 1 to 10 carbon atoms attached via the carbon atom of the carbonyl group. Examples include ($C_1$-$C_6$-alkoxy)carbonyl, for example CO—OCH$_3$, CO—OC$_2$H$_5$, COO—CH$_2$—C$_2$H$_5$, CO—OCH(CH$_3$)$_2$, n-butoxycarbonyl, CO—OCH(CH$_3$)—C$_2$H$_5$, CO—OCH$_2$CH(CH$_3$)$_2$, CO—OC(CH$_3$)$_3$, n-pentoxycarbonyl, 1-methylbutoxycarbonyl, 2-methylbutoxycarbonyl, 3-methylbutoxycarbonyl, 2,2-dimethylpropoxycarbonyl, 1-ethylpropoxycarbonyl, n-hexoxycarbonyl, 1,1-dimethylpropoxycarbonyl, 1,2-dimethylpropoxycarbonyl, 1-methylpentoxycarbonyl, 2-methylpentoxycarbonyl, 3-methylpentoxycarbonyl, 4-methylpentoxycarbonyl, 1,1-dimethylbutoxycarbonyl, 1,2-dimethylbutoxycarbonyl, 1,3-dimethylbutoxycarbonyl, 2,2-dimethylbutoxycarbonyl, 2,3-dimethylbutoxycarbonyl, 3,3-dimethylbutoxycarbonyl, 1-ethylbutoxycarbonyl, 2-ethylbutoxycarbonyl, 1,1,2-trimethylpropoxycarbonyl, 1,2,2-trimethylpropoxycarbonyl, 1-ethyl-1-methylpropoxycarbonyl or 1-ethyl-2-methylpropoxycarbonyl The term "$C_1$-$C_{10}$-alkylthio ($C_1$-$C_{10}$-alkylsulfanyl: $C_1$-$C_{10}$-alkyl-S—)" as used herein refers to a straight-chain or branched saturated alkyl group having 1 to 10 carbon atoms (as mentioned above) which is attached via a sulfur atom, for example $C_1$-$C_4$-alkylthio such as methylthio, ethylthio, propylthio, 1-methylethylthio, butylthio, 1-methylpropylthio, 2-methylpropylthio or 1,1-dimethylethylthio.

The term "$C_1$-$C_{10}$-alkylsulfinyl" ($C_1$-$C_{10}$-alkyl-S(=O)—), as used herein refers to a straight-chain or branched saturated hydrocarbon group (as mentioned above) having 1 to 10 carbon atoms bonded through the sulfur atom of the sulfinyl group at any bond in the alkyl group. Examples include $C_1$-$C_6$-alkylsulfinyl: SO—CH$_3$, SO—C$_2$H$_5$, n-propylsulfinyl, 1-methylethylsulfinyl, n-butylsulfinyl, 1-methylpropylsulfinyl, 2-methylpropylsulfinyl, 1,1-dimethylethylsulfinyl, 1-methylbutylsulfinyl, n-pentylsulfinyl, 2-methylbutylsulfinyl, 3-methylbutylsulfinyl, 1,1-dimethylpropylsulfinyl, 1,2-dimethylpropylsulfinyl, 2,2-dimethylpropylsulfinyl, 1-ethylpropylsulfinyl, n-hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl or 1-ethyl-2-methylpropylsulfinyl.

The term "$C_1$-$C_{10}$-alkylsulfonyl" ($C_1$-$C_{10}$-alkyl-S(=O)$_2$—) as used herein refers to a straight-chain or branched saturated alkyl group having 1 to 10 carbon atoms (as mentioned above) which is bonded via the sulfur atom of the sulfonyl group at any bond in the alkyl group. Examples include $C_1$-$C_6$-alkylsulfonyl such as SO$_2$CH$_3$, SO$_2$C$_2$H$_5$, n-propylsulfonyl, SO$_2$—CH(CH$_3$)$_2$, n-butylsulfonyl, 1-methylpropylsulfonyl, 2-methylpropylsulfonyl, SO$_2$—C(CH$_3$)$_3$, n-pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, n-hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl or 1-ethyl-2-methylpropylsulfonyl and the like.

The term "$C_2$-$C_{10}$-alkenyl" as used herein refers to a straight-chain or branched unsaturated hydrocarbon group having 2 to 10 carbon atoms and a double bond in any position, such as ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl; 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3- butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

The term "$C_2$-$C_{10}$-alkynyl" as used herein refers to a straight-chain or branched unsaturated hydrocarbon group having 2 to 10 carbon atoms and containing at least one triple bond, such as ethynyl, prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl and the like.

The term "$C_3$-$C_{10}$-cycloalkyl" as used herein refers to a monocyclic hydrocarbon radical having 3 to 10 carbon atoms, in particular 3 to 8 carbon atoms, e.g. cyclopropyl, cyclobutyl, cyclopentyl, cyclohexyl, cycloheptyl, cyclooctyl, cyclononyl or cyclodecyl, The term "$C_3$-$C_8$-cycloalkyl-$C_1$-$C_4$-alkyl" as used herein refers to a $C_1$-$C_4$-alkyl which carries a $C_3$-$C_8$-cycloalkyl radical as defined above, for example cyclopropylmethyl, 1-cyclopropylethyl, 2-cyclopropylethyl, 1-cyclopropylprop-1-yl, 2-cyclopropylprop-1-yl, 3-cyclopropylprop-1-yl, 1-cyclopropylbut-1-yl, 2-cyclopropylbut-1-yl, 3-cyclopropylbut-1-yl, 4-cyclopropylbut-1-yl, 1-cyclopropylbut-2-yl, 2-cyclopropylbut-2-yl, 3-cyclopropylbut-2-yl, 3-cyclopropylbut-2-yl, 4-cyclopropylbut-2-yl, 1-(cyclopropylmethyl)-eth-1-yl, 1-(cyclopropylmethyl)-1-(methyl)-eth-1-yl, 1-(cyclopropylmethyl)-prop-1-yl, cyclobutylmethyl, 1-cyclobutylethyl, 2-cyclobutylethyl, 1-cyclobutylprop-1-yl, 2-cyclobutylprop-1-yl, 3-cyclobutylprop-1-yl, 1-cyclobutylbut-1-yl, 2-cyclobutylbut-1-yl, 3-cyclobutylbut-1-yl, 4-cyclobutylbut-1-yl, 1-cyclobutylbut-2-yl, 2-cyclobutylbut-2-yl, 3-cyclobutylbut-2-yl, 3-cyclobutylbut-2-yl, 4-cyclobutylbut-2-yl, 1-(cyclobutylmethyl)eth-1-yl, 1-(cyclobutylmethyl)-1-(methyl)-eth-1-yl, 1-(cyclobutylmethyl)prop-1-yl, cyclopentylmethyl, 1-cyclopentylethyl, 2-cyclopentylethyl, 1-cyclopentylprop-1-yl, 2-cyclopentylprop-1-yl, 3-cyclopentylprop-1-yl, 1-cyclopentylbut-1-yl, 2-cyclopentylbut-1-yl, 3-cyclopentylbut-1-yl, 4-cyclopentylbut-1-yl, 1-cyclopentylbut-2-yl, 2-cyclopentylbut-2-yl, 3-cyclopentylbut-2-yl, 3-cyclopentylbut-2-yl, 4-cyclopentylbut-2-yl, 1-(cyclopentylmethyl)-eth-1-yl, 1-(cyclopentylmethyl)-1-(methyl)-eth-1-yl, 1-(cyclopentylmethyl)-prop-1-yl, cyclohexylmethyl, 1-cyclohexylethyl, 2-cyclohexylethyl, 1-cyclohexylprop-1-yl, 2-cyclohexylprop-1-yl, 3-cyclohexylprop-1-yl, 1-cyclohexylbut-1-yl, 2-cyclohexylbut-1-yl, 3-cyclohexylbut-1-yl, 4-cyclohexylbut-1-yl, 1-cyclohexylbut-2-yl, 2-cyclohexylbut-2-yl, 3-cyclohexylbut-2-yl, 3-cyclohexylbut-2-yl, 4-cyclohexylbut-2-yl, 1-(cyclohexylmethyl)-eth-1-yl, 1-(cyclohexylmethyl)-1-(methyl)-eth-1-yl, 1-(cyclohexylmethyl)-prop-1-yl, cycloheptylmethyl, 1-cycloheptylethyl, 2-cycloheptylethyl, 1-cycloheptylprop-1-yl, 2-cycloheptylprop-1-yl, 3-cycloheptylprop-1-yl, 1-cycloheptylbut-1-yl, 2-cycloheptylbut-1-yl, 3-cycloheptylbut-1-yl, 4-cycloheptylbut-1-yl, 1-cycloheptylbut-2-yl, 2-cycloheptylbut-2-yl, 3-cycloheptylbut-2-yl, 3-cycloheptylbut-2-yl, 4-cycloheptylbut-2-yl, 1-(cycloheptylmethyl)-eth-1-yl, 1-(cycloheptylmethyl)-1-(methyl)-eth-1-yl, 1-(cycloheptylmethyl)-prop-1-yl, cyclooctylmethyl, 1-cyclooctylethyl, 2-cyclooctylethyl, 1-cyclooctylprop-1-yl, 2-cyclooctylprop-1-yl, 3-cyclooctylprop-1-yl, 1-cyclooctylbut-1-yl, 2-cyclooctylbut-1-yl, 3-cyclooctylbut-1-yl, 4-cyclooctylbut-1-yl, 1-cyclooctylbut-2-yl, 2-cyclooctylbut-2-yl, 3-cyclooctylbut-2-yl, 3-cyclooctylbut-2-yl, 4-cyclooctylbut-2-yl, 1-(cyclooctylmethyl)-eth-1-yl, 1-(cyclooctylmethyl)-1-(methyl)-eth-1-yl or 1-(cyclooctylmethyl)-prop-1-yl.

The term "phenyl-$C_1$-$C_4$-alkyl" as used herein refers to $C_1$-$C_4$-alkyl which is substituted by phenyl, which may for its part be unsubstituted or carries one, two or three substituents, such as benzyl, 1-phenylethyl, 2-phenylethyl, 1-phenylprop-1-yl, 2-phenylprop-1-yl, 3-phenylprop-1-yl, 1-phenylbut-1-yl, 2-phenylbut-1-yl, 3-phenylbut-1-yl, 4-phenylbut-1-yl, 1-phenylbut-2-yl, 2-phenylbut-2-yl, 3-phenylbut-2-yl, 4-phenylbut-2-yl, 1-(benzyl)eth-1-yl, 1-(benzyl)-1-(methyl)eth-1-yl or 1-(benzyl)-prop-1-yl, preferably benzyl, 1-phenylethyl or 2-phenylethyl and especially (R)-1-phenylethyl and (S)-1-phenylethyl.

The term "heterocyclyl" as used herein refers to a 3- to 7-membered heterocyclic radical which has 3, 4, 5, 6 or 7 ring members, where 1, 2 or 3 of these ring members are heteroatoms selected, independently from each other, from the group consisting of oxygen, nitrogen, sulfur and a group $NR^5$, wherein $R^5$ has the meanings as defined above. The heterocycle may be a carbon-bonded heterocycle or may be bonded via a heteroatom. The heterocycle may be aromatic (heteroaryl) or partially or fully saturated.

Moreover, the heterocyclyl radical may be fused to a 5- to 7-membered saturated, unsaturated or aromatic carbocyclic ring or to a 5- to 7-membered heterocyclic ring which may carry for their part one, two, three, four, five or six substituents which are selected, independently from another from the group consisting of halogen such as fluorine, chlorine, bromine and $C_1$-$C_4$-alkyl such as methyl.

Examples for monocyclic heteroaromatic rings include triazinyl, pyrazinyl, pyrimidyl, pyridazinyl, pyridyl, thienyl, furyl, pyrrolyl, pyrazolyl, imidazolyl, triazolyl, tetrazolyl, thiazolyl, oxazolyl, thiadiazolyl, oxadiazolyl, isothiazolyl or isoxazolyl.

Examples for non-aromatic rings include pyrrolidinyl, pyrazolinyl, imidazolinyl, pyrrolinyl, pyrazolinyl, imidazolinyl, tetrahydrofuranyl, dihydrofuranyl, 1,3-dioxolanyl, dioxolenyl, thiolanyl, dihydrothiophenyl, oxazolidinyl, isoxazolidinyl, oxazolinyl, isoxazolinyl, thiazolinyl, isothiazolinyl, thiazolidinyl, isothiazolidinyl, oxathiolanyl, piperidinyl, piperazinyl, pyranyl, dihydropyranyl, tetrahydropyranyl, dioxanyl, thiopyranyl, dihydrothiopyranyl, tetrahydrothiopyranyl, morpholinyl, thiazinyl and the like.

The term "fused to a 5- to 7-membered saturated, unsaturated or aromatic carbocyclic ring or to a 5- to 7-membered heterocyclic ring" as used herein refers to a cyclic radical which carries a fused saturated $C_5$-$C_7$-carbocycle as defined above, a mono- or diunsaturated $C_5$-$C_7$-carbocycle or phenyl or to a 5-7-membered heterocyclic ring as defined above.

Examples for $C_3$-$C_{10}$-cycloalkyl fused with a 5- to 7-membered saturated, unsaturated or aromatic carbocyclic ring are indan-1-yl, indan-2-yl, 1,2,3,4-tetrahydronaphthalen-1-yl, 1,2,3,4-tetrahydronaphthalen-2-yl, decalin-1-yl, decalin-2-yl or hydrindanyl and the like.

Examples for phenyl fused with a 5- to 7-membered saturated, unsaturated or aromatic carbocyclic ring or to a 5- to 7-membered heterocyclic ring are indan-5-yl, indan-6-yl, dihydronaphthalen-5-yl, dihydronaphthalen-6-yl, 1,2,3,4-tetrahydronaphthalen-5-yl, 1,2,3,4-tetrahydronaphthalen-6-yl, quinolinyl, isoquinolinyl, indolyl, indolizinyl, isoindolyl, indazolyl, benzofuryl, benzthienyl, benzthiazolyl, benzoxazolyl, 1,3-benzodioxolyl, 1,4-benzodioxanyl, benzimidazolyl, dihydroindolyl, dihydroindolizinyl, dihydroisoindolyl, dihydrochinolinyl, dihydroisochinolinyl, chromenyl, chromanyl and the like.

Examples for 3- to 7-membered heterocyclyl carrying a fused-on 5- to 7-membered saturated, unsaturated or aromatic carbocyclic ring or a 5- to 7-membered heterocyclic ring are quinolinyl, isoquinolinyl, indolyl, indolizinyl, isoindolyl, indazolyl, benzofuryl, benzthienyl, benzthiazolyl, benzoxazolyl, 1,3-benzodioxolyl, 1,4-benzodioxanyl, benzimidazolyl, dihydroindolyl, dihydroindolizinyl, dihydroisoindolyl, dihydrochinolinyl, dihydroisochinolinyl, chromenyl, chromanyl and the like.

As regards the pesticidal activity of the 6-halogeno-[1,2,4]-triazolo[1,5-a]-pyrimidine of the general formula I, preference is given to those compounds I, in which the radical $R^4$ is attached to the nitrogen atom of the amino group via a secondary or tertiary carbon atom. Thus, compounds I are preferred, wherein $R^4$ is phenyl, naphthyl, $C_3$-$C_{10}$-cycloalkyl, a 3- to 7-membered heterocyclyl or a radical -A-$R^{4a}$, wherein A $C_2$-$C_6$-alkylene which is attached to the nitrogen via a secondary or tertiary carbon atom of the $C_2$-$C_6$-alkylene chain. The $C_2$-$C_6$-alkylene chain may comprise a heteroatom selected from the group consisting of oxygen and sulfur. The compounds comprise the pure R- and S-enantiomers as well as the mixtures of the enantiomers such as the racemic mixtures. Particularly preferred among these are the pure enantiomers.

As regards the pesticidal activity of the 6-halogeno-[1,2,4]-triazolo[1,5-a]-pyrimidine of the general formula I, preference is also given to the following meaning of the radicals, in each case on their own or in combination:

X is chlorine;

$R^1$ is hydrogen, $C_1$-$C_4$-alkyl, preferably methyl, $C_1$-$C_4$-haloalkyl, preferably trifluoromethyl, $C_1$-$C_4$-alkoxy, preferably methoxy, $C_1$-$C_4$-alkylthio, preferably methylthio, $C_1$-$C_4$-alkylsulfinyl, preferably methylsulfinyl or $C_1$-$C_4$-alkylsulfonyl, preferably methylsulfonyl, most preferred hydrogen; however $R^1$ may also be OH, CN, Phenoxy, Benzyloxy, $C_1$-$C_4$-alkoxy-$C_2$-$C_4$-alkoxy, $C_1$-$C_4$-alkoxy-$C_2$-$C_4$-alkoxy-$C_2$-$C_4$-alkoxy, ($C_1$-$C_4$-alkoxycarbonyl)$C_2$-$C_4$-alkylthio, such as 2-(methoxycarbonyl)ethylthio, 2-(ethoxycarbonyl)ethylthio, $SCH_2$—CO—$OCH_3$ or $SCH_2$—CO—$OCH_2CH_3$, (hydroxycarbonyl)$C_2$-$C_4$-alkylthio, such as S—$CH_2$—COOH, S—$CH_2CH_2$—COOH, ($C_1$-$C_4$-alkoxy)$C_2$-$C_4$-alkylthio such as $SCH_2$—$CH_2$—$OCH_3$ or $SCH_2$—$CH_2$—$OCH_2CH_3$;

$R^2$ is $C_1$-$C_4$-alkyl, preferably $C_1$-$C_2$-alkyl, or $C_1$-$C_4$-haloalkyl, preferably $C_1$-$C_2$-fluoroalkyl; most preferred methyl, ethyl, 2-fluoroethyl or 1-fluoroethyl;

$R^3$ is hydrogen or $C_1$-$C_4$-alkoxy-$C_1$-$C_4$-alkyl, most preferred hydrogen;

$R^4$ is phenyl, phenyl-$C_1$-$C_4$-alkyl or $C_3$-$C_8$-cycloalkyl, wherein each phenyl and $C_3$-$C_8$-cycloalkyl group may be unsubstituted or may carry one or two substituents which are selected, independently from one another, from the group consisting of halogen, $C_1$-$C_4$-alkyl, $C_1$-$C_4$-haloalkyl, $C_1$-$C_4$-haloalkoxy, $C_1$-$C_4$-alkoxy, $C_3$-$C_8$-cycloalkyl-$C_1$-$C_4$-alkyl, phenyl and phenyloxy, wherein the three last-mentioned substituents for their part may be unsubstituted or may carry one or two substituents which are selected, independently from each other, from the group consisting of $C_1$-$C_4$-alkyl, $C_1$-$C_4$-alkoxy and halogen.

A preferred embodiment of the invention are compounds of the general formula I, wherein $R^4$ is cyclohexyl, benzyl, 1-phenylethyl or 2-phenylethyl, wherein the cyclohexyl group and the phenyl group in the last three mentioned radicals may be unsubstituted or may carry one or two substituents which are selected, independently from each other, from the group consisting of halogen, $C_1$-$C_4$-alkyl, $C_1$-$C_4$-haloalkoxy, $C_1$-$C_4$-haloalkyl, $C_1$-$C_4$-alkoxy, $C_3$-$C_8$-cycloalkyl, $C_3$-$C_8$-cycloalkyl-$C_1$-$C_4$-alkyl, phenyl and phenyloxy, wherein the two last mentioned substituents for their part may be unsubstituted or may carry one or two substituents which are selected independently of each other from the group consisting of $C_1$-$C_4$-alkyl, $C_1$-$C_4$-alkoxy and halogen.

In an especially preferred embodiment of the present invention, $R^4$ is a cyclohexyl radical which may carry one or two substituents. One substituent is preferably attached to the 4-position of the cyclohexyl radical. Particularly preferred substituents of the radical cyclohexyl mentioned for $R^4$ are, independently of one another, $C_1$-$C_4$-alkyl, especially methyl, ethyl, isopropyl, sec-butyl and tert-butyl or cyclohexyl-$C_1$-$C_4$-alkyl. Amongst the compounds I those are especially preferred, wherein the cyclohexyl radical carries a substituent in the 4-position, said substituent is most preferably attached cis relative to the nitrogen atom.

In another embodiment of the present invention, particular preference is given to 6-halogeno-[1,2,4]triazolo[1,5-a]pyrimidines in which $R^4$ is phenyl, benzyl, 1-phenylethyl or 2-phenylethyl which for their part carry one or two of the above defined substituents on the phenyl ring.

The substituents are preferably selected independently of each other from the group consisting of fluorine, chlorine, bromine, $C_1$-$C_4$-alkyl especially methyl, ethyl, n-propyl, isopropyl, 2-butyl and tert-butyl; $C_1$-$C_4$-alkoxy, especially methoxy, ethoxy, tert-butoxy, $C_1$-$C_4$-haloalkyl, especially trifluoromethyl and $C_1$-$C_4$-haloalkoxy, especially trifluorodifluoromethoxy, trifluoromethoxy, 1,1,2,2-tetrafluoroethoxy. In this embodiment, compounds are especially preferred, wherein $R^4$ is 1-phenylethyl which carries at least one substituent as defined above, especially one which has been indicated as preferred. Most preferably said substituent is attached in the 4-position of the phenyl radical. Particularly preferred among these are compounds I in which $R^4$ is the pure enantiomer or a racemic mixture.

In another embodiment of the invention the radical $R^4$ comprises a phenyl group such as in phenyl, benzyl and 1- or -2-phenylethyl, wherein the phenyl ring carries at least one substituent which is selected from the group consisting of phenyl, cyclohexyl and phenoxy which for their part may be unsubstituted or may carry in the 2-, 3- or 4-position one or two substituents selected from the group consisting of $C_1$-$C_4$-alkyl, especially methyl, ethyl, n-propyl or isopropyl, $C_1$-$C_4$-alkoxy such as methoxy and halogen, especially fluorine, chlorine or bromine. Examples of substituents on the phenyl ring of phenyl, benzyl, 1-phenylethyl, or 2-phenylethyl are: 4-methylphenoxy, 4-ethylphenoxy, 4-isopropylphenoxy, 4-tert-butylphenoxy, 4-fluorophenoxy, 4-chlorophenoxy, 4-bromophenoxy, 2-methylphenoxy, 2-tert-butylphenoxy, 2-ethylphenoxy, 3-ethylphenoxy, 2-bromophenoxy, 2-chlorophenoxy, 3-chlorophenoxy, 3-bromophenoxy, 3,4-difluorophenoxy, 3-chloro-4-fluorophenoxy, 4-bromo-3-chlorophenoxy, 4-chloro-3-fluorophenoxy, 3,4-dichlorophenoxy, 3,4-dimethlyphenoxy, 3-chloro-4-methylphenoxy, 3-methyl-4-chlorophenoxy or 3-methyl-4-bromophenoxy.

Examples of compounds are the 6-chloro-[1,2,4]triazolo-[1,5-a]pyrimidines of the formula Ia (≡I where X═Cl and $R^1$═$R^3$═H), where $R^2$ and $R^4$ together have the meanings given in one row of Table A.

TABLE A

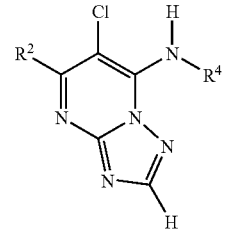

(Ia)

| No. | $R^2$ | $R^4$ |
|---|---|---|
| A-1. | $CH_3$ | 4-$CH_3$-cyclohexyl- |
| A-2. | $CH_3$ | cis-4-$CH_3$-cyclohexyl- |
| A-3. | $CH_3$ | trans-4-$CH_3$-cyclohexyl- |
| A-4. | $CH_3$ | 4-$C_2H_5$-cyclohexyl- |
| A-5. | $CH_3$ | cis-4-$C_2H_5$-cyclohexyl- |
| A-6. | $CH_3$ | trans-4-$C_2H_5$-cyclohexyl- |
| A-7. | $CH_3$ | 4-n-propyl-cyclohexyl- |
| A-8. | $CH_3$ | cis-4-n-propyl-cyclohexyl- |
| A-9. | $CH_3$ | trans-4-n-propyl-cyclohexyl- |
| A-10. | $CH_3$ | 4-isopropyl-cyclohexyl- |
| A-11. | $CH_3$ | cis-4-isopropyl-cyclohexyl- |
| A-12. | $CH_3$ | trans-4-isopropyl-cyclohexyl- |
| A-13. | $CH_3$ | 4-n-butylcyclohexyl- |
| A-14. | $CH_3$ | cis-4-n-butylcyclohexyl- |
| A-15. | $CH_3$ | trans-4-n-butylcyclohexyl- |
| A-16. | $CH_3$ | 4-tert-butylcyclohexyl- |
| A-17. | $CH_3$ | cis-4-tert-butylcyclohexyl- |
| A-18. | $CH_3$ | trans-4-tert-butylcyclohexyl- |
| A-19. | $CH_3$ | 4-(2-butyl)cyclohexyl- |
| A-20. | $CH_3$ | cis-4-(2-butyl)cyclohexyl- |
| A-21. | $CH_3$ | trans-4-(2-butyl)cyclohexyl- |
| A-22. | $CH_3$ | 4-(cyclohexyl-C($CH_3$)$_2$)-cyclohexyl- |
| A-23. | $CH_3$ | cis-4-(cyclohexyl-C($CH_3$)$_2$)-cyclohexyl- |
| A-24. | $CH_3$ | trans-4-(cyclohexyl-C($CH_3$)$_2$)-cyclohexyl- |
| A-25. | $CH_3$ | $C_6H_5$— |
| A-26. | $CH_3$ | 4-F—$C_6H_4$— |
| A-27. | $CH_3$ | 4-Cl—$C_6H_4$— |
| A-28. | $CH_3$ | 4-Br—$C_6H_4$— |
| A-29. | $CH_3$ | 4-($C_6H_5$)—$C_6H_4$— |
| A-30. | $CH_3$ | 4-phenoxyphenyl |
| A-31. | $CH_3$ | benzyl |
| A-32. | $CH_3$ | 4-$CH_3$—$C_6H_4$—$CH_2$— |
| A-33. | $CH_3$ | 4-$C_2H_5$—$C_6H_4$—$CH_2$— |
| A-34. | $CH_3$ | 4-n-$C_3H_7$—$C_6H_4$—$CH_2$— |
| A-35. | $CH_3$ | 4-isopropyl-$C_6H_4$—$CH_2$— |
| A-36. | $CH_3$ | 4-n-$C_4H_9$—$C_6H_4$—$CH_2$— |
| A-37. | $CH_3$ | 4-isobutyl-$C_6H_4$—$CH_2$— |
| A-38. | $CH_3$ | 4-tert-buyl-$C_6H_4CH_2$— |
| A-39. | $CH_3$ | 4-$F_3C$—$C_6H_4CH_2$— |
| A-40. | $CH_3$ | 4-methoxy-$C_6H_4CH_2$— |
| A-41. | $CH_3$ | 4-ethoxy-$C_6H_4CH_2$— |
| A-42. | $CH_3$ | 4-n-propoxy-$C_6H_4CH_2$— |
| A-43. | $CH_3$ | 4-isopropoxy-$C_6H_4CH_2$— |
| A-44. | $CH_3$ | 4-n-butoxy-$C_6H_4CH_2$— |
| A-45. | $CH_3$ | 4-tert-butoxy-$C_6H_4CH_2$— |
| A-46. | $CH_3$ | 4-F—$C_6H_4CH_2$— |
| A-47. | $CH_3$ | 4-Cl—$C_6H_4CH_2$— |
| A-48. | $CH_3$ | 4-Br—$C_6H_4CH_2$— |
| A-49. | $CH_3$ | 3,4-$F_2$—$C_6H_3CH_2$— |
| A-50. | $CH_3$ | 3,4-$Cl_2$—$C_6H_3CH_2$— |
| A-51. | $CH_3$ | 3,4-$Br_2$—$C_6H_3CH_2$— |
| A-52. | $CH_3$ | 4-(4-$CH_3$—$C_6H_4$—O)—$C_6H_4$—$CH_2$— |
| A-53. | $CH_3$ | 4-(4-$C_2H_5$—$C_6H_4$—O)—$C_6H_4$—$CH_2$— |
| A-54. | $CH_3$ | 4-(4-n-$C_3H_7$—$C_6H_4$—O)—$C_6H_4$—$CH_2$— |
| A-55. | $CH_3$ | 4-(4-iso-$C_3H_7$—$C_6H_4$—O)—$C_6H_4$—$CH_2$— |
| A-56. | $CH_3$ | 4-(4-n-$C_4H_9$—$C_6H_4$—O)—$C_6H_4$—$CH_2$— |
| A-57. | $CH_3$ | 4-(4-iso-$C_4H_9$—$C_6H_4$—O)—$C_6H_4$—$CH_2$— |

TABLE A-continued

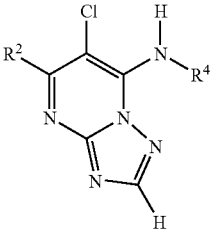

(Ia)

| No. | R² | R⁴ |
|---|---|---|
| A-58. | CH₃ | 4-(4-tert-C₄H₉—C₆H₄—O)—C₆H₄—CH₂— |
| A-59. | CH₃ | 4-(4-H₃C—O—C₆H₄—O)—C₆H₄—CH₂— |
| A-60. | CH₃ | 4-(4-H₃C—H₂C—O—C₆H₄—O)—C₆H₄—CH₂— |
| A-61. | CH₃ | 4-(4-H₃C—H₂C—H₂C—O—C₆H₄—O)—C₆H₄—CH₂— |
| A-62. | CH₃ | 4-(4-H₃C—H₂C—H₂C—H₂C—O—C₆H₄—O)—C₆H₄—CH₂— |
| A-63. | CH₃ | 4-(4-tert-butoxy-C₆H₄—O)—C₆H₄—CH₂— |
| A-64. | CH₃ | 4-(4-Cl—C₆H₄—O)—C₆H₄—CH₂— |
| A-65. | CH₃ | 4-(4-Br—C₆H₄—O)—C₆H₄—CH₂— |
| A-66. | CH₃ | 4-(3-CH₃—C₆H₄—O)—C₆H₄—CH₂— |
| A-67. | CH₃ | 4-(3-C₂H₅—C₆H₄—O)—C₆H₄—CH₂— |
| A-68. | CH₃ | 4-(3-n-C₃H₇—C₆H₄—O)—C₆H₄—CH₂— |
| A-69. | CH₃ | 4-(3-iso-C₃H₇—C₆H₄—O)—C₆H₄—CH₂— |
| A-70. | CH₃ | 4-(3-n-C₄H₉—C₆H₄—O)—C₆H₄—CH₂— |
| A-71. | CH₃ | 4-(3-iso-C₄H₉—C₆H₄—O)—C₆H₄—CH₂— |
| A-72. | CH₃ | 4-(3-tert-butyl-C₆H₄—O)—C₆H₄—CH₂— |
| A-73. | CH₃ | 4-(3-H₃C—O—C₆H₄—O)—C₆H₄—CH₂— |
| A-74. | CH₃ | 4-(3-H₃C—H₂C—O—C₆H₄—O)—C₆H₄—CH₂— |
| A-75. | CH₃ | 4-(3-H₃C—H₂C—H₂C—O—C₆H₄—O)—C₆H₄—CH₂— |
| A-76. | CH₃ | 4-(3-H₃C—H₂C—H₂C—H₂C—O—C₆H₄—O)—C₆H₄—CH₂— |
| A-77. | CH₃ | 4-(3-tert-butoxy-C₆H₄—O)—C₆H₄—CH₂— |
| A-78. | CH₃ | 4-(3-F—C₆H₄—O)—C₆H₄—CH₂— |
| A-79. | CH₃ | 4-(3-Cl—C₆H₄—O)—C₆H₄—CH₂— |
| A-80. | CH₃ | 4-(3-Br—C₆H₄—O)—C₆H₄—CH₂— |
| A-81. | CH₃ | 4-(2-CH₃—C₆H₄—O)—C₆H₄—CH₂— |
| A-82. | CH₃ | 4-(2-C₂H₅—C₆H₄—O)—C₆H₄—CH₂— |
| A-83. | CH₃ | 4-(2-n-C₃H₇—C₆H₄—O)—C₆H₄—CH₂— |
| A-84. | CH₃ | 4-(2-iso-C₃H₇—C₆H₄—O)—C₆H₄—CH₂— |
| A-85. | CH₃ | 4-(2-n-C₄H₉—C₆H₄—O)—C₆H₄—CH₂— |
| A-86. | CH₃ | 4-(2-iso-C₄H₉—C₆H₄—O)—C₆H₄—CH₂— |
| A-87. | CH₃ | 4-(2-tert-butyl-C₆H₄—O)—C₆H₄—CH₂— |
| A-88. | CH₃ | 4-(2-H₃C—O—C₆H₄—O)—C₆H₄—CH₂— |
| A-89. | CH₃ | 4-(2-H₃C—H₂C—O—C₆H₄—O)—C₆H₄—CH₂— |
| A-90. | CH₃ | 4-(2-H₃C—H₂C—H₂C—O—C₆H₄—O)—C₆H₄—CH₂— |
| A-91. | CH₃ | 4-(2-H₃C—H₂C—H₂C—H₂C—O—C₆H₄—O)—C₆H₄—CH₂— |
| A-92. | CH₃ | 4-(2-tert-butoxy-C₆H₄—O)—C₆H₄—CH₂— |
| A-93. | CH₃ | 4-(2-F—C₆H₄—O)—C₆H₄—CH₂— |
| A-94. | CH₃ | 4-(2-Cl—C₆H₄—O)—C₆H₄—CH₂— |
| A-95. | CH₃ | 4-(2-Br—C₆H₄—O)—C₆H₄—CH₂— |
| A-96. | CH₃ | 4-(3,4-F₂—C₆H₃—O)—C₆H₄—CH₂— |
| A-97. | CH₃ | 4-(3,4-Cl₂—C₆H₃—O)—C₆H₄—CH₂— |
| A-98. | CH₃ | 4-(3,4-(CH₃)₂—C₆H₃—O)—C₆H₄—CH₂— |
| A-99. | CH₃ | 4-(3-F-4-Cl—C₆H₃—O)—C₆H₄—CH₂— |
| A-100. | CH₃ | 4-(3-Cl-4-F—C₆H₃—O)—C₆H₄—CH₂— |
| A-101. | CH₃ | 4-(3-CH₃-4-Cl—C₆H₃—O)—C₆H₄—CH₂— |
| A-102. | CH₃ | 4-(3-Cl-4-CH₃—C₆H₃—O)—C₆H₄—CH₂— |
| A-103. | CH₃ | 4-(3-Cl-4-Br—C₆H₃—O)—C₆H₄—CH₂— |
| A-104. | CH₃ | 4-(3-CH₃-4-Br—C₆H₃—O)—C₆H₄—CH₂— |
| A-105. | CH₃ | (±) phenyl-CH(CH₃)— |
| A-106. | CH₃ | (R) phenyl-CH(CH₃)— |
| A-107. | CH₃ | (S) phenyl-CH(CH₃)— |
| A-108. | CH₃ | (±) 4-F-phenyl-CH(CH₃)— |
| A-109. | CH₃ | (R) 4-F-phenyl-CH(CH₃)— |
| A-110. | CH₃ | (S) 4-F-phenyl-CH(CH₃)— |
| A-111. | CH₃ | (±) 4-Cl-phenyl-CH(CH₃)— |
| A-112. | CH₃ | (R) 4-Cl-phenyl-CH(CH₃)— |
| A-113. | CH₃ | (S) 4-Cl-phenyl-CH(CH₃)— |
| A-114. | CH₃ | (±) 4-Br-phenyl-CH(CH₃)— |
| A-115. | CH₃ | (R) 4-Br-phenyl-CH(CH₃)— |
| A-116. | CH₃ | (S) 4-Br-phenyl-CH(CH₃)— |
| A-117. | CH₃ | (±) 4-Cl-2-F-phenyl-CH(CH₃)— |
| A-118. | CH₃ | (R) 4-Cl-2-F-phenyl-CH(CH₃)— |
| A-119. | CH₃ | (S) 4-Cl-2-F-phenyl-CH(CH₃)— |
| A-120. | CH₃ | (±) 6-Cl-2-F-phenyl-CH(CH₃)— |
| A-121. | CH₃ | (R) 6-Cl-2-F-phenyl-CH(CH₃)— |
| A-122. | CH₃ | (S) 6-Cl-2-F-phenyl-CH(CH₃)— |

TABLE A-continued

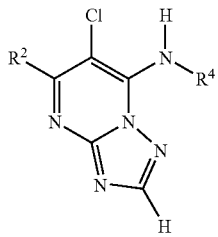

(Ia)

| No. | $R^2$ | $R^4$ |
|---|---|---|
| A-123. | $CH_3$ | (±) 2-F-phenyl-CH($CH_3$)— |
| A-124. | $CH_3$ | (R) 2-F-phenyl-CH($CH_3$)— |
| A-125. | $CH_3$ | (S) 2-F-phenyl-CH($CH_3$)— |
| A-126. | $CH_3$ | (S) 2,4-$F_2$-phenyl-CH($CH_3$)— |
| A-127. | $CH_3$ | (±) 2,4-$F_2$-phenyl-CH($CH_3$)— |
| A-128. | $CH_3$ | (R) 2,4-$F_2$-phenyl-CH($CH_3$)— |
| A-129. | $CH_3$ | (S) 2,5-$F_2$-phenyl-CH($CH_3$)— |
| A-130. | $CH_3$ | (±) 2,5-$F_2$-phenyl-CH($CH_3$)— |
| A-131. | $CH_3$ | (R) 2,5-$F_2$-phenyl-CH($CH_3$)— |
| A-132. | $CH_3$ | (S) 2,6-$F_2$-phenyl-CH($CH_3$)— |
| A-133. | $CH_3$ | (±) 2,6-$F_2$-phenyl-CH($CH_3$)— |
| A-134. | $CH_3$ | (R) 2,6-$F_2$-phenyl-CH($CH_3$)— |
| A-135. | $CH_3$ | (±) 2-$CH_3$O-phenyl-CH($CH_3$)— |
| A-136. | $CH_3$ | (R) 2-$CH_3$O-phenyl-CH($CH_3$)— |
| A-137. | $CH_3$ | (S) 2-$CH_3$O-phenyl-CH($CH_3$)— |
| A-138. | $CH_3$ | (±) 4-$CH_3$O-phenyl-CH($CH_3$)— |
| A-139. | $CH_3$ | (R) 4-$CH_3$O-phenyl-CH($CH_3$)— |
| A-140. | $CH_3$ | (S) 4-$CH_3$O-phenyl-CH($CH_3$)— |
| A-141. | $CH_3$ | (±) 4-$H_5C_2$—O-phenyl-CH($CH_3$)— |
| A-142. | $CH_3$ | (R) 4-$H_5C_2$—O-phenyl-CH($CH_3$)— |
| A-143. | $CH_3$ | (S) 4-$H_5C_2$—O-phenyl-CH($CH_3$)— |
| A-144. | $CH_3$ | (±) 4-n-propoxy-phenyl-CH($CH_3$)— |
| A-145. | $CH_3$ | (R) 4-n-propoxy-phenyl-CH($CH_3$)— |
| A-146. | $CH_3$ | (S) 4-n-propoxy-phenyl-CH($CH_3$)— |
| A-147. | $CH_3$ | (±) 4-n-butoxy-phenyl-CH($CH_3$)— |
| A-148. | $CH_3$ | (R) 4-n-butoxyx-phenyl-CH($CH_3$)— |
| A-149. | $CH_3$ | (S) 4-n-butoxyphenyl-CH($CH_3$)— |
| A-150. | $CH_3$ | (±) 4-tert-butoxy-phenyl-CH($CH_3$)— |
| A-151. | $CH_3$ | (R) 4-tert-butoxyx-phenyl-CH($CH_3$)— |
| A-152. | $CH_3$ | (S) 4-tert-butoxyphenyl-CH($CH_3$)— |
| A-153. | $CH_3$ | (±) 4-$CH_3$-phenyl-CH($CH_3$)— |
| A-154. | $CH_3$ | (R) 4-$CH_3$-phenyl-CH($CH_3$)— |
| A-155. | $CH_3$ | (S) 4-$CH_3$-phenyl-CH($CH_3$)— |
| A-156. | $CH_3$ | (±) 4-$C_2H_5$-phenyl-CH($CH_3$)— |
| A-157. | $CH_3$ | (R) 4-$C_2H_5$-phenyl-CH($CH_3$)— |
| A-158. | $CH_3$ | (S) 4-$C_2H_5$-phenyl-CH($CH_3$)— |
| A-159. | $CH_3$ | (±) 4-n-$C_3H_7$-phenyl-CH($CH_3$)— |
| A-160. | $CH_3$ | (R) 4-n-$C_3H_7$-phenyl-CH($CH_3$)— |
| A-161. | $CH_3$ | (S) 4-n-$C_3H_7$-phenyl-CH($CH_3$)— |
| A-162. | $CH_3$ | (±) 4-iso-$C_3H_7$-phenyl-CH($CH_3$)— |
| A-163. | $CH_3$ | (R) 4-iso-$C_3H_7$-phenyl-CH($CH_3$)— |
| A-164. | $CH_3$ | (S) 4-iso-$C_3H_7$-phenyl-CH($CH_3$)— |
| A-165. | $CH_3$ | (±) 4-n-$C_4H_9$-phenyl-CH($CH_3$)— |
| A-166. | $CH_3$ | (R) 4-n-$C_4H_9$-phenyl-CH($CH_3$)— |
| A-167. | $CH_3$ | (S) 4-n-$C_4H_9$-phenyl-CH($CH_3$)— |
| A-168. | $CH_3$ | (±) 4-tert-$C_4H_9$-phenyl-CH($CH_3$)— |
| A-169. | $CH_3$ | (R) 4-tert-$C_4H_9$-phenyl-CH($CH_3$)— |
| A-170. | $CH_3$ | (S) 4-tert-$C_4H_9$-phenyl-CH($CH_3$)— |
| A-171. | $CH_3$ | (±) 4-cycl.-$C_6H_{11}$-phenyl-CH($CH_3$)— |
| A-172. | $CH_3$ | (R) 4-cycl.-$C_6H_{11}$-phenyl-CH($CH_3$)— |
| A-173. | $CH_3$ | (S) 4-cycl.-$C_6H_{11}$-phenyl-CH($CH_3$)— |
| A-174. | $CH_3$ | (±) 4-$OCF_3$-phenyl-CH($CH_3$)— |
| A-175. | $CH_3$ | (R) 4-$OCF_3$-phenyl-CH($CH_3$)— |
| A-176. | $CH_3$ | (S) 4-$OCF_3$-phenyl-CH($CH_3$)— |
| A-177. | $CH_3$ | (±) 4-$CF_3$-phenyl-CH($CH_3$)— |
| A-178. | $CH_3$ | (R) 4-$CF_3$-phenyl-CH($CH_3$)— |
| A-179. | $CH_3$ | (S) 4-$CF_3$-phenyl-CH($CH_3$)— |
| A-180. | $CH_3$ | (±) 3-F-phenyl-CH($CH_3$)— |
| A-181. | $CH_3$ | (R) 3-F-phenyl-CH($CH_3$)— |
| A-182. | $CH_3$ | (S) 3-F-phenyl-CH($CH_3$)— |
| A-183. | $CH_3$ | (±) 3-Cl-phenyl-CH($CH_3$)— |
| A-184. | $CH_3$ | (R) 3-Cl-phenyl-CH($CH_3$)— |
| A-185. | $CH_3$ | (S) 3-Cl-phenyl-CH($CH_3$)— |
| A-186. | $CH_3$ | (±) 3-Br-phenyl-CH($CH_3$)— |
| A-187. | $CH_3$ | (R) 3-Br-phenyl-CH($CH_3$)— |

TABLE A-continued

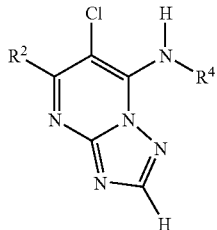

(Ia)

| No. | R² | R⁴ |
|---|---|---|
| A-188. | CH₃ | (S) 3-Br-phenyl-CH(CH₃)— |
| A-189. | CH₃ | (±) 3-CF₃-phenyl-CH(CH₃)— |
| A-190. | CH₃ | (R) 3-CF₃-phenyl-CH(CH₃)— |
| A-191. | CH₃ | (S) 3-CF₃-phenyl-CH(CH₃)— |
| A-192. | CH₃ | (±) 3,4-F₂-phenyl-CH(CH₃)— |
| A-193. | CH₃ | (R) 3,4-F₂-phenyl-CH(CH₃)— |
| A-194. | CH₃ | (S) 3,4-F₂-phenyl-CH(CH₃)— |
| A-195. | CH₃ | (±) 3,4-Cl₂-phenyl-CH(CH₃)— |
| A-196. | CH₃ | (R) 3,4-Cl₂-phenyl-CH(CH₃)— |
| A-197. | CH₃ | (S) 3,4-Cl₂-phenyl-CH(CH₃)— |
| A-198. | CH₃ | (±) 3,4-Br₂-phenyl-CH(CH₃)— |
| A-199. | CH₃ | (R) 3,4-Br₂-phenyl-CH(CH₃)— |
| A-200. | CH₃ | (S) 3,4-Br₂-phenyl-CH(CH₃)— |
| A-201. | CH₃ | (±) 4-Difluoromethoxyphenyl-CH(CH₃)— |
| A-202. | CH₃ | (R) 4-Difluoromethoxyphenyl-CH(CH₃)— |
| A-203. | CH₃ | (S) 4-Difluoromethoxyphenyl-CH(CH₃)— |
| A-204. | CH₃ | (±) 4-(1,1,2,2-tetrafluoroethoxy)phenyl-CH(CH₃)— |
| A-205. | CH₃ | (R) 4-(1,1,2,2-tetrafluoroethoxy)phenyl-CH(CH₃)— |
| A-206. | CH₃ | (S) 4-(1,1,2,2-tetrafluoroethoxy)phenyl-CH(CH₃)— |
| A-207. | CH₃ | (±) (5,5,7,7-tetramethylindan-2-yl)-CH(CH₃)— |
| A-208. | CH₃ | (R) (5,5,7,7-tetramethylindan-2-yl)-CH(CH₃)— |
| A-209. | CH₃ | (S) (5,5,7,7-tetramethylindan-2-yl)-CH(CH₃)— |
| A-210. | CH₃ | (±) (1,1,4,4,-tetramethyl-1,2,3,4-tetrahydronaphthalin-6-yl)-CH(CH₃)— |
| A-211. | CH₃ | (R) (1,1,4,4,-tetramethyl-1,2,3,4-tetrahydronaphthalin-6-yl)-CH(CH₃)— |
| A-212. | CH₃ | (S) (1,1,4,4,-tetramethyl-1,2,3,4-tetrahydronaphthalin-6-yl)-CH(CH₃)— |
| A-213. | CH₃ | (±) (1,1-dimethyl-1,2,3,4-tetrahydronaphthalin-6-yl)-CH(CH₃)— |
| A-214. | CH₃ | (R) (1,1-dimethyl-1,2,3,4-tetrahydronaphthalin-6-yl)-CH(CH₃)— |
| A-215. | CH₃ | (S) (1,1-dimethyl-1,2,3,4-tetrahydronaphthalin-6-yl)-CH(CH₃)— |
| A-216. | CH₃ | (±) (1,1,4,4,7-pentamethyl-1,2,3,4-tetrahydronaphthalin-6-yl)-CH(CH₃)— |
| A-217. | CH₃ | (R) (1,1,4,4,7-pentamethyl-1,2,3,4-tetrahydronaphthalin-6-yl)-CH(CH₃)— |
| A-218. | CH₃ | (S) (1,1,4,4,7-pentamethyl-1,2,3,4-tetrahydronaphthalin-6-yl)-CH(CH₃)— |
| A-219. | CH₃ | (±) (1,1,7-trimethyl-1,2,3,4-tetrahydronaphthalin-6-yl)-CH(CH₃)— |
| A-220. | CH₃ | (R) (1,1,7-trimethyl-1,2,3,4-tetrahydronaphthalin-6-yl)-CH(CH₃)— |
| A-221. | CH₃ | (S) (1,1,7-trimethyl-1,2,3,4-tetrahydronaphthalin-6-yl)-CH(CH₃)— |
| A-222. | CH₃ | (±) (2-methyl-1,3-dioxan-2-yl)-CH(CH₃)— |
| A-223. | CH₃ | (R) 2-methyl-1,3-dioxan-2-yl)-CH(CH₃)— |
| A-224. | CH₃ | (S) 2-methyl-1,3-dioxan-2-yl)-CH(CH₃)— |
| A-225. | CH₃ | (±) (2,5,5-trimethyl-1,3-dioxan-2-yl)-CH(CH₃)— |
| A-226. | CH₃ | (R) 2,5,5-trimethyl-1,3-dioxan-2-yl)-CH(CH₃)— |
| A-227. | CH₃ | (S) 2,5,5-trimethyl-1,3-dioxan-2-yl)-CH(CH₃)— |
| A-228. | CH₃ | (±) (2,2-difluorobenzodioxole-5-yl)CH(C₂H₅)— |
| A-229. | CH₃ | (R) (2,2-difluorobenzodioxole-5-yl)CH(C₂H₅)— |
| A-230. | CH₃ | (S) (2,2-difluorobenzodioxole-5-yl)CH(C₂H₅)— |
| A-231. | CH₃ | C₆H₅CH₂CH₂— |
| A-232. | CH₃ | 4-F—C₆H₄CH₂CH₂— |
| A-233. | CH₃ | 4-Cl—C₆H₄CH₂CH₂— |
| A-234. | CH₃ | 4-Br—C₆H₄CH₂CH₂— |
| A-235. | CH₃ | 4-CH₃O—C₆H₄CH₂CH₂— |
| A-236. | CH₃ | 4-C₂H₅O—C₆H₄CH₂CH₂— |
| A-237. | CH₃ | 4-n-C₃H₇O—C₆H₄CH₂CH₂— |
| A-238. | CH₃ | 4-n-C₄H₉O—C₆H₄CH₂CH₂— |
| A-239. | CH₃ | 4-t-C₄H₉O—C₆H₄CH₂CH₂— |
| A-240. | CH₃ | 3,4-(CH₃O)₂—C₆H₄CH₂CH₂— |

TABLE A-continued

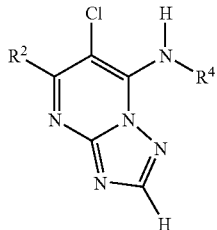

(Ia)

| No. | $R^2$ | $R^4$ |
|---|---|---|
| A-241. | $CH_3$ | 4-$H_3C$—$C_6H_4CH_2CH_2$— |
| A-242. | $CH_3$ | 4-$H_3C$—$H_2C$—$C_6H_4CH_2CH_2$— |
| A-243. | $CH_3$ | 4-$H_3C$—$H_2C$—$H_2C$—$C_6H_4CH_2CH_2$— |
| A-244. | $CH_3$ | 4-$H_3C$—$H_2C$—$H_2C$—$H_2C$—$C_6H_4CH_2CH_2$— |
| A-245. | $CH_3$ | 4-$(CH_3)_3C$—$C_6H_4CH_2CH_2$— |
| A-246. | $CH_3$ | 4-$F_3CO$—$C_6H_4CH_2CH_2$— |
| A-247. | $CH_3$ | 4-$F_3C$—$C_6H_4CH_2CH_2$— |
| A-248. | $CH_3$ | 3-$F_3C$—$C_6H_4CH_2CH_2$— |
| A-249. | $CH_3CH_2$ | 4-$CH_3$-cyclohexyl- |
| A-250. | $CH_3CH_2$ | cis-4-$CH_3$-cyclohexyl- |
| A-251. | $CH_3CH_2$ | trans-4-$CH_3$-cyclohexyl- |
| A-252. | $CH_3CH_2$ | 4-$C_2H_5$-cyclohexyl- |
| A-253. | $CH_3CH_2$ | cis-4-$C_2H_5$-cyclohexyl- |
| A-254. | $CH_3CH_2$ | trans-4-$C_2H_5$-cyclohexyl- |
| A-255. | $CH_3CH_2$ | 4-n-propyl-cyclohexyl- |
| A-256. | $CH_3CH_2$ | cis-4-n-propyl-cyclohexyl- |
| A-257. | $CH_3CH_2$ | trans-4-n-propyl-cyclohexyl- |
| A-258. | $CH_3CH_2$ | 4-isopropyl-cyolohexyl- |
| A-259. | $CH_3CH_2$ | cis-4-isopropyl-cyclohexyl- |
| A-260. | $CH_3CH_2$ | trans-4-isopropyl-cyclohexyl- |
| A-261. | $CH_3CH_2$ | 4-n-butylcyclohexyl- |
| A-262. | $CH_3CH_2$ | cis-4-n-butylcyclohexyl- |
| A-263. | $CH_3CH_2$ | trans-4-n-butylcyclohexyl- |
| A-264. | $CH_3CH_2$ | 4-(2-butyl)cyclohexyl- |
| A-265. | $CH_3CH_2$ | cis-4-(2-butyl)cyclohexyl- |
| A-266. | $CH_3CH_2$ | trans-4-(2-butyl)cyclohexyl- |
| A-267. | $CH_3CH_2$ | 4-tert-butylcyclohexyl- |
| A-268. | $CH_3CH_2$ | cis-4-tert-butylcyclohexyl- |
| A-269. | $CH_3CH_2$ | trans-4-tert-butylcyclohexyl- |
| A-270. | $CH_3CH_2$ | 4-(cyolohexyl-$C(CH_3)_2$)-cyclohexyl- |
| A-271. | $CH_3CH_2$ | cis-4-(cyclohexyl-$C(CH_3)_2$)-cyclohexyl- |
| A-272. | $CH_3CH_2$ | trans-4-(cyclohexyl-$C(CH_3)_2$)-cyclohexyl- |
| A-273. | $CH_3CH_2$ | $C_6H_5$— |
| A-274. | $CH_3CH_2$ | 4-F—$C_6H_4$— |
| A-275. | $CH_3CH_2$ | 4-Cl—$C_6H_4$— |
| A-276. | $CH_3CH_2$ | 4-Br—$C_6H_4$— |
| A-277. | $CH_3CH_2$ | 4-$(C_6H_5)$—$C_6H_4$— |
| A-278. | $CH_3CH_2$ | 4-phenoxyphenyl |
| A-279. | $CH_3CH_2$ | benzyl |
| A280. | $CH_3CH_2$ | 4-$CH_3$—$C_6H_4$—$CH_2$— |
| A281. | $CH_3CH_2$ | 4-$C_2H_5$—$C_6H_4$—$CH_2$— |
| A282. | $CH_3CH_2$ | 4-n-$C_3H_7$—$C_6H_4$—$CH_2$— |
| A283. | $CH_3CH_2$ | 4-isopropyl-$C_6H_4$—$CH_2$— |
| A-284. | $CH_3CH_2$ | 4-n-$C_4H_9$—$C_6H_4$—$CH_2$— |
| A-285. | $CH_3CH_2$ | 4-isobutyl-$C_6H_4$—$CH_2$— |
| A-286. | $CH_3CH_2$ | 4-tert-buyl-$C_6H_4CH_2$— |
| A-287. | $CH_3CH_2$ | 4-$F_3C$—$C_6H_4CH_2$— |
| A-288. | $CH_3CH_2$ | 4-methoxy-$C_6H_4CH_2$— |
| A-289. | $CH_3CH_2$ | 4-ethoxy-$C_6H_4CH_2$— |
| A-290. | $CH_3CH_2$ | 4-n-propoxy-$C_6H_4CH_2$— |
| A-291. | $CH_3CH_2$ | 4-isopropoxy-$C_6H_4CH_2$— |
| A-292. | $CH_3CH_2$ | 4-n-butoxy-$C_6H_4CH_2$— |
| A-293. | $CH_3CH_2$ | 4-tert-butoxy-$C_6H_4CH_2$— |
| A-294. | $CH_3CH_2$ | 4-F—$C_6H_4CH_2$— |
| A-295. | $CH_3CH_2$ | 4-Cl—$C_6H_4CH_2$— |
| A-296. | $CH_3CH_2$ | 4-Br—$C_6H_4CH_2$— |
| A-297. | $CH_3CH_2$ | 3,4-$F_2$—$C_6H_3CH_2$— |
| A-298. | $CH_3CH_2$ | 3,4-$Cl_2$—$C_6H_3CH_2$— |
| A-299. | $CH_3CH_2$ | 3,4-$Br_2$—$C_6H_3CH_2$— |
| A-300. | $CH_3CH_2$ | 4-(4-$CH_3$—$C_6H_4$—O)—$C_6H_4$—$CH_2$— |
| A-301. | $CH_3CH_2$ | 4-(4-$C_2H_5$—$C_6H_4$—O)—$C_6H_4$—$CH_2$— |
| A-302. | $CH_3CH_2$ | 4-(4-n-$C_3H_7$—$C_6H_4$—O)—$C_6H_4$—$CH_2$— |
| A-303. | $CH_3CH_2$ | 4-(4-iso-$C_3H_7$—$C_6H_4$—O)—$C_6H_4$—$CH_2$— |
| A-304. | $CH_3CH_2$ | 4-(4-n-$C_4H_9$—$C_6H_4$—O)—$C_6H_4$—$CH_2$— |
| A-305. | $CH_3CH_2$ | 4-(4-iso-$C_4H_9$—$C_6H_4$—O)—$C_6H_4$—$CH_2$— |

TABLE A-continued

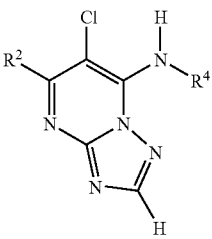

(Ia)

| No. | R² | R⁴ |
|---|---|---|
| A-306. | CH₃CH₂ | 4-(4-tert-C₄H₉—C₆H₄—O)—C₆H₄—CH₂— |
| A-307. | CH₃CH₂ | 4-(4-H₃C—O—C₆H₄—O)—C₆H₄—CH₂— |
| A-308. | CH₃CH₂ | 4-(4-H₃C—H₂C—O—C₆H₄—O)—C₆H₄—CH₂— |
| A-309. | CH₃CH₂ | 4-(4-H₃C—H₂C—H₂C—O—C₆H₄—O)—C₆H₄—CH₂— |
| A-310. | CH₃CH₂ | 4-(4-H₃C—H₂C—H₂C—H₂C—O—C₆H₄—O)—C₆H₄—CH₂— |
| A-311. | CH₃CH₂ | 4-(4-tert-butoxy-C₆H₄—O)—C₆H₄—CH₂— |
| A-312. | CH₃CH₂ | 4-(4-Cl—C₆H₄—O)—C₆H₄—CH₂— |
| A-313. | CH₃CH₂ | 4-(4-Br—C₆H₄—O)—C₆H₄—CH₂— |
| A-314. | CH₃CH₂ | 4-(3-CH₃—C₆H₄—O)—C₆H₄—CH₂— |
| A-315. | CH₃CH₂ | 4-(3-C₂H₅—C₆H₄—O)—C₆H₄—CH₂— |
| A-316. | CH₃CH₂ | 4-(3-n-C₃H₇—C₆H₄—O)—C₆H₄—CH₂— |
| A-317. | CH₃CH₂ | 4-(3-iso-C₃H₇—C₆H₄—O)—C₆H₄—CH₂— |
| A-318. | CH₃CH₂ | 4-(3-n-C₄H₉—C₆H₄—O)—C₆H₄—CH₂— |
| A-319. | CH₃CH₂ | 4-(3-iso-C₄H₉—C₆H₄—O)—C₆H₄—CH₂— |
| A-320. | CH₃CH₂ | 4-(3-tert-butyl-C₆H₄—O)—C₆H₄—CH₂— |
| A-321. | CH₃CH₂ | 4-(3-H₃C—O—C₆H₄—O)—C₆H₄—CH₂— |
| A-322. | CH₃CH₂ | 4-(3-H₃C—H₂C—O—C₆H₄—O)—C₆H₄—CH₂— |
| A-323. | CH₃CH₂ | 4-(3-H₃C—H₂C—H₂C—O—C₆H₄—O)—C₆H₄—CH₂— |
| A-324. | CH₃CH₂ | 4-(3-H₃C—H₂C—H₂C—H₂C—O—C₆H₄—O)—C₆H₄—CH₂— |
| A-325. | CH₃CH₂ | 4-(3-tert-butoxy-C₆H₄—O)—C₆H₄—CH₂— |
| A-326. | CH₃CH₂ | 4-(3-F—C₆H₄—O)—C₆H₄—CH₂— |
| A-327. | CH₃CH₂ | 4-(3-Cl—C₆H₄—O)—C₆H₄—CH₂— |
| A-328. | CH₃CH₂ | 4-(3-Br—C₆H₄—O)—C₆H₄—CH₂— |
| A-329. | CH₃CH₂ | 4-(2-CH₃—C₆H₄—O)—C₆H₄—CH₂— |
| A-330. | CH₃CH₂ | 4-(2-C₂H₅—C₆H₄—O)—C₆H₄—CH₂— |
| A-331. | CH₃CH₂ | 4-(2-n-C₃H₇—C₆H₄—O)—C₆H₄—CH₂— |
| A-332. | CH₃CH₂ | 4-(2-iso-C₃H₇—C₆H₄—O)—C₆H₄—CH₂— |
| A-333. | CH₃CH₂ | 4-(2-n-C₄H₉—C₆H₄—O)—C₆H₄—CH₂— |
| A-334. | CH₃CH₂ | 4-(2-iso-C₄H₉—C₆H₄—O)—C₆H₄—CH₂— |
| A-335. | CH₃CH₂ | 4-(2-tert-butyl-C₆H₄—O)—C₆H₄—CH₂— |
| A-336. | CH₃CH₂ | 4-(2-H₃C—O—C₆H₄—O)—C₆H₄—CH₂— |
| A-337. | CH₃CH₂ | 4-(2-H₃C—H₂C—O—C₆H₄—O)—C₆H₄—CH₂— |
| A-338. | CH₃CH₂ | 4-(2-H₃C—H₂C—H₂C—O—C₆H₄—O)—C₆H₄—CH₂— |
| A-339. | CH₃CH₂ | 4-(2-H₃C—H₂C—H₂C—H₂C—O—C₆H₄—O)—C₆H₄—CH₂— |
| A-340. | CH₃CH₂ | 4-(2-tert-butoxy-C₆H₄—O)—C₆H₄—CH₂— |
| A-341. | CH₃CH₂ | 4-(2-F—C₆H₄—O)—C₆H₄—CH₂— |
| A-342. | CH₃CH₂ | 4-(2-Cl—C₆H₄—O)—C₆H₄—CH₂— |
| A-343. | CH₃CH₂ | 4-(2-Br—C₆H₄—O)—C₆H₄—CH₂— |
| A-344. | CH₃CH₂ | 4-(3,4-F₂—C₆H₃—O)—C₆H₄—CH₂— |
| A-345. | CH₃CH₂ | 4-(3,4-Cl₂—C₆H₃—O)—C₆H₄—CH₂— |
| A-346. | CH₃CH₂ | 4-(3,4-(CH₃)₂—C₆H₃—O)—C₆H₄—CH₂— |
| A-347. | CH₃CH₂ | 4-(3-F-4-Cl—C₆H₃—O)—C₆H₄—CH₂— |
| A-348. | CH₃CH₂ | 4-(3-Cl-4-F—C₆H₃—O)—C₆H₄—CH₂— |
| A-349. | CH₃CH₂ | 4-(3-CH₃-4-Cl—C₆H₃—O)—C₆H₄—CH₂— |
| A-350. | CH₃CH₂ | 4-(3-Cl-4-CH₃—C₆H₃—O)—C₆H₄—CH₂— |
| A-351. | CH₃CH₂ | 4-(3-Cl-4-Br—C₆H₃—O)—C₆H₄—CH₂— |
| A-352. | CH₃CH₂ | 4-(3-CH₃-4-Br—C₆H₃—O)—C₆H₄—CH₂— |
| A-353. | CH₃CH₂ | (±) phenyl-CH(CH₃)— |
| A-354. | CH₃CH₂ | (R) phenyl-CH(CH₃)— |
| A-355. | CH₃CH₂ | (S) phenyl-CH(CH₃)— |
| A-356. | CH₃CH₂ | (±) 4-F-phenyl-CH(CH₃)— |
| A-357. | CH₃CH₂ | (R) 4-F-phenyl-CH(CH₃)— |
| A-358. | CH₃CH₂ | (S) 4-F-phenyl-CH(CH₃)— |
| A-359. | CH₃CH₂ | (±) 4-Cl-phenyl-CH(CH₃)— |
| A-360. | CH₃CH₂ | (R) 4-Cl-phenyl-CH(CH₃)— |
| A-361. | CH₃CH₂ | (S) 4-Cl-phenyl-CH(CH₃)— |
| A-362. | CH₃CH₂ | (±) 4-Br-phenyl-CH(CH₃)— |
| A-363. | CH₃CH₂ | (R) 4-Br-phenyl-CH(CH₃)— |
| A-364. | CH₃CH₂ | (S) 4-Br-phenyl-CH(CH₃)— |
| A-365. | CH₃CH₂ | (±) 4-Cl-2-F-phenyl-CH(CH₃)— |
| A-366. | CH₃CH₂ | (R) 4-Cl-2-F-phenyl-CH(CH₃)— |
| A-367. | CH₃CH₂ | (S) 4-Cl-2-F-phenyl-CH(CH₃)— |
| A-368. | CH₃CH₂ | (±) 6-Cl-2-F-phenyl-CH(CH₃)— |
| A-369. | CH₃CH₂ | (R) 6-Cl-2-F-phenyl-CH(CH₃)— |
| A-370. | CH₃CH₂ | (S) 6-Cl-2-F-phenyl-CH(CH₃)— |

TABLE A-continued

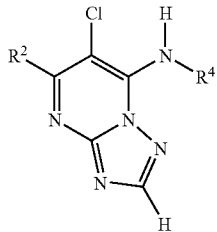
(Ia)

| No. | $R^2$ | $R^4$ |
|---|---|---|
| A-371. | $CH_3CH_2$ | (±) 2-F-phenyl-CH(CH$_3$)— |
| A-372. | $CH_3CH_2$ | (R) 2-F-phenyl-CH(CH$_3$)— |
| A-373. | $CH_3CH_2$ | (S) 2-F-phenyl-CH(CH$_3$)— |
| A-374. | $CH_3CH_2$ | (S) 2,4-F$_2$-phenyl-CH(CH$_3$)— |
| A-375. | $CH_3CH_2$ | (±) 2,4-F$_2$-phenyl-CH(CH$_3$)— |
| A-376. | $CH_3CH_2$ | (R) 2,4-F$_2$-phenyl-CH(CH$_3$)— |
| A-377. | $CH_3CH_2$ | (S) 2,5-F$_2$-phenyl-CH(CH$_3$)— |
| A-378. | $CH_3CH_2$ | (±) 2,5-F$_2$-phenyl-CH(CH$_3$)— |
| A-379. | $CH_3CH_2$ | (R) 2,5-F$_2$-phenyl-CH(CH$_3$)— |
| A-380. | $CH_3CH_2$ | (S) 2,6-F$_2$-phenyl-CH(CH$_3$)— |
| A-381. | $CH_3CH_2$ | (±) 2,6-F$_2$-phenyl-CH(CH$_3$)— |
| A-382. | $CH_3CH_2$ | (R) 2,6-F$_2$-phenyl-CH(CH$_3$)— |
| A-383. | $CH_3CH_2$ | (±) 2-CH$_3$O-phenyl-CH(CH$_3$)— |
| A-384. | $CH_3CH_2$ | (R) 2-CH$_3$O-phenyl-CH(CH$_3$)— |
| A-385. | $CH_3CH_2$ | (S) 2-CH$_3$O-phenyl-CH(CH$_3$)— |
| A-386. | $CH_3CH_2$ | (±) 4-CH$_3$O-phenyl-CH(CH$_3$)— |
| A-387. | $CH_3CH_2$ | (R) 4-CH$_3$O-phenyl-CH(CH$_3$)— |
| A-388. | $CH_3CH_2$ | (S) 4-CH$_3$O-phenyl-CH(CH$_3$)— |
| A-389. | $CH_3CH_2$ | (±) 4-H$_5$C$_2$—O-phenyl-CH(CH$_3$)— |
| A-390. | $CH_3CH_2$ | (R) 4-H$_5$C$_2$—O-phenyl-CH(CH$_3$)— |
| A-391. | $CH_3CH_2$ | (S) 4-H$_5$C$_2$—O-phenyl-CH(CH$_3$)— |
| A-392. | $CH_3CH_2$ | (±) 4-n-propoxy-phenyl-CH(CH$_3$)— |
| A-393. | $CH_3CH_2$ | (R) 4-n-propoxy-phenyl-CH(CH$_3$)— |
| A-394. | $CH_3CH_2$ | (S) 4-n-propoxy-phenyl-CH(CH$_3$)— |
| A-395. | $CH_3CH_2$ | (±) 4-n-butoxy-phenyl-CH(CH$_3$)— |
| A-396. | $CH_3CH_2$ | (R) 4-n-butoxyx-phenyl-CH(CH$_3$)— |
| A-397. | $CH_3CH_2$ | (S) 4-n-butoxyphenyl-CH(CH$_3$)— |
| A-398. | $CH_3CH_2$ | (±) 4-tert-butoxy-phenyl-CH(CH$_3$)— |
| A-399. | $CH_3CH_2$ | (R) 4-tert-butoxyx-phenyl-CH(CH$_3$)— |
| A-400. | $CH_3CH_2$ | (S) 4-tert-butoxyphenyl-CH(CH$_3$)— |
| A-401. | $CH_3CH_2$ | (±) 4-CH$_3$-phenyl-CH(CH$_3$)— |
| A-402. | $CH_3CH_2$ | (R) 4-CH$_3$-phenyl-CH(CH$_3$)— |
| A-403. | $CH_3CH_2$ | (S) 4-CH$_3$-phenyl-CH(CH$_3$)— |
| A-404. | $CH_3CH_2$ | (±) 4-C$_2$H$_5$-phenyl-CH(CH$_3$)— |
| A-405. | $CH_3CH_2$ | (R) 4-C$_2$H$_5$-phenyl-CH(CH$_3$)— |
| A-406. | $CH_3CH_2$ | (S) 4-C$_2$H$_5$-phenyl-CH(CH$_3$)— |
| A-407. | $CH_3CH_2$ | (±) 4-n-C$_3$H$_7$-phenyl-CH(CH$_3$)— |
| A-408. | $CH_3CH_2$ | (R) 4-n-C$_3$H$_7$-phenyl-CH(CH$_3$)— |
| A-409. | $CH_3CH_2$ | (S) 4-n-C$_3$H$_7$-phenyl-CH(CH$_3$)— |
| A-410. | $CH_3CH_2$ | (±) 4-iso-C$_3$H$_7$-phenyl-CH(CH$_3$)— |
| A-411. | $CH_3CH_2$ | (R) 4-iso-C$_3$H$_7$-phenyl-CH(CH$_3$)— |
| A-412. | $CH_3CH_2$ | (S) 4-iso-C$_3$H$_7$-phenyl-CH(CH$_3$)— |
| A-413. | $CH_3CH_2$ | (±) 4-n-C$_4$H$_9$-phenyl-CH(CH$_3$)— |
| A-414. | $CH_3CH_2$ | (R) 4-n-C$_4$H$_9$-phenyl-CH(CH$_3$)— |
| A-415. | $CH_3CH_2$ | (S) 4-n-C$_4$H$_9$-phenyl-CH(CH$_3$)— |
| A-416. | $CH_3CH_2$ | (±) 4-tert-C$_4$H$_9$-phenyl-CH(CH$_3$)— |
| A-417. | $CH_3CH_2$ | (R) 4-tert-C$_4$H$_9$-phenyl-CH(CH$_3$)— |
| A-418. | $CH_3CH_2$ | (S) 4-tert-C$_4$H$_9$-phenyl-CH(CH$_3$)— |
| A-419. | $CH_3CH_2$ | (±) 4-cycl.-C$_6$H$_{11}$-phenyl-CH(CH$_3$)— |
| A-420. | $CH_3CH_2$ | (R) 4-cycl.-C$_6$H$_{11}$-phenyl-CH(CH$_3$)— |
| A-421. | $CH_3CH_2$ | (S) 4-cycl.-C$_6$H$_{11}$-phenyl-CH(CH$_3$)— |
| A-422. | $CH_3CH_2$ | (±) 4-OCF$_3$-phenyl-CH(CH$_3$)— |
| A-423. | $CH_3CH_2$ | (R) 4-OCF$_3$-phenyl-CH(CH$_3$)— |
| A-424. | $CH_3CH_2$ | (S) 4-OCF$_3$-phenyl-CH(CH$_3$)— |
| A-425. | $CH_3CH_2$ | (±) 4-CF$_3$-phenyl-CH(CH$_3$)— |
| A-426. | $CH_3CH_2$ | (R) 4-CF$_3$-phenyl-CH(CH$_3$)— |
| A-427. | $CH_3CH_2$ | (S) 4-CF$_3$-phenyl-CH(CH$_3$)— |
| A-428. | $CH_3CH_2$ | (±) 3-F-phenyl-CH(CH$_3$)— |
| A-429. | $CH_3CH_2$ | (R) 3-F-phenyl-CH(CH$_3$)— |
| A-430. | $CH_3CH_2$ | (S) 3-F-phenyl-CH(CH$_3$)— |
| A-431. | $CH_3CH_2$ | (±) 3-Cl-phenyl-CH(CH$_3$)— |
| A-432. | $CH_3CH_2$ | (R) 3-Cl-phenyl-CH(CH$_3$)— |
| A-433. | $CH_3CH_2$ | (S) 3-Cl-phenyl-CH(CH$_3$)— |
| A-434. | $CH_3CH_2$ | (±) 3-Br-phenyl-CH(CH$_3$)— |
| A-435. | $CH_3CH_2$ | (R) 3-Br-phenyl-CH(CH$_3$)— |

TABLE A-continued

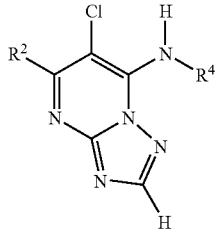

(Ia)

| No. | R² | R⁴ |
|---|---|---|
| A-436. | $CH_3CH_2$ | (S) 3-Br-phenyl-CH(CH₃)— |
| A-437. | $CH_3CH_2$ | (±) 3-CF₃-phenyl-CH(CH₃)— |
| A-438. | $CH_3CH_2$ | (R) 3-CF₃-phenyl-CH(CH₃)— |
| A-439. | $CH_3CH_2$ | (S) 3-CF₃-phenyl-CH(CH₃)— |
| A-440. | $CH_3CH_2$ | (±) 3,4-F₂-phenyl-CH(CH₃)— |
| A-441. | $CH_3CH_2$ | (R) 3,4-F₂-phenyl-CH(CH₃)— |
| A-442. | $CH_3CH_2$ | (S) 3,4-F₂-phenyl-CH(CH₃)— |
| A-443. | $CH_3CH_2$ | (±) 3,4-Cl₂-phenyl-CH(CH₃)— |
| A-444. | $CH_3CH_2$ | (R) 3,4-Cl₂-phenyl-CH(CH₃)— |
| A-445. | $CH_3CH_2$ | (S) 3,4-Cl₂-phenyl-CH(CH₃)— |
| A-446. | $CH_3CH_2$ | (±) 3,4-Br₂-phenyl-CH(CH₃)— |
| A-447. | $CH_3CH_2$ | (R) 3,4-Br₂-phenyl-CH(CH₃)— |
| A-448. | $CH_3CH_2$ | (S) 3,4-Br₂-phenyl-CH(CH₃)— |
| A-449. | $CH_3CH_2$ | (±) 4-Difluoromethoxyphenyl-CH(CH₃)— |
| A-450. | $CH_3CH_2$ | (R) 4-Difluoromethoxyphenyl-CH(CH₃)— |
| A-451. | $CH_3CH_2$ | (S) 4-Difluoromethoxyphenyl-CH(CH₃)— |
| A-452. | $CH_3CH_2$ | (±) 4-(1,1,2,2-tetrafluoroethoxy)phenyl-CH(CH₃)— |
| A-453. | $CH_3CH_2$ | (R) 4-(1,1,2,2-tetrafluoroethoxy)phenyl-CH(CH₃)— |
| A-454. | $CH_3CH_2$ | (S) 4-(1,1,2,2-tetrafluoroethoxy)phenyl-CH(CH₃)— |
| A-455. | $CH_3CH_2$ | (±) (5,5,7,7-tetramethylindan-2-yl)-CH(CH₃)— |
| A-456. | $CH_3CH_2$ | (R) (5,5,7,7-tetramethylindan-2-yl)-CH(CH₃)— |
| A-457. | $CH_3CH_2$ | (S) (5,5,7,7-tetramethylindan-2-yl)-CH(CH₃)— |
| A-458. | $CH_3CH_2$ | (±) (1,1,4,4,-tetramethyl-1,2,3,4-tetrahydronaphthalin-6-yl)-CH(CH₃)— |
| A-459. | $CH_3CH_2$ | (R) (1,1,4,4,-tetramethyl-1,2,3,4-tetrahydronaphthalin-6-yl)-CH(CH₃)— |
| A-460. | $CH_3CH_2$ | (S) (1,1,4,4,-tetramethyl-1,2,3,4-tetrahydronaphthalin-6-yl)-CH(CH₃)— |
| A-461. | $CH_3CH_2$ | (±) (1,1-dimethyl-1,2,3,4-tetrahydronaphthalin-6-yl)-CH(CH₃)— |
| A-462. | $CH_3CH_2$ | (R) (1,1-dimethyl-1,2,3,4-tetrahydronaphthalin-6-yl)-CH(CH₃)— |
| A-463. | $CH_3CH_2$ | (S) (1,1-dimethyl-1,2,3,4-tetrahydronaphthalin-6-yl)-CH(CH₃)— |
| A-464. | $CH_3CH_2$ | (±) (1,1,4,4,7-pentamethyl-1,2,3,4-tetrahydronaphthalin-6-yl)-CH(CH₃)— |
| A-465. | $CH_3CH_2$ | (R) (1,1,4,4,7-pentamethyl-1,2,3,4-tetrahydronaphthalin-6-yl)-CH(CH₃)— |
| A-466. | $CH_3CH_2$ | (S) (1,1,4,4,7-pentamethyl-1,2,3,4-tetrahydronaphthalin-6-yl)-CH(CH₃)— |
| A-467. | $CH_3CH_2$ | (±) (1,1,7-trimethyl-1,2,3,4-tetrahydronaphthalin-6-yl)-CH(CH₃)— |
| A-468. | $CH_3CH_2$ | (R) (1,1,7-trimethyl-1,2,3,4-tetrahydronaphthalin-6-yl)-CH(CH₃)— |
| A-469. | $CH_3CH_2$ | (S) (1,1,7-trimethyl-1,2,3,4-tetrahydronaphthalin-6-yl)-CH(CH₃)— |
| A-470. | $CH_3CH_2$ | (±) (2-methyl-1,3-dioxan-2-yl)-CH(CH₃)— |
| A-471. | $CH_3CH_2$ | (R) 2-methyl-1,3-dioxan-2-yl)-CH(CH₃)— |
| A-472. | $CH_3CH_2$ | (S) 2-methyl-1,3-dioxan-2-yl)-CH(CH₃)— |
| A-473. | $CH_3CH_2$ | (±) (2,5,5-trimethyl-1,3-dioxan-2-yl)-CH(CH₃)— |
| A-474. | $CH_3CH_2$ | (R) 2,5,5-trimethyl-1,3-dioxan-2-yl)-CH(CH₃)— |
| A-475. | $CH_3CH_2$ | (S) 2,5,5-trimethyl-1,3-dioxan-2-yl)-CH(CH₃)— |
| A-476. | $CH_3CH_2$ | (±) (2,2-difluorobenzodioxole-5-yl)CH(C₂H₅)— |
| A-477. | $CH_3CH_2$ | (R) (2,2-difluorobenzodioxole-5-yl)CH(C₂H₅)— |
| A-478. | $CH_3CH_2$ | (S) (2,2-difluorobenzodioxole-5-yl)CH(C₂H₅)— |
| A-479. | $CH_3CH_2$ | $C_6H_5CH_2CH_2$— |
| A-480. | $CH_3CH_2$ | 4-F—$C_6H_4CH_2CH_2$— |
| A-481. | $CH_3CH_2$ | 4-Cl—$C_6H_4CH_2CH_2$— |
| A-482. | $CH_3CH_2$ | 4-Br—$C_6H_4CH_2CH_2$— |
| A-483. | $CH_3CH_2$ | 4-$CH_3O$—$C_6H_4CH_2CH_2$— |
| A-484. | $CH_3CH_2$ | 4-$C_2H_5O$—$C_6H_4CH_2CH_2$— |
| A-485. | $CH_3CH_2$ | 4-n-$C_3H_7O$—$C_6H_4CH_2CH_2$— |
| A-486. | $CH_3CH_2$ | 4-n-$C_4H_9O$—$C_6H_4CH_2CH_2$— |
| A-487. | $CH_3CH_2$ | 4-t-$C_4H_9O$—$C_6H_4CH_2CH_2$— |
| A-488. | $CH_3CH_2$ | 3,4-$(CH_3O)_2$—$C_6H_4CH_2CH_2$— |

TABLE A-continued

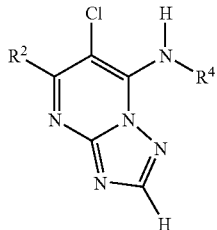
(Ia)

| No. | $R^2$ | $R^4$ |
| --- | --- | --- |
| A-489. | $CH_3CH_2$ | 4-$H_3C$—$C_6H_4CH_2CH_2$— |
| A-490. | $CH_3CH_2$ | 4-$H_3C$—$H_2C$—$C_6H_4CH_2CH_2$— |
| A-491. | $CH_3CH_2$ | 4-$H_3C$—$H_2C$—$H_2C$—$C_6H_4CH_2CH_2$— |
| A-492. | $CH_3CH_2$ | 4-$H_3C$—$H_2C$—$H_2C$—$H_2C$—$C_6H_4CH_2CH_2$— |
| A-493. | $CH_3CH_2$ | 4-$(CH_3)_3C$—$C_6H_4CH_2CH_2$— |
| A-494. | $CH_3CH_2$ | 4-$F_3CO$—$C_6H_4CH_2CH_2$— |
| A-495. | $CH_3CH_2$ | 4-$F_3C$—$C_6H_4CH_2CH_2$— |
| A-496. | $CH_3CH_2$ | 3-$F_3C$—$C_6H_4CH_2CH_2$— |
| A-497. | $CH_3CHF$ | 4-$CH_3$-cyclohexyl- |
| A-498. | $CH_3CHF$ | cis-4-$CH_3$-cyclohexyl- |
| A-499. | $CH_3CHF$ | trans-4-$CH_3$-cyclohexyl- |
| A-500. | $CH_3CHF$ | 4-$C_2H_5$-cyclohexyl- |
| A-501. | $CH_3CHF$ | cis-4-$C_2H_5$-cyclohexyl- |
| A-502. | $CH_3CHF$ | trans-4-$C_2H_5$-cyolohexyl- |
| A-503. | $CH_3CHF$ | 4-n-propyl-cyclohexyl- |
| A-504. | $CH_3CHF$ | cis-4-n-propyl-cyclohexyl- |
| A-505. | $CH_3CHF$ | trans-4-n-propyl-cyclohexyl- |
| A-506. | $CH_3CHF$ | 4-isopropyl-cyclohexyl- |
| A-507. | $CH_3CHF$ | cis-4-isopropyl-cyclohexyl- |
| A-508. | $CH_3CHF$ | trans-4-isopropyl-cyclohexyl- |
| A-509. | $CH_aCHF$ | 4-n-butylcyolohexyl- |
| A-510. | $CH_3CHF$ | cis-4-n-butylcyclohexyl- |
| A-511. | $CH_3CHF$ | trans-4-n-butylcyclohexyl- |
| A-512. | $CH_3CHF$ | 4-tert-butylcyclohexyl- |
| A-513. | $CH_3CHF$ | cis-4-tert-butylcyclohexyl- |
| A-514. | $CH_3CHF$ | trans-4-tert-butylcyclohexyl- |
| A-515. | $CH_3CHF$ | 4-(2-butyl)cyclohexyl- |
| A-516. | $CH_3CHF$ | cis-4-(2-butyl)cyclohexyl- |
| A-517. | $CH_3CHF$ | trans-4-(2-butyl)cyclohexyl- |
| A-518. | $CH_3CHF$ | 4-(cyclohexyl-$C(CH_3)_2$)-cyclohexyl- |
| A-519. | $CH_3CHF$ | cis-4-(cyclohexyl-$C(CH_3)_2$)-cyclohexyl- |
| A-520. | $CH_3CHF$ | trans-4-(cyclohexyl-$C(CH_3)_2$)-cyclohexyl- |
| A-521. | $CH_3CHF$ | $C_6H_5$— |
| A-522. | $CH_3CHF$ | 4-F—$C_6H_4$— |
| A-523. | $CH_3CHF$ | 4-Cl—$C_6H_4$— |
| A-524. | $CH_3CHF$ | 4-Br—$C_6H_4$— |
| A-525. | $CH_3CHF$ | 4-$(C_6H_5)$—$C_6H_4$— |
| A-526. | $CH_3CHF$ | 4-phenoxyphenyl |
| A-527. | $CH_3CHF$ | benzyl |
| A-528. | $CH_3CHF$ | 4-$CH_3$—$C_6H_4$—$CH_2$— |
| A-529. | $CH_3CHF$ | 4-$C_2H_5$—$C_6H_4$—$CH_2$— |
| A-530. | $CH_3CHF$ | 4-n-$C_3H_7$—$C_6H_4$—$CH_2$— |
| A-531. | $CH_3CHF$ | 4-isopropyl-$C_6H_4$—$CH_2$— |
| A-532. | $CH_3CHF$ | 4-n-$C_4H_9$—$C_6H_4$—$CH_2$— |
| A-533. | $CH_3CHF$ | 4-isobutyl-$C_6H_4$—$CH_2$— |
| A-534. | $CH_3CHF$ | 4-tert-buyl-$C_6H_4CH_2$— |
| A-535. | $CH_3CHF$ | 4-$F_3C$—$C_6H_4CH_2$— |
| A-536. | $CH_3CHF$ | 4-methoxy-$C_6H_4CH_2$— |
| A-537. | $CH_3CHF$ | 4-ethoxy-$C_6H_4CH_2$— |
| A-538. | $CH_3CHF$ | 4-n-propoxy-$C_6H_4CH_2$— |
| A-539. | $CH_3CHF$ | 4-isopropoxy-$C_6H_4CH_2$— |
| A-540. | $CH_3CHF$ | 4-n-butoxy-$C_6H_4CH_2$— |
| A-541. | $CH_3CHF$ | 4-tert-butoxy-$C_6H_4CH_2$— |
| A-542. | $CH_3CHF$ | 4-F—$C_6H_4CH_2$— |
| A-543. | $CH_3CHF$ | 4-Cl—$C_6H_4CH_2$— |
| A-544. | $CH_3CHF$ | 4-Br—$C_6H_4CH_2$— |
| A-545. | $CH_3CHF$ | 3,4-$F_2$—$C_6H_3CH_2$— |
| A-546. | $CH_3CHF$ | 3,4-$Cl_2$—$C_6H_3CH_2$— |
| A-547. | $CH_3CHF$ | 3,4-$Br_2$—$C_6H_3CH_2$— |
| A-548. | $CH_3CHF$ | 4-(4-$CH_3$—$C_6H_4$—O)—$C_6H_4$—$CH_2$— |
| A-549. | $CH_3CHF$ | 4-(4-$C_2H_5$—$C_6H_4$—O)—$C_6H_4$—$CH_2$— |
| A-550. | $CH_3CHF$ | 4-(4-n-$C_3H_7$—$C_6H_4$—O)—$C_6H_4$—$CH_2$— |
| A-551. | $CH_3CHF$ | 4-(4-iso-$C_3H_7$—$C_6H_4$—O)—$C_6H_4$—$CH_2$— |
| A-552. | $CH_3CHF$ | 4-(4-n-$C_4H_9$—$C_6H_4$—O)—$C_6H_4$—$CH_2$— |
| A-553. | $CH_3CHF$ | 4-(4-iso-$C_4H_9$—$C_6H_4$—O)—$C_6H_4$—$CH_2$— |

TABLE A-continued

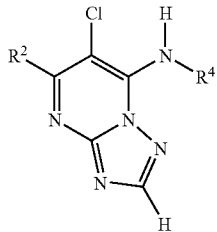
(Ia)

| No. | $R^2$ | $R^4$ |
|---|---|---|
| A-554. | $CH_3CHF$ | 4-(4-tert-$C_4H_9$—$C_6H_4$—O)—$C_6H_4$—$CH_2$— |
| A-555. | $CH_3CHF$ | 4-(4-$H_3C$—O—$C_6H_4$—O)—$C_6H_4$—$CH_2$— |
| A-556. | $CH_3CHF$ | 4-(4-$H_3C$—$H_2C$—O—$C_6H_4$—O)—$C_6H_4$—$CH_2$— |
| A-557. | $CH_3CHF$ | 4-(4-$H_3C$—$H_2C$—$H_2C$—O—$C_6H_4$—O)—$C_6H_4$—$CH_2$— |
| A-558. | $CH_3CHF$ | 4-(4-$H_3C$—$H_2C$—$H_2C$—$H_2C$—O—$C_6H_4$—O)—$C_6H_4$—$CH_2$— |
| A-559. | $CH_3CHF$ | 4-(4-tert-butoxy-$C_6H_4$—O)—$C_6H_4$—$CH_2$— |
| A-560. | $CH_3CHF$ | 4-(4-Cl—$C_6H_4$—O)—$C_6H_4$—$CH_2$— |
| A-561. | $CH_3CHF$ | 4-(4-Br—$C_6H_4$—O)—$C_6H_4$—$CH_2$— |
| A-562. | $CH_3CHF$ | 4-(3-$CH_3$—$C_6H_4$—O)—$C_6H_4$—$CH_2$— |
| A-563. | $CH_3CHF$ | 4-(3-$C_2H_5$—$C_6H_4$—O)—$C_6H_4$—$CH_2$— |
| A-564. | $CH_3CHF$ | 4-(3-n-$C_3H_7$—$C_6H_4$—O)—$C_6H_4$—$CH_2$— |
| A-565. | $CH_3CHF$ | 4-(3-iso-$C_3H_7$—$C_6H_4$—O)—$C_6H_4$—$CH_2$— |
| A-566. | $CH_3CHF$ | 4-(3-n-$C_4H_9$—$C_6H_4$—O)—$C_6H_4$—$CH_2$— |
| A-567. | $CH_3CHF$ | 4-(3-iso-$C_4H_9$—$C_6H_4$—O)—$C_6H_4$—$CH_2$— |
| A-568. | $CH_3CHF$ | 4-(3-tert-butyl-$C_6H_4$—O)—$C_6H_4$—$CH_2$— |
| A-569. | $CH_3CHF$ | 4-(3-$H_3C$—O—$C_6H_4$—O)—$C_6H_4$—$CH_2$— |
| A-570. | $CH_3CHF$ | 4-(3-$H_3C$—$H_2C$—O—$C_6H_4$—O)—$C_6H_4$—$CH_2$— |
| A-571. | $CH_3CHF$ | 4-(3-$H_3C$—$H_2C$—$H_2C$—O—$C_6H_4$—O)—$C_6H_4$—$CH_2$— |
| A-572. | $CH_3CHF$ | 4-(3-$H_3C$—$H_2C$—$H_2C$—$H_2C$—O—$C_6H_4$—O)—$C_6H_4$—$CH_2$— |
| A-573. | $CH_3CHF$ | 4-(3-tert-butoxy-$C_6H_4$—O)—$C_6H_4$—$CH_2$— |
| A-574. | $CH_3CHF$ | 4-(3-F—$C_6H_4$—O)—$C_6H_4$—$CH_2$— |
| A-575. | $CH_3CHF$ | 4-(3-Cl—$C_6H_4$—O)—$C_6H_4$—$CH_2$— |
| A-576. | $CH_3CHF$ | 4-(3-Br—$C_6H_4$—O)—$C_6H_4$—$CH_2$— |
| A-577. | $CH_3CHF$ | 4-(2-$CH_3$—$C_6H_4$—O)—$C_6H_4$—$CH_2$— |
| A-578. | $CH_3CHF$ | 4-(2-$C_2H_5$—$C_6H_4$—O)—$C_6H_4$—$CH_2$— |
| A-579. | $CH_3CHF$ | 4-(2-n-$C_3H_7$—$C_6H_4$—O)—$C_6H_4$—$CH_2$— |
| A-580. | $CH_3CHF$ | 4-(2-iso-$C_3H_7$—$C_6H_4$—O)—$C_6H_4$—$CH_2$— |
| A-581. | $CH_3CHF$ | 4-(2-n-$C_4H_9$—$C_6H_4$—O)—$C_6H_4$—$CH_2$— |
| A-582. | $CH_3CHF$ | 4-(2-iso-$C_4H_9$—$C_6H_4$—O)—$C_6H_4$—$CH_2$— |
| A-583. | $CH_3CHF$ | 4-(2-tert-butyl-$C_6H_4$—O)—$C_6H_4$—$CH_2$— |
| A-584. | $CH_3CHF$ | 4-(2-$H_3C$—O—$C_6H_4$—O)—$C_6H_4$—$CH_2$— |
| A-585. | $CH_3CHF$ | 4-(2-$H_3C$—$H_2C$—O—$C_6H_4$—O)—$C_6H_4$—$CH_2$— |
| A-586. | $CH_3CHF$ | 4-(2-$H_3C$—$H_2C$—$H_2C$—O—$C_6H_4$—O)—$C_6H_4$—$CH_2$— |
| A-587. | $CH_3CHF$ | 4-(2-$H_3C$—$H_2C$—$H_2C$—$H_2C$—O—$C_6H_4$—O)—$C_6H_4$—$CH_2$— |
| A-588. | $CH_3CHF$ | 4-(2-tert-butoxy-$C_6H_4$—O)—$C_6H_4$—$CH_2$— |
| A-589. | $CH_3CHF$ | 4-(2-F—$C_6H_4$—O)—$C_6H_4$—$CH_2$— |
| A-590. | $CH_3CHF$ | 4-(2-Cl—$C_6H_4$—O)—$C_6H_4$—$CH_2$— |
| A-591. | $CH_3CHF$ | 4-(2-Br—$C_6H_4$—O)—$C_6H_4$—$CH_2$— |
| A-592. | $CH_3CHF$ | 4-(3,4-$F_2$—$C_6H_3$—O)—$C_6H_4$—$CH_2$— |
| A-593. | $CH_3CHF$ | 4-(3,4-$Cl_2$—$C_6H_3$—O)—$C_6H_4$—$CH_2$— |
| A-594. | $CH_3CHF$ | 4-(3,4-$(CH_3)_2$—$C_6H_3$—O)—$C_6H_4$—$CH_2$— |
| A-595. | $CH_3CHF$ | 4-(3-F-4-Cl—$C_6H_3$—O)—$C_6H_4$—$CH_2$— |
| A-596. | $CH_3CHF$ | 4-(3-Cl-4-F—$C_6H_3$—O)—$C_6H_4$—$CH_2$— |
| A-597. | $CH_3CHF$ | 4-(3-$CH_3$-4-Cl—$C_6H_3$—O)—$C_6H_4$—$CH_2$— |
| A-598. | $CH_3CHF$ | 4-(3-Cl-4-$CH_3$—$C_6H_3$—O)—$C_6H_4$—$CH_2$— |
| A-599. | $CH_3CHF$ | 4-(3-Cl-4-Br—$C_6H_3$—O)—$C_6H_4$—$CH_2$— |
| A-600. | $CH_3CHF$ | 4-(3-$CH_3$-4-Br—$C_6H_3$—O)—$C_6H_4$—$CH_2$— |
| A-601. | $CH_3CHF$ | (±) phenyl-$CH(CH_3)$— |
| A-602. | $CH_3CHF$ | (R) phenyl-$CH(CH_3)$— |
| A-603. | $CH_3CHF$ | (S) phenyl-$CH(CH_3)$— |
| A-604. | $CH_3CHF$ | (±) 4-F-phenyl-$CH(CH_3)$— |
| A-605. | $CH_3CHF$ | (R) 4-F-phenyl-$CH(CH_3)$— |
| A-606. | $CH_3CHF$ | (S) 4-F-phenyl-$CH(CH_3)$— |
| A-607. | $CH_3CHF$ | (±) 4-Cl-phenyl-$CH(CH_3)$— |
| A-608. | $CH_3CHF$ | (R) 4-Cl-phenyl-$CH(CH_3)$— |
| A-609. | $CH_3CHF$ | (S) 4-Cl-phenyl-$CH(CH_3)$— |
| A-610. | $CH_3CHF$ | (±) 4-Br-phenyl-$CH(CH_3)$— |
| A-611. | $CH_3CHF$ | (R) 4-Br-phenyl-$CH(CH_3)$— |
| A-612. | $CH_3CHF$ | (S) 4-Br-phenyl-$CH(CH_3)$— |
| A-613. | $CH_3CHF$ | (±) 4-Cl-2-F-phenyl-$CH(CH_3)$— |
| A-614. | $CH_3CHF$ | (R) 4-Cl-2-F-phenyl-$CH(CH_3)$— |
| A-615. | $CH_3CHF$ | (S) 4-Cl-2-F-phenyl-$CH(CH_3)$— |
| A-616. | $CH_3CHF$ | (±) 6-Cl-2-F-phenyl-$CH(CH_3)$— |
| A-617. | $CH_3CHF$ | (R) 6-Cl-2-F-phenyl-$CH(CH_3)$— |
| A-618. | $CH_3CHF$ | (S) 6-Cl-2-F-phenyl-$CH(CH_3)$— |

TABLE A-continued (Ia)

| No. | R² | R⁴ |
|---|---|---|
| A-619. | CH₃CHF | (±) 2-F-phenyl-CH(CH₃)— |
| A-620. | CH₃CHF | (R) 2-F-phenyl-CH(CH₃)— |
| A-621. | CH₃CHF | (S) 2-F-phenyl-CH(CH₃)— |
| A-622. | CH₃CHF | (S) 2,4-F₂-phenyl-CH(CH₃)— |
| A-623. | CH₃CHF | (±) 2,4-F₂-phenyl-CH(CH₃)— |
| A-624. | CH₃CHF | (R) 2,4-F₂-phenyl-CH(CH₃)— |
| A-625. | CH₃CHF | (S) 2,5-F₂-phenyl-CH(CH₃)— |
| A-626. | CH₃CHF | (±) 2,5-F₂-phenyl-CH(CH₃)— |
| A-627. | CH₃CHF | (R) 2,5-F₂-phenyl-CH(CH₃)— |
| A-628. | CH₃CHF | (S) 2,6-F₂-phenyl-CH(CH₃)— |
| A-629. | CH₃CHF | (±) 2,6-F₂-phenyl-CH(CH₃)— |
| A-630. | CH₃CHF | (R) 2,6-F₂-phenyl-CH(CH₃)— |
| A-631. | CH₃CHF | (±) 2-CH₃O-phenyl-CH(CH₃)— |
| A-632. | CH₃CHF | (R) 2-CH₃O-phenyl-CH(CH₃)— |
| A-633. | CH₃CHF | (S) 2-CH₃O-phenyl-CH(CH₃)— |
| A-634. | CH₃CHF | (±) 4-CH₃O-phenyl-CH(CH₃)— |
| A-635. | CH₃CHF | (R) 4-CH₃O-phenyl-CH(CH₃)— |
| A-636. | CH₃CHF | (S) 4-CH₃O-phenyl-CH(CH₃)— |
| A-637. | CH₃CHF | (±) 4-H₅C₂—O-phenyl-CH(CH₃)— |
| A-638. | CH₃CHF | (R) 4-H₅C₂—O-phenyl-CH(CH₃)— |
| A-639. | CH₃CHF | (S) 4-H₅C₂—O-phenyl-CH(CH₃)— |
| A-640. | CH₃CHF | (±) 4-n-propoxy-phenyl-CH(CH₃)— |
| A-641. | CH₃CHF | (R) 4-n-propoxy-phenyl-CH(CH₃)— |
| A-642. | CH₃CHF | (S) 4-n-propoxy-phenyl-CH(CH₃)— |
| A-643. | CH₃CHF | (±) 4-n-butoxy-phenyl-CH(CH₃)— |
| A-644. | CH₃CHF | (R) 4-n-butoxyx-phenyl-CH(CH₃)— |
| A-645. | CH₃CHF | (S) 4-n-butoxyphenyl-CH(CH₃)— |
| A-646. | CH₃CHF | (±) 4-tert-butoxy-phenyl-CH(CH₃)— |
| A-647. | CH₃CHF | (R) 4-tert-butoxyx-phenyl-CH(CH₃)— |
| A-648. | CH₃CHF | (S) 4-tert-butoxyphenyl-CH(CH₃)— |
| A-649. | CH₃CHF | (±) 4-CH₃-phenyl-CH(CH₃)— |
| A-650. | CH₃CHF | (R) 4-CH₃-phenyl-CH(CH₃)— |
| A-651. | CH₃CHF | (S) 4-CH₃-phenyl-CH(CH₃)— |
| A-652. | CH₃CHF | (±) 4-C₂H₅-phenyl-CH(CH₃)— |
| A-653. | CH₃CHF | (R) 4-C₂H₅-phenyl-CH(CH₃)— |
| A-654. | CH₃CHF | (S) 4-C₂H₅-phenyl-CH(CH₃)— |
| A-655. | CH₃CHF | (±) 4-n-C₃H₇-phenyl-CH(CH₃)— |
| A-656. | CH₃CHF | (R) 4-n-C₃H₇-phenyl-CH(CH₃)— |
| A-657. | CH₃CHF | (S) 4-n-C₃H₇-phenyl-CH(CH₃)— |
| A-658. | CH₃CHF | (±) 4-iso-C₃H₇-phenyl-CH(CH₃)— |
| A-659. | CH₃CHF | (R) 4-iso-C₃H₇-phenyl-CH(CH₃)— |
| A-660. | CH₃CHF | (S) 4-iso-C₃H₇-phenyl-CH(CH₃)— |
| A-661. | CH₃CHF | (±) 4-n-C₄H₉-phenyl-CH(CH₃)— |
| A-662. | CH₃CHF | (R) 4-n-C₄H₉-phenyl-CH(CH₃)— |
| A-663. | CH₃CHF | (S) 4-n-C₄H₉-phenyl-CH(CH₃)— |
| A-664. | CH₃CHF | (±) 4-tert-C₄H₉-phenyl-CH(CH₃)— |
| A-665. | CH₃CHF | (R) 4-tert-C₄H₉-phenyl-CH(CH₃)— |
| A-666. | CH₃CHF | (S) 4-tert-C₄H₉-phenyl-CH(CH₃)— |
| A-667. | CH₃CHF | (±) 4-cycl.-C₆H₁₁-phenyl-CH(CH₃)— |
| A-668. | CH₃CHF | (R) 4-cycl.-C₆H₁₁-phenyl-CH(CH₃)— |
| A-669. | CH₃CHF | (S) 4-cycl.-C₆H₁₁-phenyl-CH(CH₃)— |
| A-670. | CH₃CHF | (±) 4-OCF₃-phenyl-CH(CH₃)— |
| A-671. | CH₃CHF | (R) 4-OCF₃-phenyl-CH(CH₃)— |
| A-672. | CH₃CHF | (S) 4-OCF₃-phenyl-CH(CH₃)— |
| A-673. | CH₃CHF | (±) 4-CF₃-phenyl-CH(CH₃)— |
| A-674. | CH₃CHF | (R) 4-CF₃-phenyl-CH(CH₃)— |
| A-675. | CH₃CHF | (S) 4-CF₃-phenyl-CH(CH₃)— |
| A-676. | CH₃CHF | (±) 3-F-phenyl-CH(CH₃)— |
| A-677. | CH₃CHF | (R) 3-F-phenyl-CH(CH₃)— |
| A-678. | CH₃CHF | (S) 3-F-phenyl-CH(CH₃)— |
| A-679. | CH₃CHF | (±) 3-Cl-phenyl-CH(CH₃)— |
| A-680. | CH₃CHF | (R) 3-Cl-phenyl-CH(CH₃)— |
| A-681. | CH₃CHF | (S) 3-Cl-phenyl-CH(CH₃)— |
| A-682. | CH₃CHF | (±) 3-Br-phenyl-CH(CH₃)— |
| A-683. | CH₃CHF | (R) 3-Br-phenyl-CH(CH₃)— |

TABLE A-continued

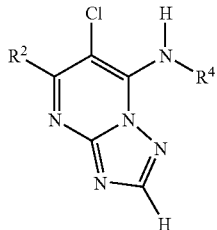

(Ia)

| No. | R² | R⁴ |
|---|---|---|
| A-684. | CH₃CHF | (S) 3-Br-phenyl-CH(CH₃)— |
| A-685. | CH₃CHF | (±) 3-CF₃-phenyl-CH(CH₃)— |
| A-686. | CH₃CHF | (R) 3-CF₃-phenyl-CH(CH₃)— |
| A-687. | CH₃CHF | (S) 3-CF₃-phenyl-CH(CH₃)— |
| A-688. | CH₃CHF | (±) 3,4-F₂-phenyl-CH(CH₃)— |
| A-689. | CH₃CHF | (R) 3,4-F₂-phenyl-CH(CH₃)— |
| A-690. | CH₃CHF | (S) 3,4-F₂-phenyl-CH(CH₃)— |
| A-691. | CH₃CHF | (±) 3,4-Cl₂-phenyl-CH(CH₃)— |
| A-692. | CH₃CHF | (R) 3,4-Cl₂-phenyl-CH(CH₃)— |
| A-693. | CH₃CHF | (S) 3,4-Cl₂-phenyl-CH(CH₃)— |
| A-694. | CH₃CHF | (±) 3,4-Br₂-phenyl-CH(CH₃)— |
| A-695. | CH₃CHF | (R) 3,4-Br₂-phenyl-CH(CH₃)— |
| A-696. | CH₃CHF | (S) 3,4-Br₂-phenyl-CH(CH₃)— |
| A-697. | CH₃CHF | (±) 4-Difluoromethoxyphenyl-CH(CH₃)— |
| A-698. | CH₃CHF | (R) 4-Difluoromethoxyphenyl-CH(CH₃)— |
| A-699. | CH₃CHF | (S) 4-Difluoromethoxyphenyl-CH(CH₃)— |
| A-700. | CH₃CHF | (±) 4-(1,1,2,2-tetrafluoroethoxy)phenyl-CH(CH₃)— |
| A-701. | CH₃CHF | (R) 4-(1,1,2,2-tetrafluoroethoxy)phenyl-CH(CH₃)— |
| A-702. | CH₃CHF | (S) 4-(1,1,2,2-tetrafluoroethoxy)phenyl-CH(CH₃)— |
| A-703. | CH₃CHF | (±) (5,5,7,7-tetramethylindan-2-yl)-CH(CH₃)— |
| A-704. | CH₃CHF | (R) (5,5,7,7-tetramethylindan-2-yl)-CH(CH₃)— |
| A-705. | CH₃CHF | (S) (5,5,7,7-tetramethylindan-2-yl)-CH(CH₃)— |
| A-706. | CH₃CHF | (±) (1,1,4,4,-tetramethyl-1,2,3,4-tetrahydronaphthalin-6-yl)-CH(CH₃)— |
| A-707. | CH₃CHF | (R) (1,1,4,4,-tetramethyl-1,2,3,4-tetrahydronaphthalin-6-yl)-CH(CH₃)— |
| A-708. | CH₃CHF | (S) (1,1,4,4,-tetramethyl-1,2,3,4-tetrahydronaphthalin-6-yl)-CH(CH₃)— |
| A-709. | CH₃CHF | (±) (1,1-dimethyl-1,2,3,4-tetrahydronaphthalin-6-yl)-CH(CH₃)— |
| A-710. | CH₃CHF | (R) (1,1-dimethyl-1,2,3,4-tetrahydronaphthalin-6-yl)-CH(CH₃)— |
| A-711. | CH₃CHF | (S) (1,1-dimethyl-1,2,3,4-tetrahydronaphthalin-6-yl)-CH(CH₃)— |
| A-712. | CH₃CHF | (±) (1,1,4,4,7-pentamethyl-1,2,3,4-tetrahydronaphthalin-6-yl)-CH(CH₃)— |
| A-713. | CH₃CHF | (R) (1,1,4,4,7-pentamethyl-1,2,3,4-tetrahydronaphthalin-6-yl)-CH(CH₃)— |
| A-714. | CH₃CHF | (S) (1,1,4,4,7-pentamethyl-1,2,3,4-tetrahydronaphthalin-6-yl)-CH(CH₃)— |
| A-715. | CH₃CHF | (±) (1,1,7-trimethyl-1,2,3,4-tetrahydronaphthalin-6-yl)-CH(CH₃)— |
| A-716. | CH₃CHF | (R) (1,1,7-trimethyl-1,2,3,4-tetrahydronaphthalin-6-yl)-CH(CH₃)— |
| A-717. | CH₃CHF | (S) (1,1,7-trimethyl-1,2,3,4-tetrahydronaphthalin-6-yl)-CH(CH₃)— |
| A-718. | CH₃CHF | (±) (2-methyl-1,3-dioxan-2-yl)-CH(CH₃)— |
| A-719. | CH₃CHF | (R) 2-methyl-1,3-dioxan-2-yl)-CH(CH₃)— |
| A-720. | CH₃CHF | (S) 2-methyl-1,3-dioxan-2-yl)-CH(CH₃)— |
| A-721. | CH₃CHF | (±) (2,5,5-trimethyl-1,3-dioxan-2-yl)-CH(CH₃)— |
| A-722. | CH₃CHF | (R) 2,5,5-trimethyl-1,3-dioxan-2-yl)-CH(CH₃)— |
| A-723. | CH₃CHF | (S) 2,5,5-trimethyl-1,3-dioxan-2-yl)-CH(CH₃)— |
| A-724. | CH₃CHF | (±) (2,2-difluorobenzodioxole-5-yl)CH(C₂H₅)— |
| A-725. | CH₃CHF | (R) (2,2-difluorobenzodioxole-5-yl)CH(C₂H₅)— |
| A-726. | CH₃CHF | (S) (2,2-difluorobenzodioxole-5-yl)CH(C₂H₅)— |
| A-727. | CH₃CHF | C₆H₅CH₂CH₂— |
| A-728. | CH₃CHF | 4-F—C₆H₄CH₂CH₂— |
| A-729. | CH₃CHF | 4-Cl—C₆H₄CH₂CH₂— |
| A-730. | CH₃CHF | 4-Br—C₆H₄CH₂CH₂— |
| A-731. | CH₃CHF | 4-CH₃O—C₆H₄CH₂CH₂— |
| A-732. | CH₃CHF | 4-C₂H₅O—C₆H₄CH₂CH₂— |
| A-733. | CH₃CHF | 4-n-C₃H₇O—C₆H₄CH₂CH₂— |
| A-734. | CH₃CHF | 4-n-C₄H₉O—C₆H₄CH₂CH₂— |
| A-735. | CH₃CHF | 4-t-C₄H₉O—C₆H₄CH₂CH₂— |
| A-736. | CH₃CHF | 3,4-(CH₃O)₂—C₆H₄CH₂CH₂— |

TABLE A-continued (Ia)

| No. | $R^2$ | $R^4$ |
|---|---|---|
| A-737. | $CH_3CHF$ | $4\text{-}H_3C\text{—}C_6H_4CH_2CH_2\text{—}$ |
| A-738. | $CH_3CHF$ | $4\text{-}H_3C\text{—}H_2C\text{—}C_6H_4CH_2CH_2\text{—}$ |
| A-739. | $CH_3CHF$ | $4\text{-}H_3C\text{—}H_2C\text{—}H_2C\text{—}C_6H_4CH_2CH_2\text{—}$ |
| A-740. | $CH_3CHF$ | $4\text{-}H_3C\text{—}H_2C\text{—}H_2C\text{—}H_2C\text{—}C_6H_4CH_2CH_2\text{—}$ |
| A-741. | $CH_3CHF$ | $4\text{-}(CH_3)_3C\text{—}C_6H_4CH_2CH_2\text{—}$ |
| A-742. | $CH_3CHF$ | $4\text{-}F_3CO\text{—}C_6H_4CH_2CH_2\text{—}$ |
| A-743. | $CH_3CHF$ | $4\text{-}F_3C\text{—}C_6H_4CH_2CH_2\text{—}$ |
| A-744. | $CH_3CHF$ | $3\text{-}F_3C\text{—}C_6H_4CH_2CH_2\text{—}$ |

Examples of compounds also are the 6-chloro-[1,2,4]triazolo-[1,5-a]pyrimidines of the formula Ib, where X is Cl, $R^1$ is $CH_3$ and $R^3$ is H, $R^2$ and $R^4$ together have the meanings given in one row of Table A.

Examples of compounds also are the 6-chloro-[1,2,4]triazolo-[1,5-a]pyrimidines of the formula Ic, where X is Cl, $R^1$ is $OCH_3$, $R^3$ is H, $R^2$ and $R^4$ together have the meanings given in one row of Table A.

Examples of compounds also are the 6-chloro-[1,2,4]triazolo-[1,5-a]pyrimidines of the formula, where X is Cl, $R^1$ is $SCH_3$, $R^3$ is H, $R^2$ and $R^4$ together have the meanings given in one row of Table A.

Examples of compounds also are the 6-chloro-[1,2,4]triazolo-[1,5-a]pyrimidines of the formula I, where X is Cl, $R^1$ is $SOCH_3$, $R^3$ is H, $R^2$ and $R^4$ together have the meanings given in one row of Table A.

Examples of compounds also are the 6-chloro-[1,2,4]triazolo-[1,5-a]pyrimidines of the formula I, where X is Cl, $R^1$ is $SO_2CH_3$, $R^3$ is H, $R^2$ and $R^4$ together have the meanings given in one row of Table A.

Examples of compounds also are the 6-chloro-[1,2,4]triazolo-[1,5-a]pyrimidines of the formula I, where X is Cl, $R^1$ is $CF_3$, $R^3$ is H, $R^2$ and $R^4$ together have the meanings given in one row of Table A.

Examples of compounds also are the 6-chloro-[1,2,4]triazolo-[1,5-a]pyrimidines of the formula I, where X is Cl, $R^1$ is CN, $R^3$ is H, $R^2$ and $R^4$ together have the meanings given in one row of Table A.

Examples of compounds also are the 6-chloro-[1,2,4]triazolo-[1,5-a]pyrimidines of the formula I, where X is Cl, $R^1$ is OH, $R^3$ is H, $R^2$ and $R^4$ together have the meanings given in one row of Table A.

Examples of compounds also are the 6-chloro-[1,2,4]triazolo-[1,5-a]pyrimidines of the formula I, where X is Cl, $R^1$ is $OCHF_2$, $R^3$ is H, $R^2$ and $R^4$ together have the meanings given in one row of Table A.

Examples of compounds also are the 6-chloro-[1,2,4]triazolo-[1,5-a]pyrimidines of the formula I, where X is Cl, $R^1$ is $OCF_2CHF_2$, $R^3$ is H, $R^2$ and $R^4$ together have the meanings given in one row of Table A.

Examples of compounds also are the 6-chloro-[1,2,4]triazolo-[1,5-a]pyrimidines of the formula I, where X is Cl, $R^1$ is $OCF_3$, $R^3$ is H, $R^2$ and $R^4$ together have the meanings given in one row of Table A.

Examples of compounds also are the 6-chloro-[1,2,4]triazolo-[1,5-a]pyrimidines of the formula I, where X is Cl, $R^1$ is $OCH_2C_6H_5$, $R^3$ is H, $R^2$ and $R^4$ together have the meanings given in one row of Table A.

Examples of compounds also are the 6-chloro-[1,2,4]triazolo-[1,5-a]pyrimidines of the formula I, where X is Cl, $R^1$ is $OCH_2CH_3$, $R^3$ is H, $R^2$ and $R^4$ together have the meanings given in one row of Table A.

Examples of compounds also are the 6-chloro-[1,2,4]triazolo-[1,5-a]pyrimidines of the formula I, where X is Cl, $R^1$ is $OCH_2C{=}CH$, $R^3$ is H, $R^2$ and $R^4$ together have the meanings given in one row of Table A.

Examples of compounds also are the 6-chloro-[1,2,4]triazolo-[1,5-a]pyrimidines of the formula I, where X is Cl, $R^1$ is $OCH(CH_3)_2$, $R^3$ is H, $R^2$ and $R^4$ together have the meanings given in one row of Table A.

Examples of compounds also are the 6-chloro-[1,2,4]triazolo-[1,5-a]pyrimidines of the formula I, where X is Cl, $R^1$ is $O\text{—}CH_2CH_2\text{—}O\text{—}CH_3$, $R^3$ is H, $R^2$ and $R^4$ together have the meanings given in one row of Table A.

Examples of compounds also are the 6-chloro-[1,2,4]triazolo-[1,5-a]pyrimidines of the formula I, where X is Cl, $R^1$ is $O\text{—}CH_2CH_2\text{—}O\text{—}CH_2CH_2\text{—}O\text{—}CH_3$, $R^3$ is H, $R^2$ and $R^4$ together have the meanings given in one row of Table A.

Examples of compounds also are the 6-chloro-[1,2,4]triazolo-[1,5-a]pyrimidines of the formula I, where X is Cl, $R^1$ is $S\text{—}CH_2CH_2\text{—}O\text{—}CH_3$, $R^3$ is H, $R^2$ and $R^4$ together have the meanings given in one row of Table A.

Examples of compounds also are the 6-chloro-[1,2,4]triazolo-[1,5-a]pyrimidines of the formula I, where X is Cl, $R^1$ is $S\text{—}CH_2C(O)\text{—}O\text{—}CH_3$, $R^3$ is H, $R^2$ and $R^4$ together have the meanings given in one row of Table A.

Examples of compounds also are the 6-chloro-[1,2,4]triazolo-[1,5-a]pyrimidines of the formula I, where X is Cl, $R^1$ is $S\text{—}CH_2CH_2C(O)\text{—}O\text{—}CH_3$, $R^3$ is H, $R^2$ and $R^4$ together have the meanings given in one row of Table A.

Examples of compounds also are the 6-chloro-[1,2,4]triazolo-[1,5-a]pyrimidines of the formula I, where X is Cl, $R^1$ is $S\text{—}CH_2C(O)\text{—}OH$, $R^3$ is H, $R^2$ and $R^4$ together have the meanings given in one row of Table A.

The 6-halogeno-[1,2,4]triazolo-[1,5-a]pyrimidines of the formula I according to the present invention can be prepared, for example, similarly to a process described in Pharmazie, 1971, 26, 534 ff or in DD 99 794. The synthesis is shown in Scheme 1.

Scheme 1:

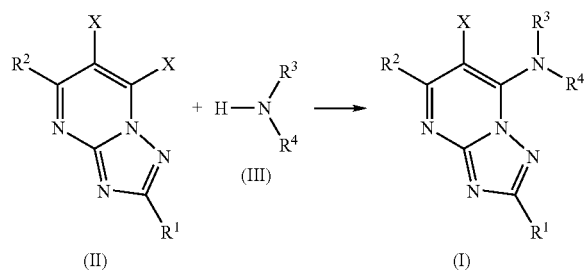

In Scheme 1, the variables $R^1$, $R^2$, $R^3$, $R^4$ and X are as defined above. The reaction of a 6,7-dihalogeno-[1,2,4]triazolo-[1,5-a]pyrimidine of the formula II with an amine of the formula III may be carried out in the presence or absence of a solvent. Suitable solvents are all solvents which are inert under the reaction conditions, such as aliphatic, cycloaliphatic or aromatic hydrocarbons such as hexane, petrol ether, cyclohexane, benzene, toluene, xylenes, ethers, for example dialkyl ethers, such as diethyl ether, methyl tert-butyl ether, cyclic ethers, such as tetrahydrofuran or dioxane, halogenated hydrocarbons such as dichloromethane or trichloromethane or $C_1$-$C_4$-alkanols such as methanol, ethanol, n-propanol, iso-propanol, n-butanol or tert-butanol, water or mixtures of these solvents. It is preferred that the reaction is carried out in the presence of a solvent. If the reaction is carried out in the absence of a solvent, the amine (III) is employed in a large excess, based on 6,7-dihalogeno-[1,2,4]triazolo-[1,5-a]pyrimidin II.

It is also preferred that the reaction is carried out in the presence of a base. Suitable bases include organic bases, for example tertiary amines, such as trimethylamine, triethylamine, diisopropylethylamine and N-methylpiperidine, pyridine, substituted pyridines such as collidine, 2,3-lutidine, 2,4-lutidine or 2,5-lutidine and inorganic bases, for example alkali metal carbonates and alkaline earth metal carbonates such as lithium carbonate, potassium carbonate and sodium carbonate, calcium carbonate and alkali metal hydrogencarbonates such as sodium hydrogen carbonate. An excess of the amine III may serve as base.

The reaction temperature is usually in the range of from 0° C. to the boiling of the solvent, preferably of from 20 to the 120° C.

The molar ratio of amine III to 6,7-dihalogeno-[1,2,4]triazolo-[1,5-a]pyrimidine II is generally at least 0.9:1, preferably at least 1:1. It may be advantageous to employ the amine III in a slight excess, for example of up to 20%, based on the 6,7-dihalogeno-[1,2,4]triazolo-[1,5-a]pyrimidine II.

In general, the base is employed in at least equimolar amount to a 2-fold molar excess, based on the 6,7-dihalogeno-[1,2,4]triazolo-[1,5-a]pyrimidine II. It may be advantageous to employ the base in a slight excess, for example up to 30%, based on the 6,7-dihalogeno-[1,2,4]triazolo-[1,5-a]pyrimidine II.

The reaction mixtures are worked up in a customary manner, for example by adding diluted acids, for example mineral acids such as diluted hydrochloric acid, hydrobromic acid and sulfuric acid or aqueous organic acids such as trifluoroacetic acid or acetic acid, aqueous hydrochloric acid being preferred, phase separation and, if appropriate, chromatographic purification, recrystallization, trituration or digestion. The compounds according to the present invention are in general oils, resinous compounds or predominantly crystalline solid materials.

From the preparation, the compounds of formula I may be obtained as isomer mixtures (stereoisomers, enantiomers). If desired, these can be resolved by the methods customary for this purpose, such as crystallization or chromatography, also on optically active adsorbate, to give the pure isomers.

Some of the amines of the formula III which are employed as starting materials are commercially available. Other may be prepared by processes known in the art, for example, by conversion of the corresponding alcohols into its tosylates which are then converted to the phthalimido derivatives. The phthalimido derivatives are converted to the desired amines by using hydrazine or any other suitable cleavage agent using conventional methods [e.g. J. Am. Soc., Vol. 117, p. 7025 (1995); WO 93/20804]; by reduction of the corresponding nitriles [see, Heterocycles, Vol. 35, p. 2 (1993); Synthetic Commun., Vol. 25, p. 413 (1995); Tetrahedron Lett., p. 2933 (1995)], or by reductive amination of ketones (see, J. Am. Chem. Soc., Vol. 122, p. 9556 (2000); Org. Lett., p. 731 (2001), J. Med. Chem., p. 1566 (1988); by conversion of the appropriate halogenides and, if appropriate, followed by alkylation. Alternatively, the amine may be carried out by addition of Grignard reagents to imines (see R. B. Moffett, Org. Synth. IV, 605 (1963)). Furthermore, the radical $R^4$ may be introduced by Grignard reaction to nitriles or carboxylic acid anhydrides (see J. Org. Chem. p. 5056 (1992); Tetrahedron Lett., S. 29933 (1995)). If individual amines III are not disclosed in the cited literature they can be either obtained by routes described above or they can be prepared by derivatization of other compounds III or by customary modifications of the synthesis routes described above.

The starting materials of the formula II may be prepared in two steps, in analogy to the process described in Chem. Pharm. Bull. 1959, Vol. 7, p. 903. The synthesis is shown in Scheme 2.

Scheme 2:

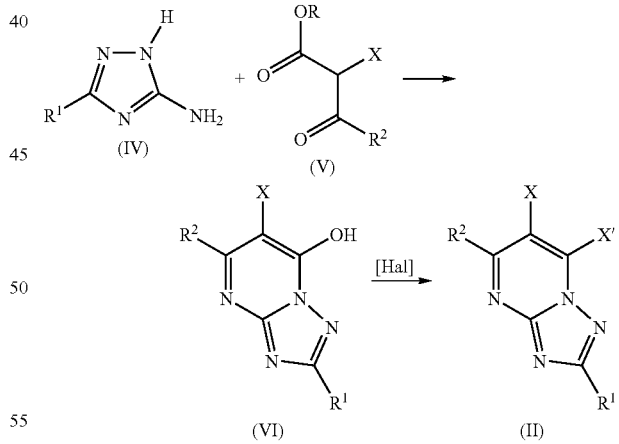

In Scheme 2, the variables $R^1$, $R^2$ and X are as defined above, X' is halogen, R is alkyl, preferably $C_1$-$C_6$-alkyl, in particular methyl or ethyl and Hal means a halogenating agent. In the first step the 5-aminotriazole of the general formula IV is reacted with the malonic ester of the general formula V. The reaction may be carried out under alkaline conditions, preferably using high boiling tertiary amines as for example tri-n-butylamine. The 5-aminotriazoles IV are commercially available or can be prepared in analogy to the methods which are well known in the art.

In the second step of Scheme 2 the resulting 6-halogeno-7-hydroxy-[1,2,4]triazolo[1,5-a]pyrimidine of the general formula VI is treated with a halogenating agent, preferably with a brominating or chlorinating agent. Suitable halogenating agents include inorganic acid halides, preferably acid chlorides or acide bromides such as thionyl chloride, thionyl bromide, phosphorus oxychloride, sulfuryl chloride, phosphorus pentachloride or phosphorus tribromide, phosphorus trichloride and mixtures of these. If phosphorus oxychloride is used as a halogenating agent, the reaction is preferably carried out in the presence of a mineral acid, such as polyphosphoric acid and pyridinium salts such as pyridinium bromide or chloride. Preferred halogenating agents are $POCl_3$, $PCl_3/Cl_2$ or $PCl_5$ and mixtures of these. The reaction can be carried out in the presence or absence of a solvent. The acid halides thionylchloride, phoshorus trichloride or phosphoryl chloride may simultaneously act as solvent. Suitable solvents are furthermore acetonitrile or dichloromethane. The halogenating agent is generally used in at least equimolar amounts, based on the 6-halogeno-7-hydroxy-[1,2,4]triazolo[1,5-a]pyrimidine of the general formula VI. The reaction is suitable carried out at a temperature in the range from 0° C. to 150° C., the preferred reaction temperature being from 80° C. to 125° C.

Due to their excellent activity, the compounds of the general formula I may be used for controlling animal pests. Animal pests include harmful insects, acaridae and arachnids Accordingly, the invention further provides agriculturally composition for combating animal pests, especially insects, arachnids and/or acaridae which comprises such an amount of at least one compound of the general formula I or at least an agriculturally useful salt of I and at least one inert liquid and/or solid agronomically acceptable carrier that it has a pesticidal action and, if desired, at least one surfactant.

Such a composition may contain a single active compound of the general formula I or a mixture of several active compounds I according to the present invention. The composition according to the present invention may comprise an individual isomer or mixtures of isomers.

The 6-halogeno-[1,2,4]triazolo[1,5-a]pyrimidines and the pestidicidal compositions comprising them are effective agents for controlling animal pests. Animal pests controlled by the compounds of formula I include for example:

insects from the order of the lepidopterans (Lepidoptera), for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis;* beetles (Coleoptera), for example *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus, Crioceris asparagi, Diabrotica longicomis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllotreta chrysocephala, Phyllophaga* sp., *Phyllopertha horticola, Phyllotreta nemorum, Phyllotreta striolata, Popillia japonica, Sitona lineatus* and *Sitophilus granaria;* dipterans (Diptera), for example *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea* and *Tipula paludosa;* thrips (Thysanoptera), e.g. *Dichromothrips corbettf Frankliniella fusca, Frankliniella occidentalis, Frankliniella tritici, Scirtothrips citri, Thrips oryzae, Thrips palmi* and *Thrips tabaci;* hymenopterans (Hymenoptera), e.g. *Athalia rosae, Atta cephalotes, Atta sexdens, Atta texana, Hoplocampa minuta, Hoplocampa testudinea, Monomorium pharaonis, Solenopsis geminata* and *Solenopsis invicta;* heteropterans (Heteroptera), e.g. *Acrostemum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis* and *Thyanta perditor,* homopterans (Homoptera), e.g. *Acyrthosiphon onobrychis, Adelges laricis, Aphidula nasturtii, Aphis fabae, Aphis forbesi, Aphis pomi, Aphis gossypii, Aphis grossulariae, Aphis schneideri, Aphis spiraecola, Aphis sambuci, Acyrthosiphon pisum, Aulacorthum solani, Bemisia argentifolii, Brachycaudus cardui, Brachycaudus helichrysi, Brachycaudus persicae, Brachycaudus prunicola, Brevicoryne brassicae, Capitophorus horni, Cerosipha gossypii, Chaetosiphon fragaefomi, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopol-*

*ophium dirhodum, Myzodes persicae, Myzus ascalonicus, Myzus cerasi, Myzus persicae, Myzus varians, Nasonovia ribis-nigri, Nilaparvata lugens, Pemphigus bursarius, Perkinsiella saccharicida, Phorodon humuli, Psylla mali, Psylla piri, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Sogatella furcifera Trialeurodes vaporariorum, Toxoptera aurantiiand*, and *Viteus vitifolii;* termites (Isoptera), e.g. *Calotermes flavicollis, Leucotermes flavipes, Reticulitermes flavipes, Reticulitermes lucifugus* und *Termes natalensis;* orthopterans (Orthoptera), e.g. *Acheta domestica, Blatta orientalis, Blattella germanica, Forficula auricularia, Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus* and *Tachycines asynamorus;*

Arachnoidea, such as arachnids (Acarina), e.g. of the families Argasidae, Ixodidae and Sarcoptidae, such as *Amblyomma americanum, Amblyomma variegatum, Argas persicus, Boophilus annulatus, Boophilus decoloratus, Boophilus microplus, Dermacentor silvarum, Hyalomma truncatum, Ixodes ricinus, Ixodes rubicundus, Omithodorus moubata, Otobius megnini, Dermanyssus gallinae, Psoroptes ovis, Rhipicephalus appendiculatus, Rhipicephalus evertsi, Sarcoptes scabiei,* and *Eriophyidae* spp. such as *Aculus schlechtendali, Phyllocoptrata oleivora* and *Eriophyes sheldoni; Tarsonemidae* spp. such as *Phytonemus pallidus* and *Polyphagotarsonemus latus; Tenuipalpidae* spp. such as *Brevipalpus phoenicis; Tetranychidae* spp. such as *Tetranychus cinnabarinus, Tetranychus kanzawai, Tetranychus pacificus, Tetranychus telarius* and *Tetranychus urticae, Panonychus ulmi, Panonychus citri,* and *oligonychus pratensis;*

Siphonatera, e.g. *Xenopsylla cheopsis, Ceratophyllus* spp.

The compounds of the formula I are preferably used for controlling pests of the orders Lepidoptera, Coleoptera, Homoptera and Acarina.

The compounds of formula (I) or the pesticidal compositions comprising them may be used to protect growing plants and crops from attack or infestation by animal pests, especially insects, acaridae or arachnids by contacting the plant/crop with a pesticidally effective amount of compounds of formula (I). The term "crop" refers both to growing and harvested crops.

The animal pest, especially the insect, acaridae, arachnid, plant and/or soil or water in which the plant is growing can be contacted with the present compound(s) I or composition(s) containing them by any application method known in the art. As such, "contacting" includes both direct contact (applying the compounds/compositions directly on the animal pest, especially the insect, acaridae and/or arachnid, and/or plant—typically to the foliage, stem or roots of the plant) and indirect contact (applying the compounds/compositions to the locus of the animal pest, especially the insect, acaridae, and/or arachnid, and/or plant).

Moreover, animal pests, especially insects, acaridae or arachnids may be controlled by contacting the target pest, its food supply or its locus with a pesticidally effective amount of compounds of formula (I). As such, the application may be carried out before or after the infection of the locus, growing crops, or harvested crops by the pest.

"Locus" means a habitat, breeding ground, plant, seed, soil, area, material or environment in which a pest or parasite is growing or may grow.

Effective amounts suitable for use in the method of invention may vary depending upon the particular formula I compound, target pest, method of application, application timing, weather conditions, animal pest habitat, especially insect, arachnid or acarid habitat, or the like. In general, for use in treating crop plants, the rate of application of the compounds I and/or compositions according to this invention may be in the range of about 0.1 g to about 4000 g per hectare, desirably from about 25 g to about 600 g per hectare, more desirably from about 50 g to about 500 g per hectare. For use in treating seeds, the typical rate of application is of from about 1 g to about 500 g per kilogram of seeds, desirably from about 2 g to about 300 g per kilogram of seeds, more desirably from about 10 g to about 200 g per kilogram of seeds. Customary application rates in the protection of materials are, for example, from about 0.001 g to about 2000 g, desirably from about 0.005 g to about 1000 g, of active compound per cubic meter of treated material.

The compounds I or the pesticidal compositions comprising them can be used, for example in the form of solutions, emulsions, microemulsions, suspensions, flowable concentrates, dusts, powders, pastes and granules. The use form depends on the particular purpose; in any case, it should guarantee a fine and uniform distribution of the compound according to the invention.

The pesticidal composition for combating animal pests, especially insects, acaridae and/or arachnids contains such an amount of at least one compound of the general formula I or an agriculturally useful salt of I and auxiliaries which are usually used in formulating pesticidal composition.

The formulations are prepared in a known manner, e.g. by extending the active ingredient with solvents and/or carriers, if desired using emulsifiers and dispersants, it also being possible to use other organic solvents as auxiliary solvents if water is used as the diluent. Auxiliaries which are suitable are essentially: solvents such as aromatics (e.g. xylene), chlorinated aromatics (e.g. chlorobenzenes), paraffins (e.g. mineral oil fractions), alcohols (e.g. methanol, butanol), ketones (e.g. cyclohexanone), amines (e.g. ethanolamine, dimethylformamide) and water; carriers such as ground natural minerals (e.g. kaolins, clays, talc, chalk) and ground synthetic minerals (e.g. highly-disperse silica, silicates); emulsifiers such as non-ionic and anionic emulsifiers (e.g. polyoxyethylene fatty alcohol ethers, alkylsulfonates and arylsulfonates) and dispersants such as lignin-sulfite waste liquors and methylcellulose.

Suitable surfactants are alkali metal, alkaline earth metal and ammonium salts of lignosulfonic acid, naphthalenesulfonic acid, phenolsulfonic acid, dibutyinaphthalenesulfonic acid, alkylarylsulfonates, alkyl sulfates, alkylsulfonates, fatty alcohol sulfates and fatty acids and their alkali metal and alkaline earth metal salts, salts of sulfated fatty alcohol glycol ether, condensates of sulfonated naphthalene and naphthalene derivatives with formaldehyde, condensates of naphthalene or of napthalenesulfonic acid with phenol or formaldehyde, polyoxyethylene octylphenyl ether, ethoxylated isooctylphenol, octylphenol, nonylphenol, alkylphenol polyglycol ethers, tributylphenyl polyglycol ethers, alkylaryl polyether alcohols, isotridecyl alcohol, fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, e.g. benzene, toluene, xylene, paraffin, tetrahydronaphthalene, alkylated naphthalenes or their derivatives, methanol, ethanol, propanol, butanol, chloroform, carbon tetrachloride, cyclohexanol, cyclohexanone, chlorobenzene, isophorone, strongly polar solvents, e.g. dimethylformamide, dimethyl sulfoxide, N-methylpyrrolidone and water.

Powders, materials for scattering and dusts can be prepared by mixing or concomitantly grinding the active substances with a solid carrier.

Granules, e.g. coated granules, compacted granules, impregnated granules and homogeneous granules, can be prepared by binding the active ingredients to solid carriers. Examples of solid carriers are mineral earths, such as silicas, silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, e.g. ammonium sulfate, ammonium phosphate, ammonium nitrate, ureas, and products of vegetable origin, such as cereal meal, tree bark meal, wood meal and nutshell meal, cellulose powders and other solid carriers.

Such formulations or compositions of the present invention include a formula I compound of this invention (or combinations thereof) admixed with one or more agronomically acceptable inert, solid or liquid carriers. Those compositions contain a pesticidally effective amount of said compound or compounds, which amount may vary depending upon the particular compound, target pest, and method of use.

In general, the formulations comprise of from 0.01 to 95% by weight, preferably from 0.1 to 90% by weight, of the active ingredient. The active ingredients are employed in a purity of from 90% to 100%, preferably 95% to 100% (according to NMR spectrum).

The following are exemplary formulations:

I. 5 parts by weight of a compound according to the invention are mixed intimately with 95 parts by weight of finely divided kaolin. This gives a dust which comprises 5% by weight of the active ingredient.

II. 30 parts by weight of a compound according to the invention are mixed intimately with a mixture of 92 parts by weight of pulverulent silica gel and 8 parts by weight of paraffin oil which had been sprayed onto the surface of this silica gel. This gives a formulation of the active ingredient with good adhesion properties (comprises 23% by weight of active ingredient).

III. 10 parts by weight of a compound according to the invention are dissolved in a mixture composed of 90 parts by weight of xylene, 6 parts by weight of the adduct of 8 to 10 mol of ethylene oxide and 1 mol of oleic acid N-monoethanolamide, 2 parts by weight of calcium dodecylbenzenesulfonate and 2 parts by weight of the adduct of 40 mol of ethylene oxide and 1 mol of castor oil (comprises 9% by weight of active ingredient).

IV. 20 parts by weight of a compound according to the invention are dissolved in a mixture composed of 60 parts by weight of cyclohexanone, 30 parts by weight of isobutanol, 5 parts by weight of the adduct of 7 mol of ethylene oxide and 1 mol of isooctylphenol and 5 parts by weight of the adduct of 40 mol of ethylene oxide and 1 mol of castor oil (comprises 16% by weight of active ingredient).

V. 80 parts by weight of a compound according to the invention are mixed thoroughly with 3 parts by weight of sodium diisobutylnaphthalene-alpha-sulfonate, 10 parts by weight of the sodium salt of a lignosulfonic acid from a sulfite waste liquor and 7 parts by weight of pulverulent silica gel, and the mixture is ground in a hammer mill (comprises 80% by weight of active ingredient).

VI. 90 parts by weight of a compound according to the invention are mixed with 10 parts by weight of N-methyl-α-pyrrolidone, which gives a solution which is suitable for use in the form of microdrops (comprises 90% by weight of active ingredient).

VII. 20 parts by weight of a compound according to the invention are dissolved in a mixture composed of 40 parts by weight of cyclohexanone, 30 parts by weight of isobutanol, 20 parts by weight of the adduct of 7 mol of ethylene oxide and 1 mol of isooctylphenol and 10 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

VIII. 20 parts by weight of a compound according to the invention are mixed thoroughly with 3 parts by weight of sodium diisobutylnaphthalene-α-sulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active ingredient.

The active ingredients can be used as such, in the form of their formulations or the use forms prepared therefrom, e.g. in the form of directly sprayable solutions, powders, suspensions or dispersions, emulsions, oil dispersions, pastes, dusts, materials for spreading, or granules, by means of spraying, atomizing, dusting, scattering or pouring. The use forms depend entirely on the intended purposes; in any case, this is intended to guarantee the finest possible distribution of the active ingredients according to the invention.

Aqueous use forms can be prepared from emulsion concentrates, pastes or wettable powders (sprayable powders, oil dispersions) by adding water. To prepare emulsions, pastes or oil dispersions, the substances as such or dissolved in an oil or solvent, can be homogenized in water by means of wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active ingredient concentrations in the ready-to-use products can be varied within substantial ranges. In general, they are from 0.0001 to 10%, preferably from 0.01 to 1%.

The active ingredients may also be used successfully in the ultra-low-volume process (ULV), it being possible to apply formulations comprising over 95% by weight of active ingredient, or even the active ingredient without additives.

Compositions to be used according to this invention may also contain other active ingredients, for example other pesticides, insecticides, herbicides, fungicides, other pesticides, or bactericides, fertilizers such as ammonium nitrate, urea, potash, and superphosphate, phytotoxicants and plant growth regulators, safeners and nematicides. These additional ingredients may be used sequentially or in combination with the above-described compositions, if appropriate also added only immediately prior to use (tank mix). For example, the plant(s) may be sprayed with a composition of this invention either before or after being treated with other active ingredients.

These agents can be admixed with the agents used according to the invention in a weight ratio of 1:10 to 10:1. Mixing the compounds I or the compositions comprising them in the use form as pesticides with other pesticides frequently results in a broader pesticidal spectrum of action.

The following list of pesticides together with which the compounds of formula I can be used, is intended to illustrate the possible combinations, but not to impose any limitation:

Organophosphates: Acephate, Azinphos-methyl, Chlorpyrifos, Chlorfenvinphos, Diazinon, Dichlorvos, Dicrotophos, Dimethoate, Disulfoton, Ethion, Fenitrothion, Fenthion, Isoxathion, Malathion, Methamidophos, Methidathion, Methyl-Parathion, Mevinphos, Monocrotophos, Oxydemeton-methyl, Paraoxon, Parathion, Phenthoate, Phosalone, Phosmet, Phosphamidon, Phorate, Phoxim, Pirimiphos-methyl, Profenofos, Prothiofos, Sulprophos, Triazophos, Trichlorfon;

Carbamates: Alanycarb, Benfuracarb, Carbaryl, Carbosulfan, Fenoxycarb, Furathiocarb, Indoxacarb, Methiocarb, Methomyl, Oxamyl, Pirimicarb, Propoxur, Thiodicarb, Triazamate;

Pyrethroids: Bifenthrin, Cyfluthrin, Cypermethrin, Deltamethrin, Esfenvalerate, Ethofenprox, Fenpropathrin, Fenvalerate, Cyhalothrin, Lambda-Cyhalothrin, Permethrin, Silafluofen, Tau-Fluvalinate, Tefluthrin, Tralomethrin, Zeta-Cypermethrin;

Arthropod growth regulators: a) chitin synthesis inhibitors: benzoylureas: Chlorfluazuron, Diflubenzuron, Flucycloxuron, Flufenoxuron, Hexaflumuron, Lufenuron, Novaluron, Teflubenzuron, Triflumuron; Buprofezin, Diofenolan, Hexythiazox, Etoxazole, Clofentazine; b) ecdysone antagonists: Halofenozide, Methoxyfenozide, Tebufenozide; c) juvenoids: Pyriproxyfen, Methoprene, Fenoxycarb; d) lipid biosynthesis inhibitors: Spirodiclofen;

Various: Abamectin, Acequinocyl, Amitraz, Azadirachtin, Bifenazate, Cartap, Chlorfenapyr, Chlordimeform, Cyromazine, Diafenthiuron, Dinetofuran, Diofenolan, Emamectin, Endosulfan, Ethiprole, Fenazaquin, Fipronil, Formetanate, Formetanate hydrochloride, Hydramethylnon, Imidacloprid, Indoxacarb, Pyridaben, Pymetrozine, Spinosad, Sulfur, Tebufenpyrad, Thiamethoxam, and Thiocyclam.

The present invention is now illustrated in further detail by the following examples.

1. SYNTHESIS EXAMPLES

Example 1

(cis-4-tert-butyl-cyclohexyl)-[6-chloro-5-ethyl-[1,2,4]triazolo[1,5-a]pyrimidin-7-yl]-amine

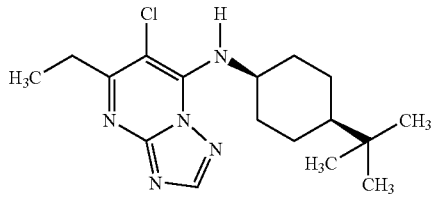 [SMILES: CCc1nc2ncnn2c(N[C@H]2CC[C@@H](C(C)(C)C)CC2)c1Cl]

0.280 g (2.76 mmol) Triethylamine, a spatula tip of tetrabutylammonium iodide and 0.393 g (2.53 mmol) of cis-4-tert-butylcyclohexylamine were added successively to a solution of 0.500 g (2.3 mmol) of 5-ethyl-6,7-dichloro-[1,2,4]triazolo[1,5-a]pyrimidine in 10 ml of toluene under stirring. The reaction mixture was heated at reflux for 5 hours and then stirred for another 12 hours at room temperature. The solvent was evaporated under reduced pressure and dichloromethane was added to the resulting residue. The resulting reaction mixture was washed with 2N hydrochloric acid and water. The organic phase was separated, dried and the solvent was evaporated under reduced pressure. Treatment of the resulting residue with hexane yielded 0.420 g (1.2 mmol, 52% of theory) of the title compound having a melting point of 120-122° C.

$^1$H-NMR (CDCl$_3$) δ: 8.25 (s, 1H), 6.20 (m, 1H), 5.20 (m, 1H), 3.00 (q, 2H), 2.05 (d, 2H), 1.85 (s, 1H), 1.70 (t, 4H), 1.35 (t, 3H), 1.30-1.10 (m, 2H), 0.90 (s, 9H).

Example 2

(cis-4-tert-butyl-cyclohexyl)-[6-chloro-5-(1-fluoroethyl)-[1,2,4]triazolo[1,5-a]pyrimidin-7-yl]-amine

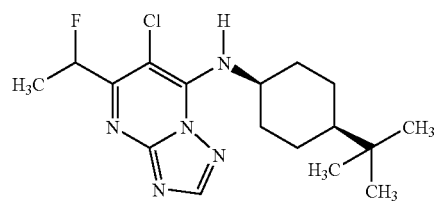 [SMILES: CC(F)c1nc2ncnn2c(N[C@H]2CC[C@@H](C(C)(C)C)CC2)c1Cl]

0.220 g (2.2 mmol) Triethylamine, a spatula tip of tetrabutylammonium iodide and 0.340 g (2.2 mmol) of cis-4-tert-butylcyclohexylamine were added successively to a solution of 0.470 g (2.0 mmol) of 5-(1-fluoroethyl)-6,7-dichloro-[1,2,4]triazolo[1,5-a]pyrimidine in 15 ml of toluene under stirring. The reaction mixture was heated at reflux for 5 hours and then stirred for another 12 hours at room temperature. The solvent was evaporated under reduced pressure and dichloromethane was added to the resulting residue. The resulting reaction mixture was washed with 2N hydrochloric acid and water. The organic phase was separated, dried and the solvent was evaporated under reduced pressure. Treatment of the resulting residue with hexane yielded 0.540 g (1.5 mmol, 76% of theory) of the title compound having a melting point of 138-139° C.

$^1$H-NMR (CDCl$_3$) δ: 8.35 (s, 1H), 6.35 (bd, 1H), 6.00 (dq, 1H), 5.25 (bm, 1H), 2.00 (bd, 2H), 1.75 (dd, 3H), 1.70 (m, 3H), 1.30-1.10 (m, 4H), 0.90 (s, 9H).

Example 105

(6-chloro-5-ethyl-[1,2,4]triazolo[1,5-a]pyrimidin-7-yl)-[(2-(4-trifluoromethoxyphenyl)-ethyl]-amine

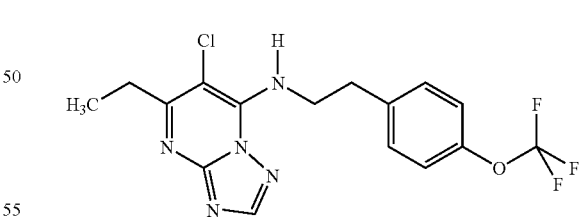

0.510 g (5.1 mmol) Triethylamine, a spatula tip of tetrabutylammonium iodide and 1.04 g (5.1 mmol) of 2-(4-trifluoromethoxyphenyl)-ethylamine were added successively to a solution of 1.0 g (4.6 mmol) of 5-ethyl-6,7-dichloro-[1,2,4]triazolo-[1,5-a]pyrimidine in 10 ml of toluene under stirring. The reaction mixture was heated at reflux for 5 hours and then stirred for another 12 hours at room temperature. The solvent was evaporated under reduced pressure and dichloromethane was added to the resulting residue. The resulting reaction mixture was washed with 2N hydrochloric acid and water. The organic phase was separated, dried and the solvent was evaporated under reduced pressure. Treatment of the resulting residue with hexane yielded 1.60 g (5.0 mmol, 99% of theory) of the title compound having a melting point of 186-187° C.

$^1$H-NMR (CDCl$_3$) δ: 8.25 (s, 1H), 7.25 (d, 2H), 7.20 (d, 2H), 6.00 (bm, 1H), 4.45 (q, 2H), 3.10 (t, 2H), 3.00 (q, 2H), 1.35 (t, 3H).

Example 114

(S)-(6-chloro-5-methyl-[1,2,4]triazolo[1,5-a]pyrimidin-7-yl)-[1-(4-fluorophenyl)-ethyl]-amine

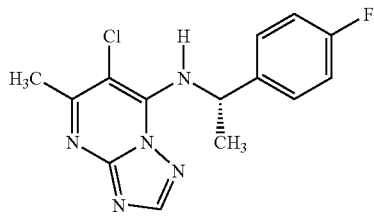 [SMILES: Cc1nc2ncnn2c(N[C@@H](C)c2ccc(F)cc2)c1Cl]

0.300 g (3.0 mmol) Triethylamine, a spatula tip of tetrabutylammonium iodide and 0.514 g (3.7 mmol) of (S)-1-(4-fluorophenyl)-ethylamine were added successively to a solution of 0.500 g (2.5 mmol) of 5-methyl-6,7-dichloro-[1,2,4]triazolo[1,5-a]pyrimidine in 10 ml of toluene under stirring. The reaction mixture was heated at reflux for 5 hours and then stirred for another 12 hours at room temperature. The solvent was evaporated under reduced pressure and dichloromethane was added to the resulting residue. The resulting reaction mixture was washed with 2N hydrochloric acid and with water. The organic phase was separated, dried and the solvent was evaporated under reduced pressure. Treatment of the resulting residue with hexane yielded 0.520 g (1.7 mmol, 68% of theory) of the title compound having a melting point of 103-104° C.

$^1$H-NMR (CDCl$_3$) δ: 8.25 (s, 1H), 7.30 (dd, 2H), 7.00 (t, 2H), 6.25 (m, 1H), 6.05 (bd, 1H), 2.60 (s, 3H), 1.75 (d, 3H);

The compounds of Inventive Examples 1 to 197 were listed in the following Table 1. The synthesis of compounds according to the invention not described was in an analogous manner as described above:

TABLE 1

(I)

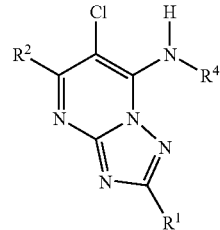

| Example No. | R$^1$ | R$^2$ | R$^{4+)}$ | m.p. [° C.] |
|---|---|---|---|---|
| 1. | H | C$_2$H$_5$ | cis-4-tert-butylcyclohexyl- | 120–122 |
| 2. | H | CH$_3$CHF | cis-4-tert-butylcyclohexyl- | 138–139 |
| 3. | H | CH$_3$ | 4-methylcyclohexyl- | 134–136 |
| 4. | H | CH$_3$ | 4-tert-butylcyclohexyl- | 165–167 |
| 5. | H | CH$_3$ | 4-(cyclohexyl-C(CH$_3$)$_2$)-cyclohexyl- | 188–190 |
| 6. | H | CH$_3$ | 4-((CH$_3$)$_2$CH)-cyclohexyl- | 109–112 |
| 7. | H | CH$_3$ | 4-tert-butylcyclohexyl- | 130–134 |
| 8. | H | CH$_3$ | cis-4-sec.-butylcyclohexyl- | 88–90 |
| 9. | H | CH$_3$ | trans-4-sec.-butylcyclohexyl- | 149–150 |
| 10. | H | CH$_3$ | trans-4-tert-butylcyclohexyl- | 138–140 |
| 11. | H | CH$_3$ | cis-(CH$_3$)$_3$C—CH$_2$—C(CH$_3$)$_2$-cyclohexyl- | 162–165 |
| 12. | H | CH$_3$ | trans-(CH$_3$)$_3$C—CH$_2$—C(CH$_3$)$_2$-cyclohexyl- | 164–166 |
| 13. | H | C$_2$H$_5$ | 4-tert-butylcyclohexyl- | 118–142 |
| 14. | H | C$_2$H$_5$ | cis-4-sec.-butylcyclohexyl- | 91–93 |
| 15. | H | C$_2$H$_5$ | trans-4-tert-butylcyclohexyl- | 183–184 |
| 16. | H | C$_2$H$_5$ | trans-4-sec.-butylcyclohexyl- | 164–165 |
| 17. | H | C$_2$H$_5$ | trans-(CH$_3$)$_3$C—CH$_2$—C(CH$_3$)$_2$-cyclohexyl- | 177–179 |
| 18. | H | C$_2$H$_5$ | 4-methylcyclohexyl- | 150–152 |
| 19. | H | C$_2$H$_5$ | 4-(cyclohexyl-C(CH$_3$)$_2$)-cyclohexyl- | 205–209 |
| 20. | H | C$_2$H$_5$ | 4-((CH$_3$)$_2$CH)-cyclohexyl- | 140–144 |
| 21. | H$_3$CSO$_2$ | C$_2$H$_5$ | cis-4-tert-butylcyclohexyl- | resinous |
| 22. | H$_3$CSO | C$_2$H$_5$ | cis-4-tert-butylcyclohexyl- | 89–97 |
| 23. | SCH$_3$ | C$_2$H$_5$ | cis-4-tert-butylcyclohexyl- | 125–128 |
| 24. | H | CF$_3$ | 4-tert-butylcyclohexyl- | 155–157 |
| 25. | H | CF$_3$ | 4-methylcyclohexyl- | 171–173 |
| 26. | H | CF$_3$ | 4-(cyclohexyl-C(CH$_3$)$_2$)-cyclohexyl- | 191–193 |
| 27. | H | CF$_3$ | 4-((CH$_3$)$_2$CH)-cyclohexyl- | 160–161 |
| 28. | H | CH$_3$CHCl | cis-4-tert-butylcyclohexyl- | 153–155 |
| 29. | H | CH$_3$ | (R)-indan-1-yl | 108–111 |
| 30. | H | CH$_3$ | (S)-indan-1-yl | 115–119 |
| 31. | H | C$_2$H$_5$ | (R)-indan-1-yl | 95–97 |
| 32. | H | C$_2$H$_5$ | (S)-indan-1-yl | 96–98 |
| 33. | H | CH$_3$ | (R)-1,2,3,4-tetrahydronaphthalen-1-yl | 110–113 |
| 34. | H | CH$_3$ | (S)-1,2,3,4-tetrahydronaphthalen-1-yl | 121–124 |
| 35. | H | C$_2$H$_5$ | (R)-1,2,3,4-tetrahydronaphthalen-1-yl | 80–81 |

TABLE 1-continued

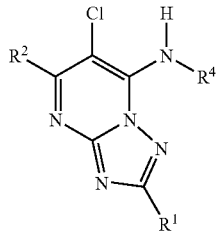

(I)

| Example No. | $R^1$ | $R^2$ | $R^{4+)}$ | m.p. [° C.] |
|---|---|---|---|---|
| 36. | H | $C_2H_5$ | (S)-1,2,3,4-tetrahydronaphthalen-1-yl | 82–84 |
| 37. | H | $CH_3$ | 4-F—$C_6H_4$— | resinous |
| 38. | H | $CH_3$ | $C_6H_5$— | 200–201 |
| 39. | H | $CH_3$ | 4-Cl—$C_6H_4$ | 138–141 |
| 40. | H | $CH_3$ | 4-$(C_6H_5)$—$C_6H_4$— | 139–141 |
| 41. | H | $CH_3$ | 4-phenoxyphenyl | 171–172 |
| 42. | H | $CH_3$ | 4-$((CH_3)_3C)$—$C_6H_4$— | 160–163 |
| 43. | H | $C_2H_5$ | 4-$((CH_3)_3C)$—$C_6H_4$— | 182–185 |
| 44. | H | $C_2H_5$ | phenyl | 201–202 |
| 45. | H | $C_2H_5$ | 4-F—$C_6H_4$— | 213–214 |
| 46. | H | $C_2H_5$ | 4-Cl—$C_6H_4$— | 200–201 |
| 47. | H | $C_2H_5$ | 4-$(C_6H_5)$—$C_6H_4$— | 159–162 |
| 48. | H | $C_2H_5$ | 4-phenoxyphenyl | 183–185 |
| 49. | H | $CF_3$ | 4-$(C_6H_5)$—$C_6H_4$— | 209–210 |
| 50. | H | $CF_3$ | $C_6H_5$— | 211–213 |
| 51. | H | $CF_3$ | 4-F—$C_6H_4$— | 193–196 |
| 52. | H | $CF_3$ | 4-Cl—$C_6H_4$— | 177–179 |
| 53. | H | $CF_3$ | 4-phenoxyphenyl | 190–193 |
| 54. | H | $CH_3CHF$ | 4-tert-butylphenyl | 183–186 |
| 55. | H | $CH_3$ | benzyl | 129–130 |
| 56. | H | $CH_3$ | 4-trifluoromethylbenzyl | 128–132 |
| 57. | H | $CH_3$ | 4-tert-butylbenzyl | 164–168 |
| 58. | H | $CH_3$ | 4-tert-butoxybenzyl | 102–105 |
| 59. | H | $CH_3$ | 3,4-$Cl_2C_6H_3$—$CH_2$— | 195–200 |
| 60. | H | $CH_3$ | 4-chlorobenzyl | 171–175 |
| 61. | H | $CH_3$ | 4-(4-methoxyphenoxy)phenyl-$CH_2$— | 132–135 |
| 62. | H | $CH_3$ | 4-(4-tert-butylphenoxy)phenyl-$CH_2$— | resinous |
| 63. | H | $CH_3$ | 4-(4-bromophenoxy)phenyl-$CH_2$— | 150–152 |
| 64. | H | $CH_3$ | 4-(4-ethylphenoxy)phenyl-$CH_2$— | 160–162 |
| 65. | H | $CH_3$ | 4-(4-methylphenoxy)phenyl-$CH_2$ | 156–158 |
| 66. | H | $CH_3$ | 4-(4-chlorophenoxy)phenyl-$CH_2$— | 146–148 |
| 67. | H | $CH_3$ | 4-(2-ethylphenoxy)phenyl-$CH_2$— | 157–159 |
| 68. | H | $CH_3$ | 4-(3-ethylphenoxy)phenyl-$CH_2$— | resinous |
| 69. | H | $CH_3$ | 4-(2-bromophenoxy)phenyl-$CH_2$— | 162–164 |
| 70. | H | $CH_3$ | 4-(3-chlorophenoxy)phenyl-$CH_2$— | 167–168 |
| 71. | H | $CH_3$ | 4-(2-methylphenoxy)phenyl-$CH_2$— | 155–161 |
| 72. | H | $CH_3$ | 4-(2-tert-butylphenoxy)phenyl-$CH_2$— | 152–155 |
| 73. | H | $CH_3$ | 4-(2-chlorophenoxy)phenyl-$CH_2$— | 165–167 |
| 74. | H | $CH_3$ | 4-(3-fluorophenoxy)phenyl-$CH_2$— | 167–174 |
| 75. | H | $CH_3$ | 4-(3-bromophenoxy)phenyl-$CH_2$ | 158–160 |
| 76. | H | $CH_3$ | 4-(4-isopropylphenoxy)phenyl-$CH_2$— | 160–163 |
| 77. | H | $CH_3$ | 4-(3-fluoro-4-chlorophenoxy)phenyl-$CH_2$— | 106–108 |
| 78. | H | $CH_3$ | 4-(3-chloro-4-bromophenoxy)phenyl-$CH_2$— | 135–138 |
| 79. | H | $CH_3$ | 4-(3-chloro-4-methylphenoxy)phenyl-$CH_2$— | 138–140 |
| 80. | H | $CH_3$ | 4-(3,4-difluorophenoxy)phenyl-$CH_2$— | 121–124 |
| 81. | H | $CH_3$ | 4-(3-methyl-4-chlorophenoxy)phenyl-$CH_2$— | 145–148 |
| 82. | H | $CH_3$ | 4-(3,4-dimethylphenoxy)phenyl-$CH_2$— | 157–159 |
| 83. | H | $CH_3$ | 4-(3-chloro-4-fluorophenoxy)phenyl-$CH_2$— | 122–125 |
| 84. | H | $CH_3$ | 4-(3,4-dichlorophenoxy)phenyl-$CH_2$— | resinous |
| 85. | H | $CH_3$ | 4-(3-methyl-4-bromophenoxy)phenyl-$CH_2$— | 158–160 |
| 86. | H | $C_2H_5$ | 4-(4-ethylphenoxy)phenyl-$CH_2$— | resinous |
| 87. | H | $C_2H_5$ | benzyl | 115–116 |
| 88. | H | $C_2H_5$ | 3,4-$Cl_2C_6H_3$—$CH_2$— | 181–184 |
| 89. | H | $C_2H_5$ | 4-$F_3C$—$C_6H_4$—$CH_2$— | 169–171 |
| 90. | H | $C_2H_5$ | 4-tert-butylphenyl-$CH_2$— | 111–113 |
| 91. | H | $C_2H_5$ | 4-(4-tert-butoxy)-$C_6H_4$—$CH_2$— | 80–85 |
| 92. | H | $C_2H_5$ | 4-Cl—$C_6H_4$—$CH_2$— | 142–146 |
| 93. | H | $C_2H_5$ | 4-(4-methoxyphenoxy)phenyl-$CH_2$— | 100–106 |
| 94. | H | $CF_3$ | $C_6H_5$—$CH_2$— | 154–156 |
| 95. | H | $CF_3$ | 4-tert-butylphenyl-$CH_2$— | 109–111 |
| 96. | H | $CH_3$ | $C_6H_5$—$CH_2CH_2$— | 161–163 |
| 97. | H | $CH_3$ | 4-Cl—$C_6H_4$—$CH_2CH_2$— | 165–167 |
| 98. | H | $CH_3$ | 4-F—$C_6H_4$—$CH_2CH_2$— | 180–182 |
| 99. | H | $CH_3$ | 4-$F_3C$—$C_6H_4$—$CH_2CH_2$— | 185–187 |

TABLE 1-continued (I)

| Example No. | $R^1$ | $R^2$ | $R^{4+)}$ | m.p. [° C.] |
|---|---|---|---|---|
| 100. | H | $CH_3$ | 3,4-$(CH_3O)_2C_6H_3$—$CH_2CH_2$— | 161–163 |
| 101. | H | $CH_3$ | 4-tert-butylphenyl-$CH_2CH_2$— | 150–151 |
| 102. | H | $CH_3$ | 4-$F_3C$—O—$C_6H_4CH_2CH_2$— | 182–184 |
| 103. | H | $C_2H_5$ | 4-F—$C_6H_4$—$CH_2CH_2$— | 162–165 |
| 104. | H | $C_2H_5$ | 4-$F_3C$—$C_6H_4$—$CH_2CH_2$— | 179–183 |
| 105. | H | $C_2H_5$ | 4-trifluoromethoxy-$C_6H_4CH_2CH_2$— | 186–187 |
| 106. | H | $C_2H_5$ | $C_6H_5$—$CH_2CH_2$— | 158–160 |
| 107. | H | $C_2H_5$ | 4-Cl—$C_6H_4$—$CH_2CH_2$— | 170–172 |
| 108. | H | $C_2H_5$ | 3,4-$(CH_3O)_2C_6H_3$—$CH_2CH_2$— | 143–145 |
| 109. | H | $C_2H_5$ | 4-tert-butylphenyl-$CH_2CH_2$— | 172–174 |
| 110. | H | $CF_3$ | 4-tert-butylphenyl-$CH_2CH_2$— | 176–178 |
| 111. | H | $CF_3$ | $C_6H_5$—$CH_2CH_2$— | 161–163 |
| 112. | H | $CF_3$ | 3,4-$(CH_3O)_2C_6H_3$—$CH_2CH_2$— | 183–186 |
| 113. | H | $CH_3CHF$ | 4-trifluoromethoxy-$C_6H_4$—$CH_2CH_2$— | 167–168 |
| 114. | H | $CH_3$ | (S)-4-F—$C_6H_4$—$CH(CH_3)$— | 103–104 |
| 115. | H | $CH_3$ | 4-Cl—$C_6H_4$—$CH(CH_3)$— | 93–95 |
| 116. | H | $CH_3$ | 4-F—$C_6H_4$—$CH(CH_3)$— | 75–77 |
| 117. | H | $CH_3$ | (R)-$C_6H_5$—$CH(CH_3)$— | 95–98 |
| 118. | H | $C_2H_5$ | 4-Cl—$C_6H_4$—$CH(CH_3)$— | resinous |
| 119. | H | $CH_3$ | 4-Br—$C_6H_4$—$CH(CH_3)$— | 79–82 |
| 120. | H | $CH_3$ | (S)-4-Cl—$C_6H_4$—$CH(CH_3)$— | 122–123 |
| 121. | H | $CH_3$ | (S)-4-$CH_3O$—$C_6H_4$—$CH(CH_3)$— | 107–108 |
| 122. | H | $CH_3$ | (S)-4-$CH_3$—$C_6H_4$—$CH(CH_3)$— | 164–166 |
| 123. | H | $CH_3$ | 3,4-$Cl_2C_6H_3$—$CH(CH_3)$— | 103–105 |
| 124. | H | $CH_3$ | 3-$ClC_6H_4$—$CH(CH_3)$— | 105–108 |
| 125. | H | $CH_3$ | 4-$F_3C$—$C_6H_4$—$CH(CH_3)$— | 85–88 |
| 126. | H | $CH_3$ | (S)-$C_6H_5$—$CH(CH_3)$— | resinous |
| 127. | H | $CH_3$ | 4-(4-$CH_3$—$C_6H_4$—O)—$C_6H_4$—$CH(CH_3)$— | 136–140 |
| 128. | H | $CH_3$ | (R)-4-$CH_3$—$C_6H_4$—$CH(CH_3)$— | 156–159 |
| 129. | H | $CH_3$ | (R)-4-Cl—$C_6H_4$—$CH(CH_3)$— | 117–122 |
| 130. | H | $CH_3$ | (R)-4-Br—$C_6H_4$—$CH(CH_3)$— | 116–119 |
| 131. | H | $CH_3$ | (S)-4-Br—$C_6H_4$—$CH(CH_3)$— | 114–130 |
| 132. | H | $CH_3$ | (R)-4-F—$C_6H_4$—$CH(CH_3)$— | 105–107 |
| 133. | H | $CH_3$ | (R)-3-$CH_3O$—$C_6H_4$—$CH(CH_3)$— | 86–110 |
| 134. | H | $CH_3$ | (S)-3-$CH_3O$—$C_6H_4$—$CH(CH_3)$— | 83–100 |
| 135. | H | $CH_3$ | 4-$CF_3O$—$C_6H_4$—$CH(CH_3)$— | 98–101 |
| 136. | H | $CH_3$ | (R)-4-$CH_3O$—$C_6H_4$—$CH(CH_3)$— | 99–136 |
| 137. | H | $CH_3$ | (R)-3-($C_6H_5$—$CH_2$—O)—$C_6H_4$—$CH(CH_3)$— | resinous |
| 138. | H | $CH_3$ | (S)-4-benzyloxy-$C_6H_4$—$CH(CH_3)$— | resinous |
| 139. | H | $CH_3$ | (R)-(naphthalen-1-yl)-$CH(CH_3)$— | 118–120 |
| 140. | H | $CH_3$ | (S)-(naphthalen-1-yl)-$CH(CH_3)$— | 117–120 |
| 141. | H | $CH_3$ | (R)-(naphthalen-2-yl)-$CH(CH_3)$— | 100–103 |
| 142. | H | $CH_3$ | (S)-(naphthalen-2-yl)-$CH(CH_3)$— | 89–91 |
| 143. | H | $CH_3$ | 4-($C_6H_5$)—$C_6H_4$—$CH(CH_3)$— | 81–88 |
| 144. | H | $CH_3$ | 1,1,2,3,3-pentamethylindan-5-yl-$CH(CH_3)$— | resinous |
| 145. | H | $CH_3$ | (R)-cyclohexyl-$CH(CH_3)$— | resinous |
| 146. | H | $CH_3$ | (S)-cyclohexyl-$CH(CH_3)$— | resinous |
| 147. | H | $C_2H_5$ | (R)-cyclohexyl-$CH(CH_3)$— | resinous |
| 148. | H | $C_2H_5$ | (S)-cyclohexyl-$CH(CH_3)$— | resinous |
| 149. | H | $C_2H_5$ | 4-Br—$C_6H_4$—$CH(CH_3)$— | resinous |
| 150. | H | $C_2H_5$ | 4-F—$C_6H_4$—$CH(CH_3)$— | 97–98 |
| 151. | H | $C_2H_5$ | (R)-$C_6H_5CH(CH_3)$— | 77–80 |
| 152. | H | $C_2H_5$ | (S)-$C_6H_5CH(CH_3)$— | resinous |
| 153. | H | $C_2H_5$ | 3,4-$Cl_2C_6H_3$—$CH(CH_3)$— | 148–150 |
| 154. | H | $C_2H_5$ | 3-$ClC_6H_4$—$CH(CH_3)$— | resinous |
| 155. | H | $C_2H_5$ | 4-$F_3C$—$C_6H_4$—$CH(CH_3)$— | resinous |
| 156. | H | $C_2H_5$ | (S)-4-$CH_3O$—$C_6H_4$—$CH(CH_3)$— | resinous |
| 157. | H | $C_2H_5$ | (S)-4-$CH_3$—$C_6H_4$—$CH(CH_3)$— | 55–58 |
| 158. | H | $C_2H_5$ | (R)-4-$CH_3$—$C_6H_4$—$CH(CH_3)$— | 63–67 |
| 159. | H | $C_2H_5$ | (S)-4-Br—$C_6H_4$—$CH(CH_3)$— | resinous |
| 160. | H | $C_2H_5$ | (R)-4-Br—$C_6H_4$—$CH(CH_3)$— | resinous |
| 161. | H | $C_2H_5$ | (S)-4-F—$C_6H_4$—$CH(CH_3)$— | resinous |
| 162. | H | $C_2H_5$ | (R)-4-F—$C_6H_4$—$CH(CH_3)$— | resinous |
| 163. | H | $C_2H_5$ | (S)-4-Cl—$C_6H_4$—$CH(CH_3)$— | resinous |

TABLE 1-continued

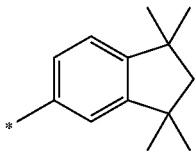

(I)

| Example No. | R¹ | R² | R⁴⁺⁾ | m.p. [° C.] |
|---|---|---|---|---|
| 164. | H | $C_2H_5$ | (R)-4-Cl—$C_6H_4$—CH(CH₃)— | resinous |
| 165. | H | $C_2H_5$ | (R)-4-NO₂—$C_6H_4$—CH(CH₃)— | 98–105 |
| 166. | H | $C_2H_5$ | (S)-4-NO₂—$C_6H_4$—CH(CH₃)— | 98–105 |
| 167. | H | $C_2H_5$ | (R)-3-CH₃O—$C_6H_4$—CH(CH₃)— | resinous |
| 168. | H | $C_2H_5$ | (S)-3-CH₃O—$C_6H_4$—CH(CH₃)— | resinous |
| 169. | H | $C_2H_5$ | (R)-4-CH₃O—$C_6H_4$—CH(CH₃)— | resinous |
| 170. | H | $C_2H_5$ | 4-F₃C—O—$C_6H_4$—CH(CH₃)— | 122–124 |
| 171. | H | $C_2H_5$ | 4-tert-butyl-$C_6H_4$—CH(CH₃)— | 93–96 |
| 172. | H | $C_2H_5$ | (R)-4-(benzyloxy)-$C_6H_4$—CH(CH₃)— | resinous |
| 173. | H | $C_2H_5$ | (S)-4-(benzyloxy)-$C_6H_4$—CH(CH₃)— | resinous |
| 174. | H | $C_2H_5$ | (R)-(naphthalen-1-yl)-CH(CH₃)— | 107–111 |
| 175. | H | $C_2H_5$ | (S)-(naphthalen-1-yl)-CH(CH₃)— | 111–112 |
| 176. | H | $C_2H_5$ | (R)-(naphthalen-2-yl)-CH(CH₃)— | 117–119 |
| 177. | H | $C_2H_5$ | (S)-(naphthalen-2-yl)-CH(CH₃)— | 115–117 |
| 178. | H | $C_2H_5$ | 4-$C_6H_5$—$C_6H_4$—CH(CH₃)— | 53–70 |
| 179. | H | $C_2H_5$ | 1,1,2,3,3-pentamethylindan-5-yl-CH(CH₃)— | resinous |
| 180. | H₃CS | $C_2H_5$ | (S)-4-Cl—$C_6H_4$—CH(CH₃)— | 128–131 |
| 181. | H | CH₃CHF | (R)-4-CH₃—$C_6H_4$—CH(CH₃)— | resinous |
| 182. | H | CH₃CHF | (R)-4-F—$C_6H_4$—CH(CH₃)— | resinous |
| 183. | H | CH₃CHF | (R)-4-Cl—$C_6H_4$—CH(CH₃)— | resinous |
| 184. | H | CH₃CHF | 4-F₃C—O—$C_6H_4$—CH(CH₃)— | 142–151 |
| 185. | H | CH₃CHF | 4-tert-butyl-$C_6H_4$—CH(CH₃)— | 102–115 |
| 186. | H | CH₃CHF | (S)-4-F—$C_6H_4$—CH(CH₃)— | resinous |
| 187. | H | CH₃CHF | (S)-4-Cl—$C_6H_4$—CH(CH₃)— | resinous |
| 188. | H | CH₃CHF | (S)-4-Br—$C_6H_4$—CH(CH₃)— | resinous |
| 189. | H | CH₃ | (2,2-difluorobenzodioxole-5-yl)C($C_2H_5$)H— | resinous |
| 190. | H | CH₃ | (R)-$C_6H_5$CH(CH₂CH₃)— | 65–120 |
| 191. | H | CH₃ | (S)-$C_6H_5$CH(CH₂CH₃)— | 63–92 |
| 192. | H | $C_2H_5$ | (R)-$C_6H_5$CH(CH₂CH₃)— | resinous |
| 193. | H | $C_2H_5$ | (S)-$C_6H_5$CH(CH₂CH₃)— | resinous |
| 194. | H | CH₃ | (R)-$C_6H_5$—CH₂—O—CH₂—CH₂—CH(CH₃)— | 48–53 |
| 195. | H | CH₃ | (S)-$C_6H_5$—CH₂—O—CH₂—CH₂—CH(CH₃)— | 65–66 |
| 196. | H | $C_2H_5$ | (R)-$C_6H_5$—CH₂—O—CH₂—CH₂—CH(CH₃)— | 70–72 |
| 197. | H | $C_2H_5$ | (S)-$C_6H_5$—CH₂—O—CH₂—CH₂—CH(CH₃)— | 67–69 |
| 198. | H | CH₃ | (S)-2-H₃C—O—$C_6H_4$—CH(CH₃)— | Oil |
| 199. | H | $C_2H_5$ | (S)-2-H₃C—O—$C_6H_4$—CH(CH₃)— | 64–69 |
| 200. | H | CH₃ | 4-cyclo-$C_6H_{11}$—$C_6H_4$—CH(CH₃)— | Oil |
| 201. | H | $C_2H_5$ | 4-cyclo-$C_6H_{11}$—$C_6H_4$—CH(CH₃)— | 110–113 |
| 202. | H | CH₃ | 4-(H₃C)₂CH—$C_6H_4$—CH(CH₃)— | Oil |
| 203. | H | $C_2H_5$ | 4-(H₃C)₂CH—$C_6H_4$—CH(CH₃)— | 75–77 |
| 204. | H | CH₃ | 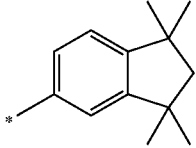 | 110–112 |
| 205. | H | $C_2H_5$ | 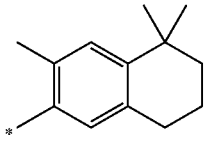 | Oil |
| 206. | H | CH₃ | | 62–67 |

TABLE 1-continued

Structure (I): a [1,2,4]triazolo[1,5-a]pyrimidine core with substituent R² at the 5-position, Cl at the 6-position, NHR⁴ at the 7-position, and R¹ at the 2-position.

| Example No. | R¹ | R² | R⁴⁺⁾ | m.p. [° C.] |
|---|---|---|---|---|
| 207. | H | C₂H₅ | 1,1,4,4,6,7-hexamethyl-1,2,3,4-tetrahydronaphthalen-? (see structure) | 59–64 |
| 208. | H | CH₃ | 1,1,4,4,6,7-hexamethyl-1,2,3,4-tetrahydronaphthalen-? (see structure) | 83–88 |
| 209. | H | C₂H₅ | 1,1,4,4,6,7-hexamethyl-1,2,3,4-tetrahydronaphthalen-? (see structure) | Oil |
| 210. | H | CH₃ | (S)-2,4-Cl₂—C₆H₃—CH(CH₃)— | 92–94 |
| 211. | H | C₂H₅ | (S)-2,4-Cl₂—C₆H₃—CH(CH₃)— | 45–47 |
| 212. | SOCH₃ | C₂H₅ | (S)-4-Cl—C₆H₄—CH(CH₃)— | 96–108 |
| 213. | SO₂CH₃ | C₂H₅ | (S)-4-Cl—C₆H₄—CH(CH₃)— | Oil |
| 214. | SCH₃ | C₂H₅ | (S)-4-CH₃—C₆H₄—CH(CH₃)— | 60–66 |
| 215. | SCH₃ | C₂H₅ | (S)-4-F—C₆H₄—CH(CH₃)— | 88–96 |
| 216. | SCH₃ | C₂H₅ | (S)-4-Br—C₆H₄—CH(CH₃)— | 138–141 |
| 217. | SCH₃ | C₂H₅ | 4-cis-(butan-2-yl)cyclohexyl- | 69–72 |
| 218. | SOCH₃ | C₂H₅ | (S)-4-CH₃—C₆H₄—CH(CH₃)— | Oil |
| 219. | SO₂CH₃ | C₂H₅ | (S)-4-CH₃—C₆H₄—CH(CH₃)— | Oil |
| 220. | SOCH₃ | C₂H₅ | (S)-4-F—C₆H₄—CH(CH₃)— | Oil |
| 221. | SO₂CH₃ | C₂H₅ | (S)-4-F—C₆H₄—CH(CH₃)— | Oil |
| 222. | SO₂CH₃ | C₂H₅ | (S)-4-Br—C₆H₄—CH(CH₃)— | 65–105 |
| 223. | SCH₃ | C₂H₅ | 4-tert.-butyl-C₆H₄— | 191–193 |
| 224. | SCH₃ | C₂H₅ | 4-F₃CO—C₆H₄—CH₂—CH₂— | 103–105 |
| 225. | OCH₃ | C₂H₅ | cis-4-tert.-butyl-cyclo-C₆H₁₁— | 123–131 |
| 226. | SO₂CH₃ | C₂H₅ | 4-tert.-butyl-C₆H₄— | 205–211 |
| 227. | SOCH₃ | C₂H₅ | 4-tert.-butyl-C₆H₄— | 240–243 |
| 228. | SOCH₃ | C₂H₅ | 4-cis-(butan-2-yl)cyclohexyl- | Oil |
| 229. | SO₂CH₃ | C₂H₅ | 4-cis-(butan-2-yl)cyclohexyl- | Oil |
| 230. | SO₂CH₃ | C₂H₅ | 4-F₃CO—C₆H₄—CH₂—CH₂— | 162–167 |
| 231. | SOCH₃ | C₂H₅ | 4-F₃CO—C₆H₄—CH₂—CH₂— | 146–149 |
| 232. | H | C₂H₅ | 4-tert.-butyl-C₆H₄— | Oil |
| 233. | H | CH₃ | (R)-2-H₃C—O—C₆H₄—CH(CH₃)— | Oil |
| 234. | H | C₂H₅ | (R)-2-H₃C—O—C₆H₄—CH(CH₃)— | 63–68 |
| 235. | H | CH₃ | (R)-2,4-Cl₂—C₆H₃—CH(CH₃)— | 84–90 |
| 236. | H | C₂H₅ | (R)-2,4-Cl₂—C₆H₃—CH(CH₃)— | 46–51 |
| 237. | H | C₂H₅ | 2-F—C₆H₄—CH(CH₃)— | 92–95 |
| 238. | H | CH₃ | 2-Cl-6-F—C₆H₃—CH(CH₃)— | 106–109 |
| 239. | H | C₂H₅ | 2-Cl-6-F-C₆H₃—CH(CH₃)— | 91–95 |
| 240. | H | CH₃ | 2-F—C₆H₄—CH(CH₃)— | 104–105 |
| 241. | H | CH₃ | (2-methyl-1,3-dioxan-2-yl)-CH(CH₃)— | 100–103 |
| 242. | H | C₂H₅ | (2-methyl-1,3-dioxan-2-yl)-CH(CH₃)— | Oil |
| 243. | H | CH₃ | (2,5,5-trimethyl-1,3-dioxan-2-yl)-CH(CH₃)— | 100–102 |
| 244. | H | C₂H₅ | (2,5,5-trimethyl-1,3-dioxan-2-yl)-CH(CH₃)— | Oil |
| 245. | H | CH₃ | 2,4-F₂—C₆H₃—CH(CH₃)— | 139–140 |
| 246. | H | C₂H₅ | 2,4-F₂—C₆H₃—CH(CH₃)— | 113–115 |

TABLE 1-continued

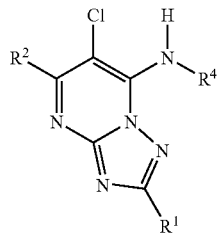

(I)

| Example No. | $R^1$ | $R^2$ | $R^{4+)}$ | m.p. [° C.] |
|---|---|---|---|---|
| 247. | H | $CH_3$ | 4-Cl-2-F—$C_6H_3$—$CH(CH_3)$— | 106–109 |
| 248. | H | $C_2H_5$ | 4-Cl-2-F—$C_6H_3$—$CH(CH_3)$— | 97–99 |
| 249. | $OCH_3$ | $C_2H_5$ | (S)-4-F—$C_6H_4$—$CH(CH_3)$— | Oil |
| 250. | $OCH_3$ | $C_2H_5$ | (S)-4-Cl—$C_6H_4$—$CH(CH_3)$— | Oil |
| 251. | $OCH_3$ | $C_2H_5$ | (S)-4-Br—$C_6H_4$—$CH(CH_3)$— | Oil |
| 252. | a | $C_2H_5$ | cis-4-tert.-butyl-cyclo-$C_6H_{11}$— | 102–105 |
| 253. | b | $C_2H_5$ | cis-4-tert.-butyl-cyclo-$C_6H_{11}$— | Oil |
| 254. | c | $C_2H_5$ | cis-4-tert.-butyl-cyclo-$C_6H_{11}$— | Oil |
| 255. | d | $C_2H_5$ | cis-4-tert.-butyl-cyclo-$C_6H_{11}$— | Oil |
| 256. | e | $C_2H_5$ | cis-4-tert.-butyl-cyclo-$C_6H_{11}$— | Oil |
| 257. | f | $C_2H_5$ | cis-4-tert.-butyl-cyclo-$C_6H_{11}$— | 110–143 |
| 258. | g | $C_2H_5$ | cis-4-tert.-butyl-cyclo-$C_6H_{11}$— | 75–90 |
| 259. | h | $C_2H_5$ | cis-4-tert.-butyl-cyclo-$C_6H_{11}$— | 78–85 |
| 260. | i | $C_2H_5$ | cis-4-tert.-butyl-cyclo-$C_6H_{11}$— | Oil |
| 261. | CN | $C_2H_5$ | cis-4-tert.-butyl-cyclo-$C_6H_{11}$— | 151–153 |
| 262. | $OCH_3$ | $C_2H_5$ | 4-cis-(butan-2-yl)cyclohexyl- | 58–69 |
| 263. | OH | $C_2H_5$ | 4-cis-(butan-2-yl)cyclohexyl- | Oil |
| 264. | k | $C_2H_5$ | 4-cis-(butan-2-yl)cyclohexyl- | Oil |
| 265. | H | $CH_3$ | 4-$F_2HCO$—$C_6H_4$—$CH(CH_3)$— | 90–91 |
| 266. | H | $C_2H_5$ | 4-$F_2HCO$—$C_6H_4$—$CH(CH_3)$— | 102–103 |
| 267. | H | $CH_3$ | 4-$F_2HC$—$CF_2O$—$C_6H_4$—$CH(CH_3)$— | 85–86 |
| 268. | H | $C_2H_5$ | 4-$F_2HC$—$CF_2O$—$C_6H_4$—$CH(CH_3)$— | 82–83 | m.p. = melting point
+)(S) refers always to the configuration of $CH(CH_3)$ at the nitrogen atom; and * indicates the position at which the radical is bound to the remainder of the molecule
a: $H_3CO$—C(O)—$CH_2$—S—;
b: $H_3CO$—$CH_2CH_2$—S—;
c: $H_3CO$—C(O)—$CH_2CH_2$—S—;
d: $H_3CO$—$CH_2CH_2$—O—;
e: $H_3CO$—$CH_2CH_2$—O—$CH_2CH_2$—O—;
f: HO—C(O)—$CH_2$—S—;
g: $H_3C$—$CH_2$—O—;
h: $(H_3C)_2CH$—O—;
i: HC≡C—$CH_2$—O—;
k: $H_5C_6$—$CH_2$—O—

2. EXAMPLES OF ACTION AGAINST PESTS

The action of the compounds of the formula I against pests was demonstrated by the following experiments: The active compounds were formulated
a. for testing the activity against *Aphis gossypii, Tetranychus urticae, Myzus persicae*, and *Aphis fabae*, as 50:50 acetone:water solutions amended with 100 ppm Kinetic® (surfactant),
b. for testing the activity against *Spodoptera eridania* as a 10.000 ppm solution in a mixture of 35% acetone and water, which was diluted with water, if needed,
c. for testing the activity against *Nilaparvata lugens* and *Sogatella furcifera* as a 20:80 acetone:water solution. Surfactant (Alkamuls EL 620) was added at the rate of 0.1% (vol/vol).

After the experiments were completed, in each case the lowest concentration was determined at which the compound still caused an 75 to 100% inhibition or mortality in comparison with untreated controls (limit or minimal concentration).
Cotton Aphid (*Aphis gossypii*)

Cotton plants in the cotyledon stage (variety 'Delta Pine') are infested with approximately 100 laboratory-reared aphids by placing infested leaf sections on top of the test plants. The leaf sections are removed after 24 hr. The cotyledons of the intact plants are dipped into gradient solutions of the test compound. Aphid mortality on the treated plants, relative to mortality on check plants, is determined after 5 days.

In this test, compounds of examples nos 1, 4, 5, 6, 7, 8, 13, 14, 18, 19, 20, 58, 62, 65, 66, 68, 76, 80, 91, 101, 108, 114, 115, 116, 118, 119, 120, 121, 122, 126, 150, 152, 156, 157, 158, 159, 160, 161, 162, 163 and 189 at 300 ppm showed over 75% mortality in comparison with untreated controls.
Twospotted Spider Mite (*Tetranychus urticae*)

Lima bean plants in the $1^{st}$ leaf-pair stage (variety 'Henderson') are infested with approximately 100 laboratory-reared mites per leaf by placing infested leaf sections on top of the test plants. The leaf sections are removed after 24 hr. The foliage of the intact plants is dipped into gradient solutions of the test compound. Mite mortality is determined after 5 days.

In this test, compounds of examples nos. 1, 5, 52 56, 57, 58, 59, 60, 78, 82, 84, 87, 90, 91, 101, 115, 119 and 120 at 300 ppm showed over 75% mortality in comparison with untreated controls.

Green Peach Aphid (*Myzus persicae*)

Pepper plants in the $2^{nd}$ leaf-pair stage (variety 'California Wonder') are infested with approximately 40 laboratory-reared aphids by placing infested leaf sections on top of the test plants. The leaf sections are removed after 24 hr. The leaves of the intact plants are dipped into gradient solutions of the test compound. Aphid mortality on the treated plants, relative to mortality on check plants, is determined after 5 days.

In this test, compounds of examples nos. 1, 4, 5, 6, 7, 8, 13, 14, 19, 20, 55, 57, 89, 106, 107, 109, 114, 115, 116, 118, 119, 120, 121, 122, 123, 125, 126, 152, 156, 157, 158, 159, 160, 161, 162, 163 and 189 at 300 ppm showed a 100% mortality in comparison with untreated controls.

Bean Aphid (*Aphis fabae*)

Nasturtium plants in the $1^{st}$ leaf-pair stage (variety 'Mixed Jewel') are infested with approximately 25 laboratory-reared aphids by placing infested cut plants on top of the test plants. The cut plants are removed after 24 hr. The foliage and stem of the test plants are dipped into gradient solutions of the test compound. Aphid mortality is determined after 3 days.

In this test, compounds of examples nos. 1, 5, 6, 76, 120, 126, 149, 161 and 163 at 300 ppm showed over 75% mortality in comparison with untreated controls.

Southern Armyworm (*Spodoptera eridania*), 2nd Instar Larvae

Foliage of two Sieva lima beans plants at the first expanded true-leaf stage that are contained within a single 3.8 cm square plastic pot are dipped into the test solution with agitation for 3 seconds and allowed to dry in a hood. The pot is then placed in a 25.4 cm plastic zipper top bag and infested with ten $2^{nd}$ instar caterpillars. At 5 days, observations are made of mortality, reduced feeding, or any interference with normal molting.

In this test, compounds of examples nos. 51, 80, 119, 159, 161 and 163 at 300 ppm showed over 75% mortality in comparison with untreated controls.

Brown Plant Hopper (*Nilaparvata lugens*)
White-Backed Plant Hopper (*Sogatella furcifera*)

Potted rice plants of 3-4 weeks of age are sprayed with 10 ml of the test solution using air driven hand atomizer (Devilibis atomizer) at 1.7 bar. The treated plants are allowed to dry for about 1 hour and covered with Mylar cages. The plants are inoculated with 10 adults of each species (5 male and 5 females) and kept at 25-27° C. and 50-60% humidity for 3 days. Mortality is assed after 24, 48 and 72 hours after treatment. Dead insects are usually found in the water surface. Each treatment is replicated once.

In this test, compounds I at 500 ppm showed over 75% mortality of *Nilaparvata lugens* in comparison with untreated controls.

In this test, compounds I at 500 ppm showed over 75% mortality of *Sogatella furcifera* in comparison with untreated controls.

We claim:

1. A method of combating insects which comprises contacting the insects, their habitat, breeding ground, food supply, plant, seed, soil, area, material or environment in which the insects are growing or may grow, or the materials, plants, seeds, soils, surfaces or spaces to be protected from insect attack or infestation with a insecticidally effective amount of at least one 6-halogeno-[1,2,4]-triazolo[1,5-a]-pyrimidine of the general formula I

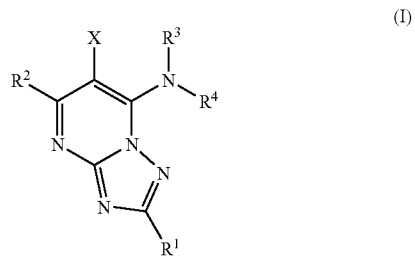

wherein

X is halogen;

$R^1$ is hydrogen;

$R^2$ is $C_1$-$C_{10}$-alkyl or $C_1$-$C_2$-fluoralkyl;

$R^3$ is hydrogen; and $R^4$ is $C_3$-$C_8$-cycloalkyl, phenyl, or phenyl-C1-C4-alkyl wherein each phenyl and $C_3$-$C_8$-cycloalkyl may be unsubstituted or may carry one or two radicals which are selected, independently from each other, from the group consisting of halogen, cyano, nitro, hydroxy, $C_1$-$C_{10}$-alkyl, $C_1$-$C_{10}$-alkoxy, $C_1$-$C_{10}$-haloalkyl, $C_1$-$C_{10}$-haloalkoxy, amino, $C_1$-$C_{10}$-alkylamino, di($C_1$-$C_{10}$-alkyl)amino, $C_1$-$C_{10}$-alkylthio, $C_1$-$C_{10}$-alkylsulfonyl, $C_3$-$C_8$-cycloalkyl, $C_3$-$C_8$-cycloalkyl-$C_1$-$C_4$-alkyl, phenyl, phenyl-$C_1$-$C_4$-alkoxy and phenyloxy, wherein the five last-mentioned radicals for their part may be unsubstituted or may carry one, two or three substituents which are selected, independently from each other, from the group consisting of $C_1$-$C_4$-alkyl, $C_1$-$C_4$-alkoxy and halogen, it being also possible for $C_3$-$C_{10}$-cycloalkyl and phenyl groups to be fused to a 5- to 7-membered saturated, unsaturated or aromatic carbocyclic ring or to a 5- to 7-membered heterocyclic ring and said fused ring may be unsubstituted or may itself carry one, two, three, four, five or six substituents which are selected, independently from each other from the group consisting of halogen and $C_1$-$C_4$-alkyl;

and/or at least one agriculturally acceptable salt thereof, thereby combating insects.

2. The method as claimed in claim 1, wherein the radical $R^2$ in formula I is $C_1$-$C_4$-alkyl or $C_1$-$C_2$-fluoralkyl.

3. The method as claimed in claim 2, wherein the radical $R^2$ in formula I is $C_1$-$C_2$-alkyl or $C_1$-$C_2$-fluoroalkyl.

4. The method as claimed in claim 1, wherein the radical $R^4$ in formula I is cyclohexyl which carries a substituent in the 4-position.

5. The method as claimed in claim 4, wherein the substituent is $C_1$-$C_4$-alkyl.

6. The method as claimed in claim 1, wherein the radical $R^4$ in formula I is 1-phenylethyl which carries a substituent in the 4-position.

7. The method as claimed in claim 6, wherein the substituent is selected from the group consisting of halogen, $C_1$-$C_4$-alkyl, $C_1$-$C_4$-alkoxy, $C_1$-$C_4$-haloalkyl and $C_1$-$C_4$-haloalkoxy.

8. A method for protecting crops-from attack or infestation by insects which comprises contacting the crops with a insecticidally effective amount of a 6-halogeno-[1,2,4]-triazolo[1,5-a]-pyrimidine of the general formula I

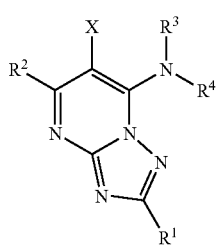

(I)

wherein
X is halogen;
$R^1$ is hydrogen;
$R^2$ is $C_1$-$C_{10}$-alkyl or $C_1$-$C_2$-fluoroalkyl;
$R^3$ is hydrogen; and
$R^4$ is $C_3$-$C_8$-cycloalkyl, phenyl, or phenyl-C1-C4-alkyl, wherein each phenyl and $C_3$-$C_8$-cycloalkyl may be unsubstituted or carry one or two radicals which are selected, independently from each other, from the group consisting of halogen, cyano, nitro, hydroxy, $C_1$-$C_{10}$-alkyl, $C_1$-$C_{10}$-alkoxy, $C_1$-$C_{10}$-haloalkyl, $C_1$-$C_{10}$-haloalkoxy, amino, $C_1$-$C_{10}$-alkylamino, di($C_1$-$C_{10}$-alkyl)amino, $C_1$-$C_{10}$-alkylthio, $C_1$-$C_{10}$-alkylsulfinyl, $C_1$-$C_{10}$-alkylsulfonyl, $C_3$-$C_8$-cycloalkyl, $C_3$-$C_8$-cycloalkyl-$C_1$-$C_4$-alkyl, phenyl, phenyl-$C_1$-$C_4$-alkoxy and phenyloxy, wherein the five last-mentioned radicals for their part may be unsubstituted or may carry one, two or three substituents which are selected, independently from each other, from the group consisting of $C_1$-$C_4$-alkyl, $C_1$-$C_4$-alkoxy and halogen, it being also possible for $C_3$-$C_{10}$-cycloalkyl and phenyl groups to be fused to a 5- to 7-membered saturated, unsaturated or aromatic carbocyclic ring or to a 5- to 7-membered heterocyclic ring and said fused ring may be unsubstituted or may itself carry one, two, three, four, five or six substituents which are selected, independently from each other from the group consisting of halogen and $C_1$-$C_4$-alkyl;

and/or at least one salt thereof, thereby protecting crops.

9. The method as claimed in claim 1, wherein the radical $R^4$ in formula I is phenyl, phenyl-$C_1$-$C_4$-alkyl or $C_3$-$C_8$-cycloalkyl, wherein each phenyl and $C_3$-$C_8$-cycloalkyl group may be unsubstituted or may carry one or two substituents which are selected, independently from each other, from the group consisting of halogen, cyano, nitro, hydroxy, $C_1$-$C_{10}$-alkyl, $C_1$-$C_{10}$-alkoxy, $C_1$-$C_{10}$-haloalkyl, $C_1$-$C_{10}$-haloalkoxy, amino, $C_1$-$C_{10}$-alkylamino, di($C_1$-$C_{10}$-alkyl)amino, $C_1$-$C_{10}$-alkylthio, $C_1$-$C_{10}$-alkylsulfinyl, $C_1$-$C_{10}$-alkylsulfonyl, $C_3$-$C_8$-cycloalkyl, $C_3$-$C_8$-cycloalkyl-$C_1$-$C_4$-alkyl, phenyl, phenyl-$C_1$-$C_4$-alkoxy and phenyloxy.

10. The method as claimed in claim 9, wherein the radical $R^4$ in formula I is cyclohexyl which carries a substituent in the 4-position, the substituent being $C_1$-$C_4$-alkyl.

11. The method as claimed in claim 9, wherein the radical $R^4$ in formula I is 1-phenylethyl which carries a substituent in the 4-position, wherein the substituent is selected from the group consisting of halogen, $C_1$-$C_4$-alkyl, $C_1$-$C_4$-alkoxy, $C_1$-$C_4$-haloalkyl and $C_1$-$C_4$-haloalkoxy.

* * * * *